US008754068B2

(12) United States Patent
Regueiro-Ren et al.

(10) Patent No.: US 8,754,068 B2
(45) Date of Patent: Jun. 17, 2014

(54) MODIFIED C-3 BETULINIC ACID DERIVATIVES AS HIV MATURATION INHIBITORS

(75) Inventors: Alicia Regueiro-Ren, Middletown, CT (US); Jacob Swidorski, Southington, CT (US); Zheng Liu, Beacon Falls, CT (US); Nicholas A. Meanwell, East Hampton, CT (US); Sing-Yuen Sit, Meriden, CT (US); Jie Chen, Madison, CT (US); Ny Sin, East Hampton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 316 days.

(21) Appl. No.: 13/151,706

(22) Filed: Jun. 2, 2011

(65) Prior Publication Data

US 2012/0142707 A1    Jun. 7, 2012

Related U.S. Application Data

(60) Provisional application No. 61/351,338, filed on Jun. 4, 2010.

(51) Int. Cl.
*A61K 31/56*    (2006.01)
*A61K 31/58*    (2006.01)
*C07J 53/00*    (2006.01)

(52) U.S. Cl.
USPC ........... 514/169; 514/172; 514/176; 514/182; 540/47; 552/510

(58) Field of Classification Search
USPC ............ 514/169, 172, 176, 183, 182; 540/47; 544/58.2, 106, 358, 383; 546/184, 242, 546/245; 548/146, 152, 267.6, 300.1, 400; 549/76; 552/510; 564/161
See application file for complete search history.

(56) References Cited

U.S. PATENT DOCUMENTS

| 5,679,828 | A  | 10/1997 | Lee et al.    |
| 7,354,924 | B2 | 4/2008  | Wang et al.   |
| 7,365,221 | B2 | 4/2008  | Allaway et al.|
| 7,745,625 | B2 | 6/2010  | Ueda et al.   |
| 2005/0239748 | A1 | 10/2005 | Power et al. |
| 2008/0207573 | A1 | 8/2008  | Yager et al. |
| 2010/0216751 | A1 | 8/2010  | Jacob et al. |

FOREIGN PATENT DOCUMENTS

| WO | WO 98/51293    | 11/1998 |
| WO | WO 98/51294    | 11/1998 |
| WO | WO 99/45025    | 9/1999  |
| WO | WO 2004/089357 | 10/2004 |
| WO | WO 2005/112929 | 12/2005 |
| WO | WO 2008/127364 | 10/2008 |
| WO | WO 2009/100532 | 8/2009  |
| WO | WO 2009/114083 | 9/2009  |

OTHER PUBLICATIONS

U.S. Appl. No. 61/537,099, filed Sep. 21, 2011, Liu et al.
U.S. Appl. No. 61/599,040, filed Feb. 15, 2012, Swidorski et al.
U.S. Appl. No. 13/151,722, filed Jun. 2, 2011, Regueiro-Ren et al.
U.S. Appl. No. 13/359,680, filed Jan. 27, 2012, Regueiro-Ren et al.
U.S. Appl. No. 13/359,727, filed Jan. 27, 2012, Regueiro-Ren et al.
Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Ma, C. et al., "Chemical Modification of Oleanene Type Triterpenes and Their Inhibitory Activity Against HIV-1 Protease Dimerization", Chem. Pharm. Bull, vol. 48, No. 11, pp. 1681-1688 (2000).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).
Zhu, Y.-M. et al., "Synthesis and Anti-HIV Activity of Oleanolic Acid Derivatives", Bioorganic & Medicinal Chemistry Letters, vol. 11, pp. 3115-3118 (2001).

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, modified C-3 betulinic acid and other structurally related natural products derivatives that possess unique antiviral activity are provided as HIV maturation inhibitors. These compounds are useful for the treatment of HIV and AIDS.

24 Claims, No Drawings

US 8,754,068 B2

MODIFIED C-3 BETULINIC ACID DERIVATIVES AS HIV MATURATION INHIBITORS

CROSS-REFERENCE TO RELATED APPLICATION

This non-provisional application claims the benefit of U.S. Provisional Application Ser. No. 61/351,338 filed Jun. 4, 2010.

FIELD OF THE INVENTION

The present invention relates to novel compounds useful against HIV, and more particularly, to compounds derived from betulinic acid and other structurally related compounds which are useful as HIV maturation inhibitors, and to pharmaceutical compositions containing same, as well as to methods for their preparation and use.

BACKGROUND OF THE INVENTION

HIV-1 (human immunodeficiency virus-1) infection remains a major medical problem, with an estimated 45 million people infected worldwide at the end of 2007. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®, emtricitabine (or FTC-EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®, delavirdine (or RESCRIPTOR®) and efavirenz (or SUSTIVA®, ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and US 2005/0209246 are illustrative of HIV attachment inhibitors.

Another emerging class of HIV treatment compounds are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the caspid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the 3 carbon of betulin with succinic acid also produced a compound capable of inhibiting HIV-1 activity (Pokrovskii, A. G., et al., Gos. Nauchnyi Tsentr Virusol. Biotekhnol. "Vector" 9:485-491 (2001)).

Other references to the use of treating HIV infection with compounds derived from betulinic acid include US 2005/0239748 and US 2008/0207573.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) 1up-20(29)-en-28-oic acid.

Reference is also made herein to the provisional application by Bristol-Myers Squibb entitled "C-28 AMIDES OF MODIFIED C-3 BETULINIC ACID DERIVATIVES AS HIV MATURATION INHIBITORS," filed on Jun. 4, 2010 and assigned U.S. Ser. No. 61/351,332.

What is now needed in the art are new compounds which are useful as HIV maturation inhibitors, as well as new pharmaceutical compositions containing these compounds.

SUMMARY OF THE INVENTION

The present invention provides compounds of Formula I, II and III below, including pharmaceutically acceptable salts thereof, their pharmaceutical formulations, and their use in patients suffering from or susceptible to a virus such as HIV. The compounds of Formula I-III are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of formula I

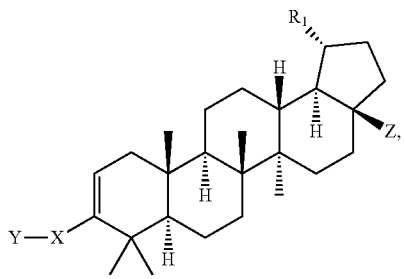

Formula I a compound of formula II

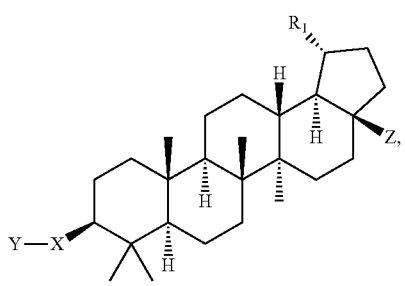

Formula II a compound of formula III

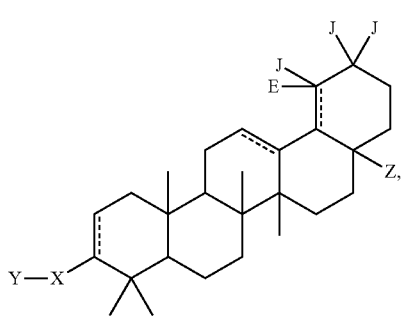

Formula III wherein $R_1$ is isopropenyl or isopropyl;
J and E are —H or —$CH_3$;
E is absent when the double bond is present;
X is a phenyl or heteroaryl ring substituted with A, wherein A is at least one member selected from the group of —H, -halo, -hydroxyl, —$C_{1-6}$ alkyl, —$C_{1-6}$ alkoxy, —$C_{1-6}$ haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$, wherein $R_2$ is H, —$C_{1-6}$ alkyl, or substituted —$C_{1-6}$ alkyl and wherein $R_3$ is $C_{1-6}$ alkyl and further wherein n=1-6;

Y is selected from the group of —$COOR_2$, —$C(O)NR_2R_2$, —$C(O)NR_2SO_2R_3$, —$C(O)NR_2SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, —$CONHOH$, -bicyclic heteroaryl-$COOR_2$, and —$B(OH)_2$, wherein n=1-6; and Z is selected from the group of —COOH, —$COOR_4$ and —$CH_2OH$, wherein $R_4$ is $C_{1-6}$ alkyl or $C_{1-6}$ alkylphenyl.

In a further embodiment, there is provided a method for treating mammals infected with a virus, especially wherein said virus is HIV, comprising administering to said mammal an antiviral effective amount of a compound which is selected from the group of compounds of Formulas I, II, III above, and one or more pharmaceutically acceptable carriers, excipients or diluents. Optionally, the compound of Formulas I, II and/or III can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II and III, and one or more pharmaceutically acceptable carriers, excipients, and diluents; and optionally in combination with an antiviral effective amount of an AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II and III.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II, III in addition to the mixtures thereof.

The terms "C-3" and "C-28" refer to certain positions of a triterpene core as numbered in accordance with IUPAC rules (positions depicted below with respect to an illustrative triterpene: betulin):

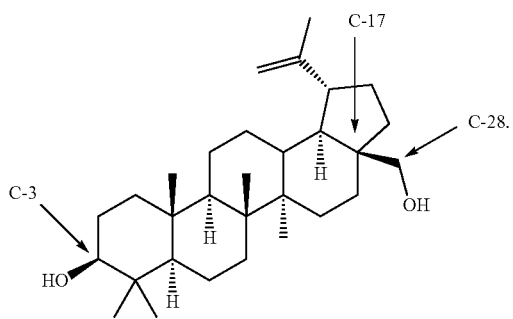

The same numbering is maintained when referring to the compound series in schemes and general description of methods.

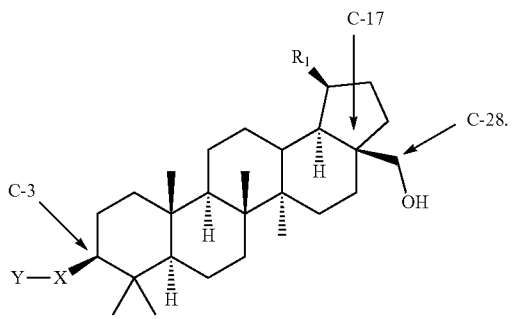

DEFINITIONS

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$-fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-Sulfonamido" group refers to a R"S(=O)$_2$NR$_x$— group, with R$_x$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^X$ and R$^Y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$) alkyl.

A "guanidino" group refers to a —R$^x$NC(=N)NR$^y$R$^{y2}$ group, with R$^x$, R$^y$, and R$^{y2}$ independently being H or (C$_{1-6}$) alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$) alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

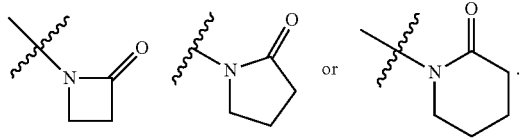

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates, half acid esters such as malonates, succinates or glutarates, and the like. In certain embodiments, amino acid esters may be especially preferred.

Examples of such prodrug esters include

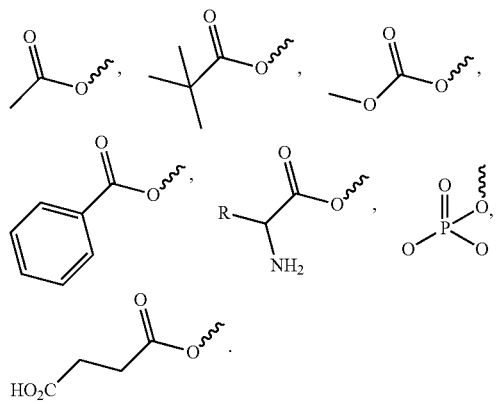

The term "prodrug ethers" include both phosphate acetals and O-glucosides. Representative examples of such prodrug ethers include

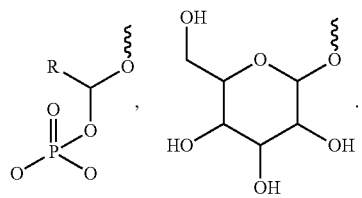

As set forth above, the invention is directed to a compound, including pharmaceutically acceptable salts thereof, which is selected from the group of:

a compound of formula I

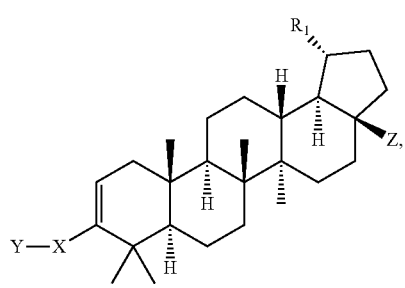

a compound of formula II

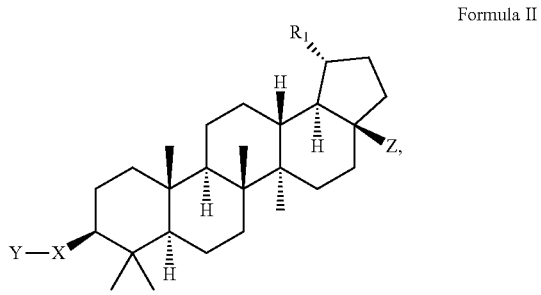

a compound of formula III

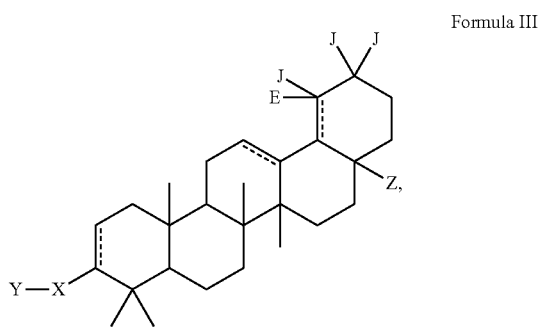

wherein $R_1$ is isopropenyl or isopropyl;

J and E are —H or —$CH_3$;

E is absent when the double bond is present;

X is a phenyl or heteroaryl ring substituted with A, wherein A is at least one member selected from the group of —H, -halo, -hydroxyl, —$C_{1-6}$ alkyl, —$C_{1-6}$ alkoxy, —$C_{1-6}$ haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$, wherein $R_2$ is H, —$C_{1-6}$ alkyl, or substituted —$C_{1-6}$ alkyl and wherein $R_3$ is $C_{1-6}$ alkyl and further wherein n=1-6;

Y is selected from the group of —$COOR_2$, —$C(O)NR_2R_2$, —$C(O)NR_2SO_2R_3$, —$C(O)NR_2SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$alkyl-$COOR_2$, —$NHC(O)(CH_2)_n$—$COOR_2$, —$SO_2NR_2C(O)R_2$, -tetrazole, —CONHOH, -bicyclic heteroaryl-$COOR_2$, and —$B(OH)_2$, wherein n=1-6; and Z is selected from the group of —COOH, —$COOR_4$ and —$CH_2OH$, wherein $R_4$ is $C_{1-6}$ alkyl or $C_{1-6}$ alkylphenyl.

More preferred compounds include those which are encompassed by Formula I. Of these, those wherein X is a phenyl ring are even more preferred. Also preferred are compounds of Formula I wherein A is at least one member selected from the group of —H, —OH, -halo, —$C_{1-3}$ alkyl, and —$C_{1-3}$ alkoxy, wherein -halo is selected from the group of —Cl, —F and —Br. Also preferred are compounds of Formula I wherein Y is —COOH.

In another preferred embodiment there is provided a compound of Formula Ia below wherein X is a phenyl ring and Y is —COOH in the para position:

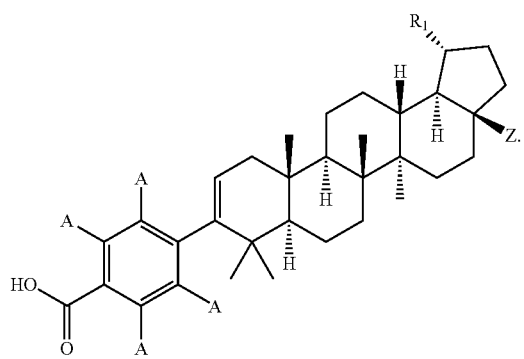
Formula Ia
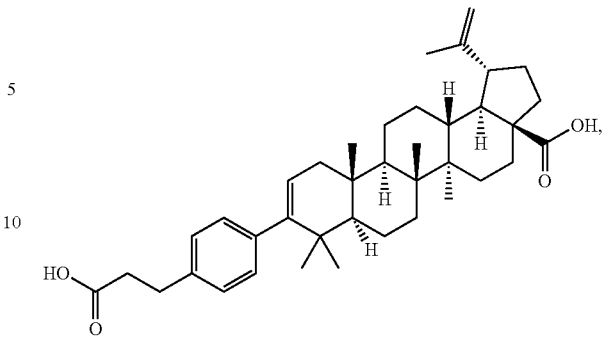
In this embodiment, it is also preferred that A is at least one member selected from the group of —H, -halo, —OH, —$C_{1-3}$ alkyl and —$C_{1-3}$ alkoxy. It is particularly preferred that A is at least one member selected from the group of —H, -fluoro, -chloro, —OH, methyl and methoxy.
Other compounds derived from Formula I which are preferred as part of the invention include,
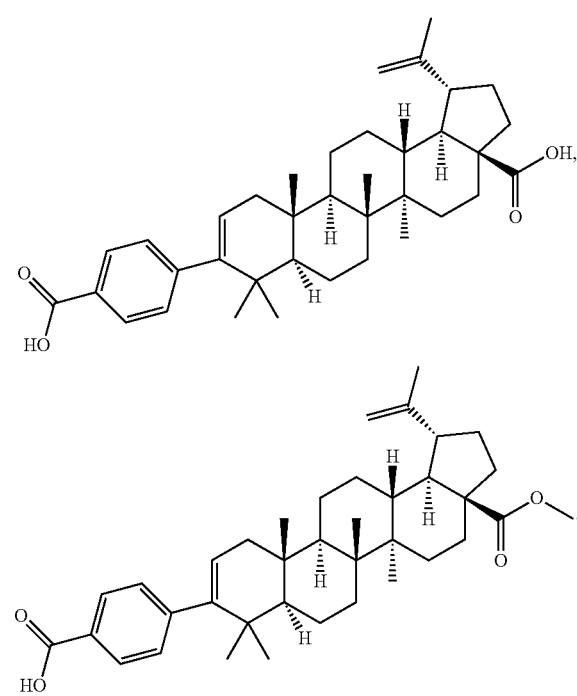
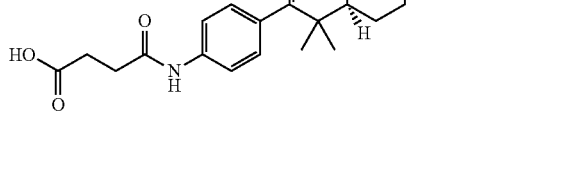
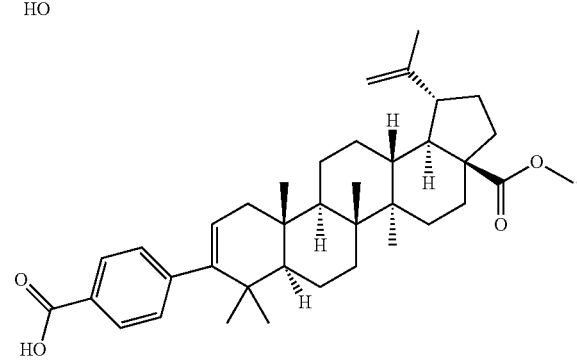
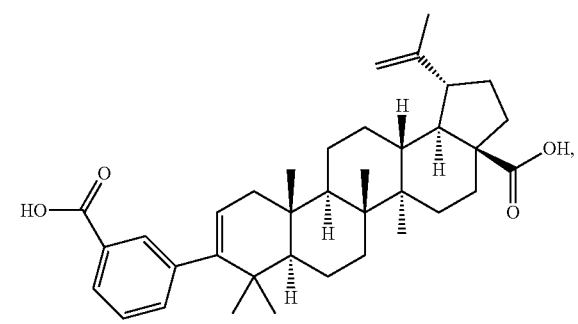
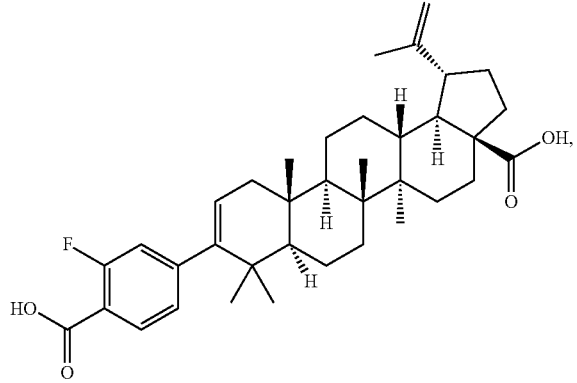

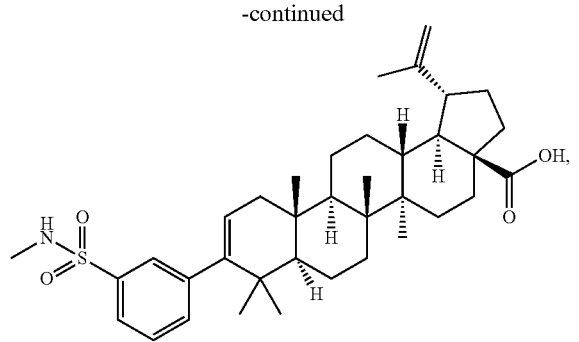
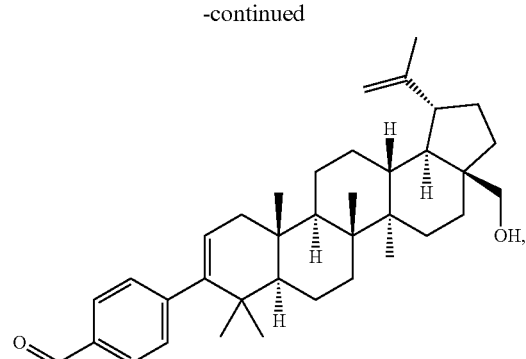
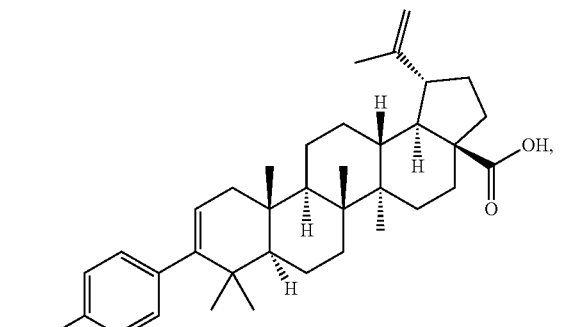
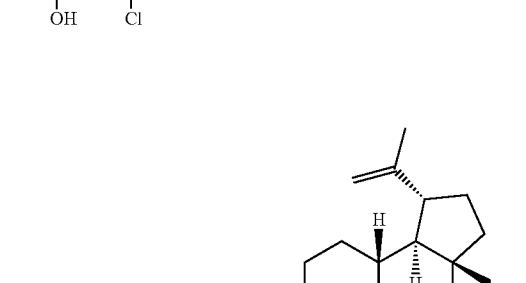
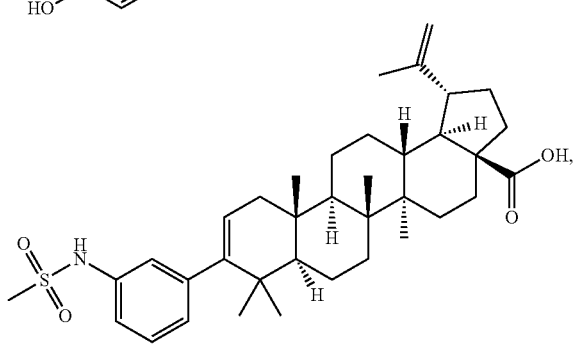
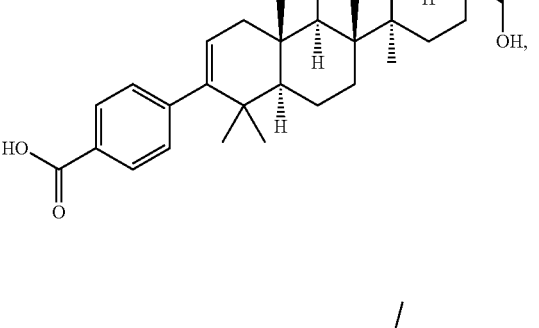
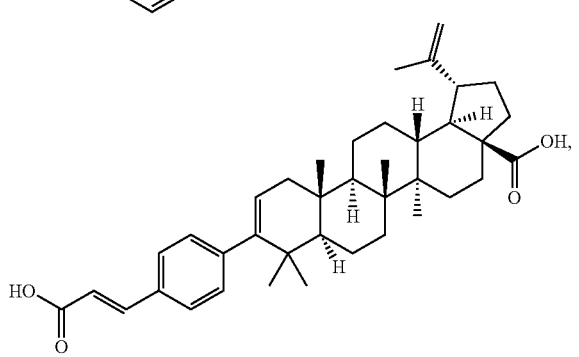
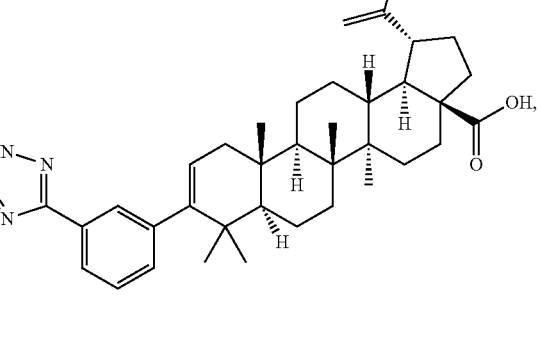
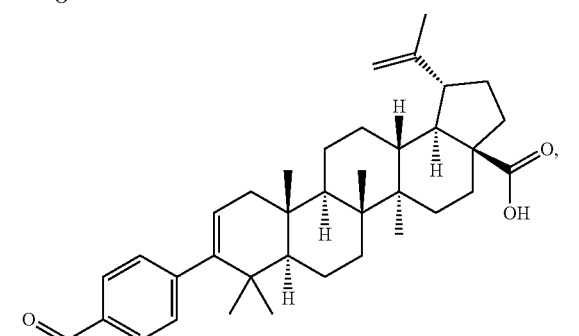
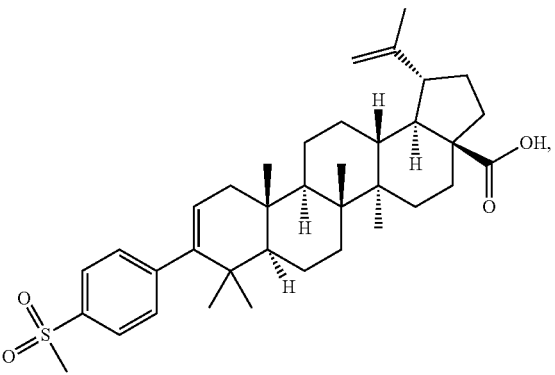

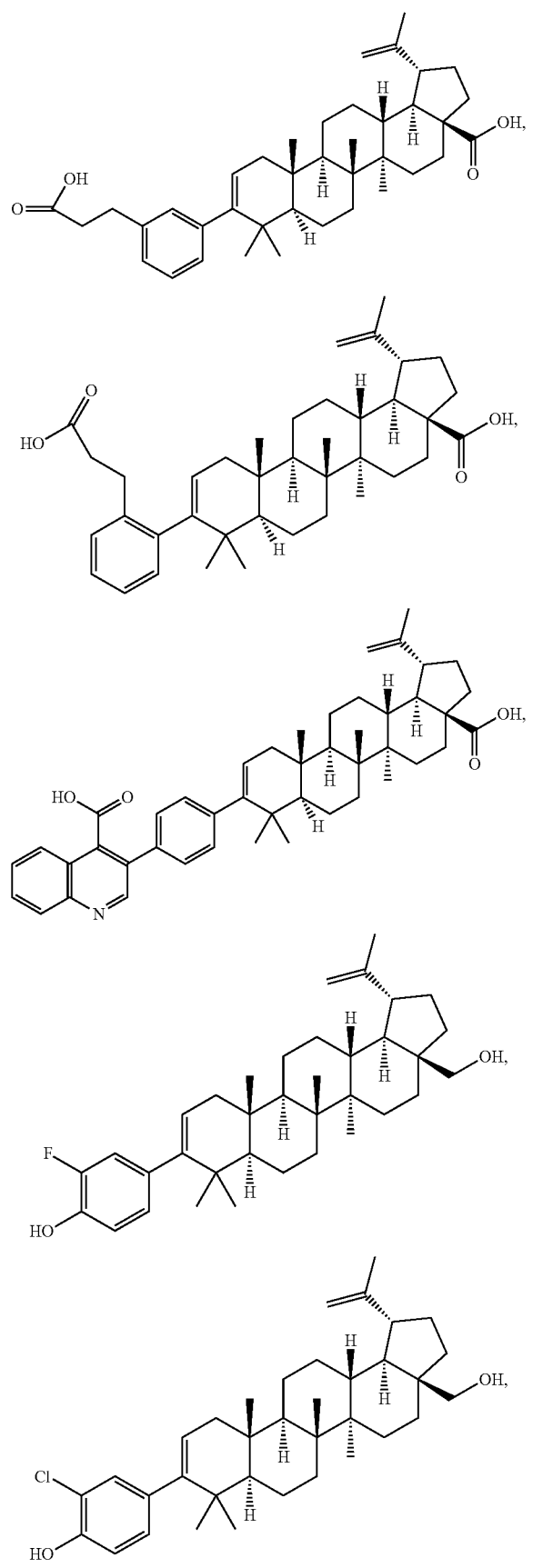
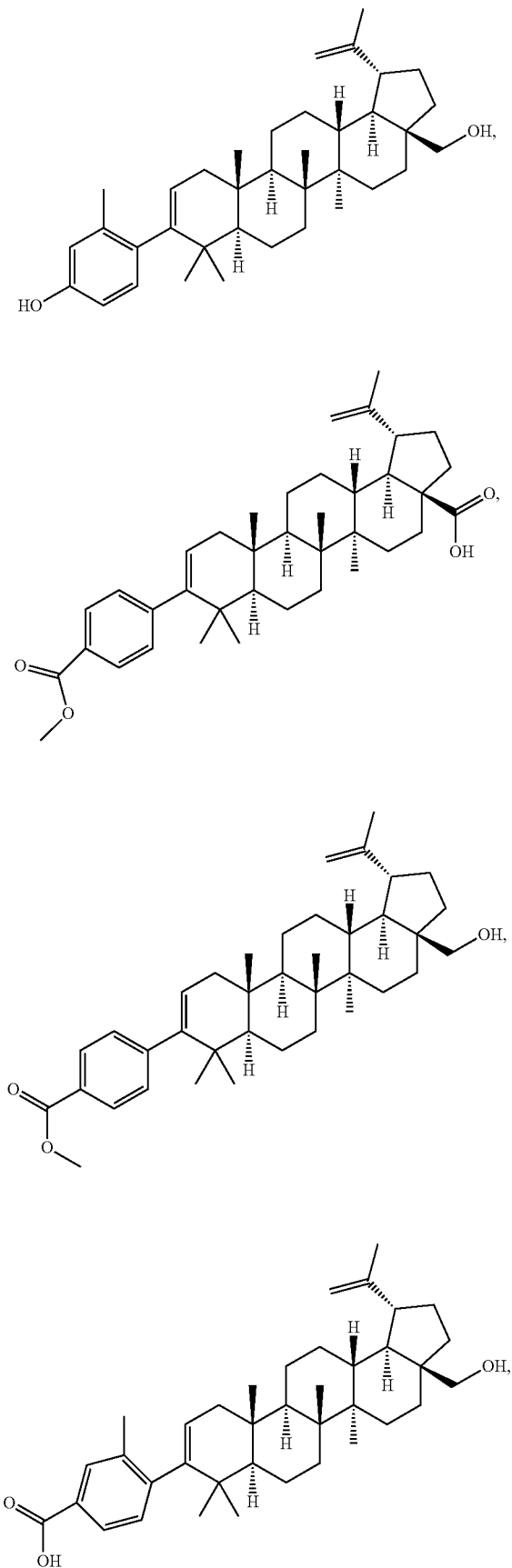

17
-continued
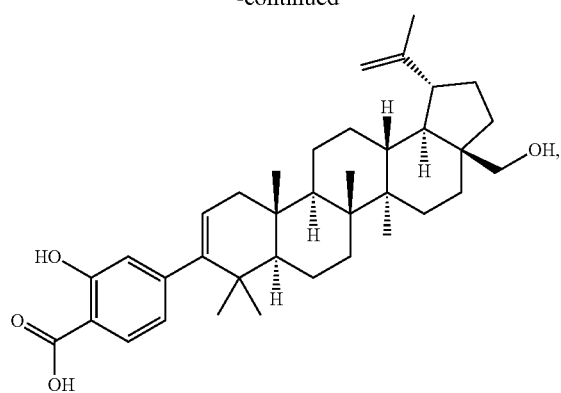
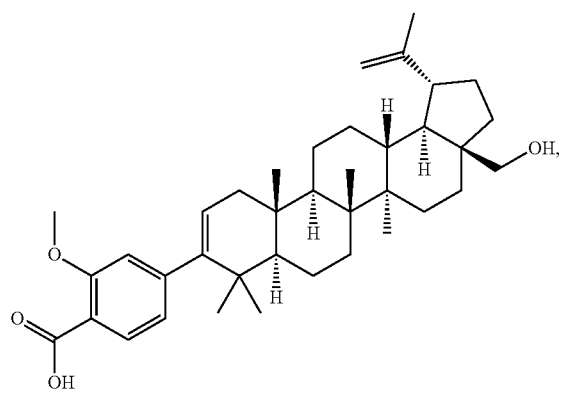
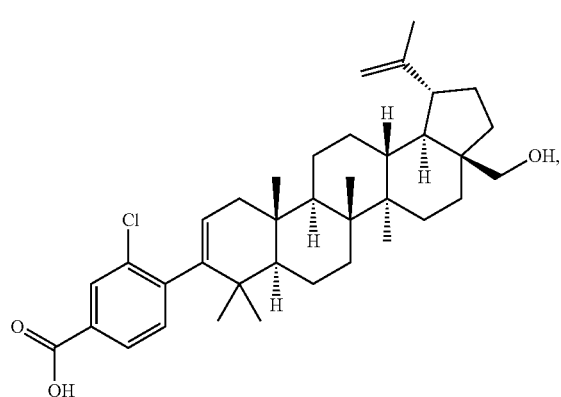
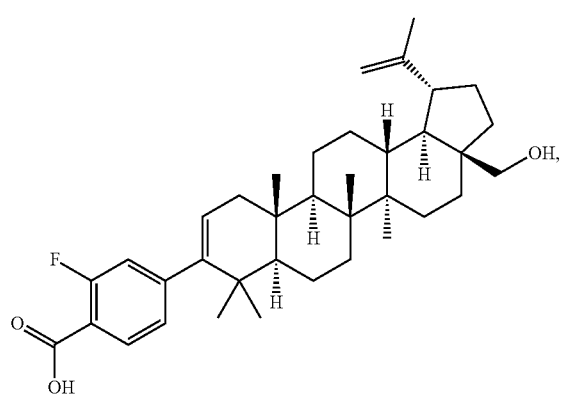
18
-continued
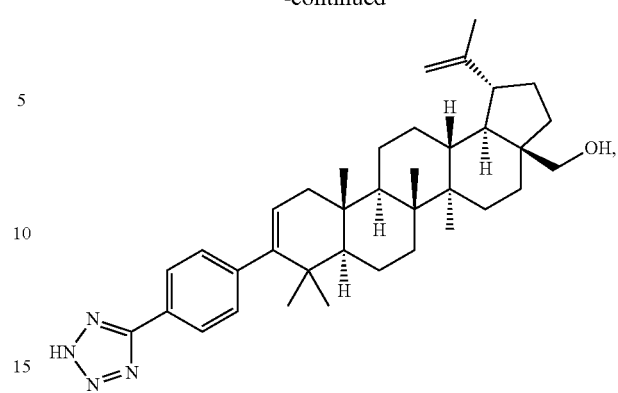
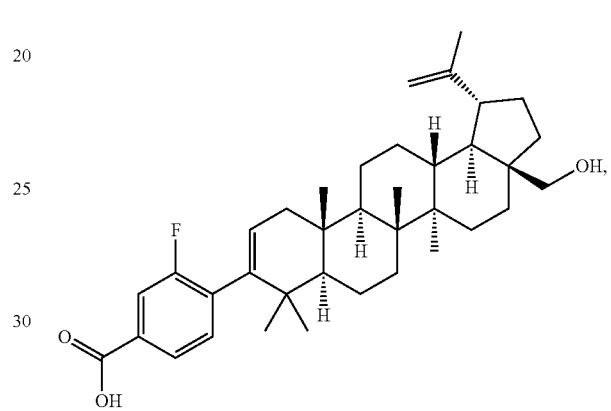
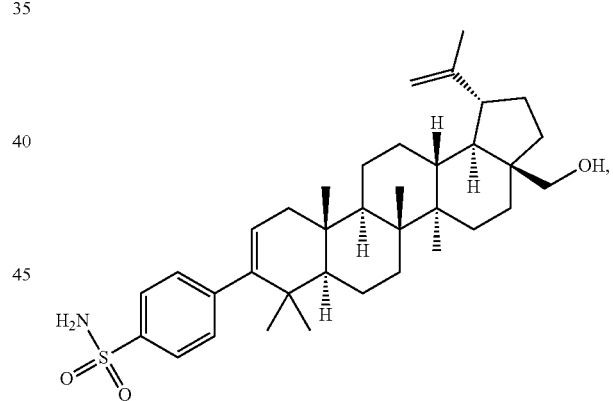
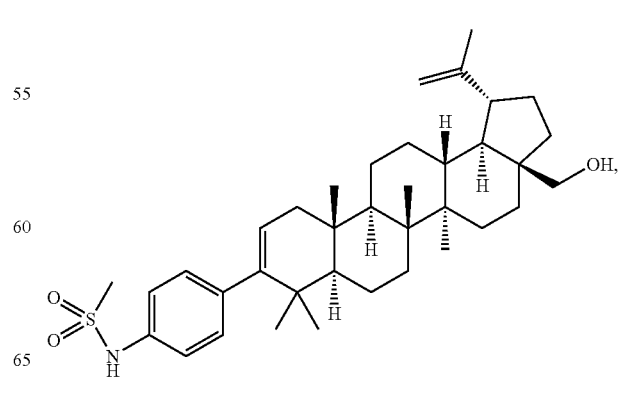

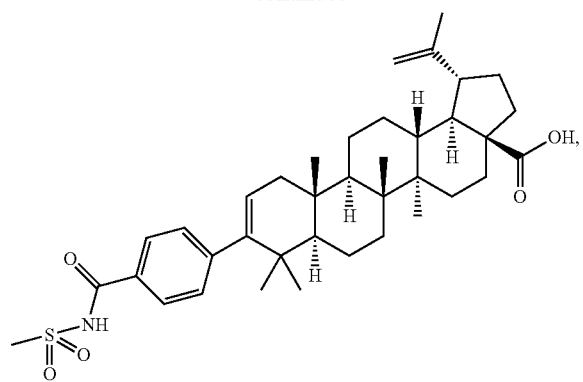
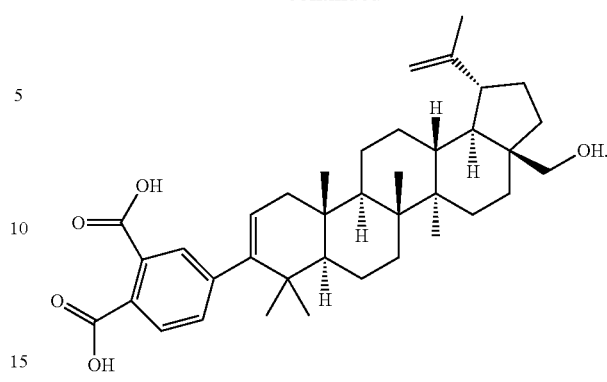
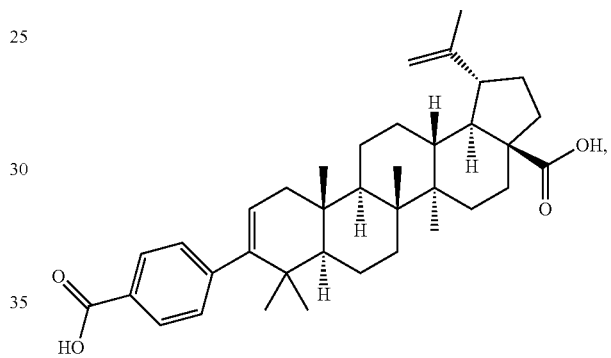
Of the foregoing, the following compounds are particularly preferred:
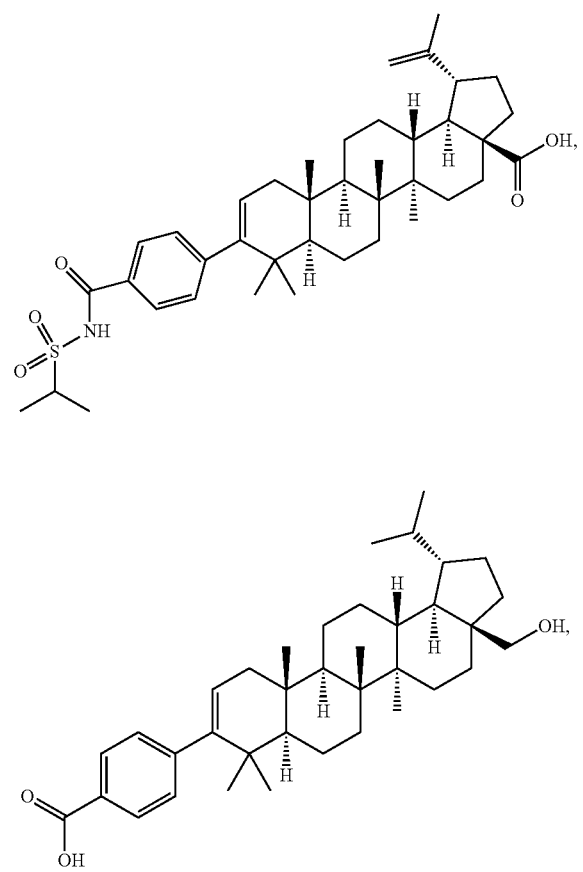
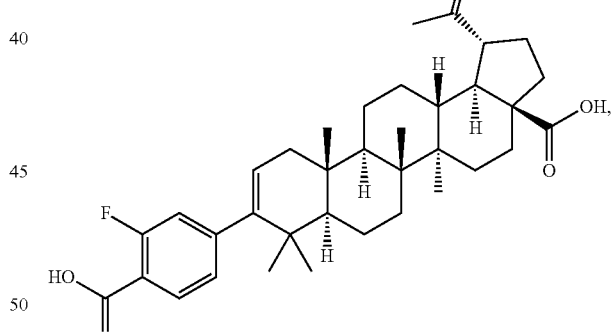
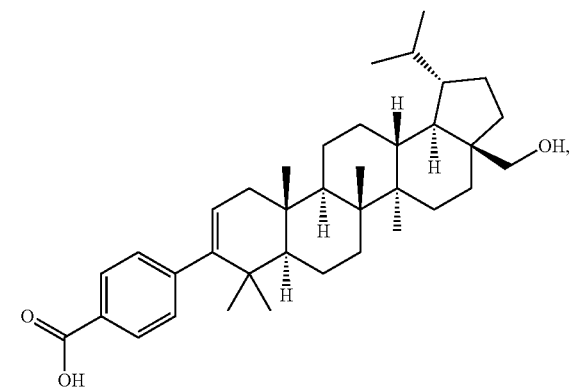
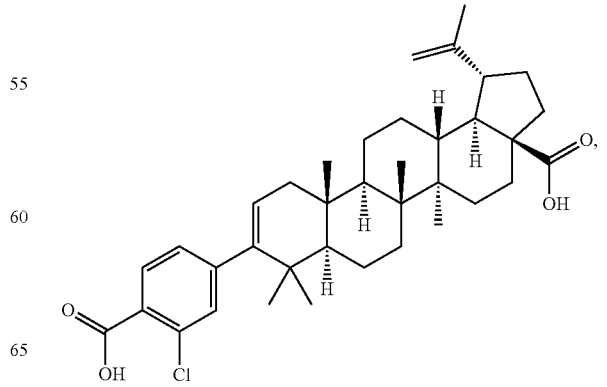
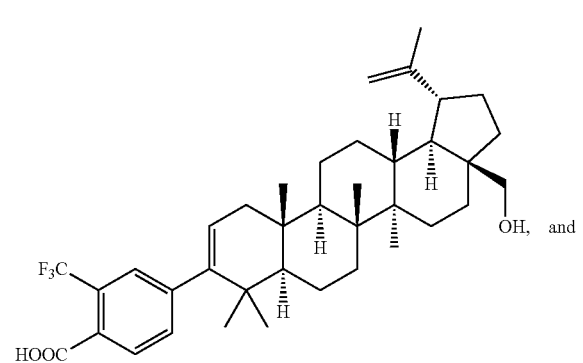

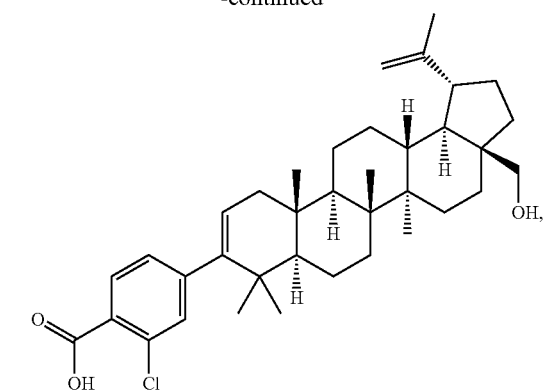

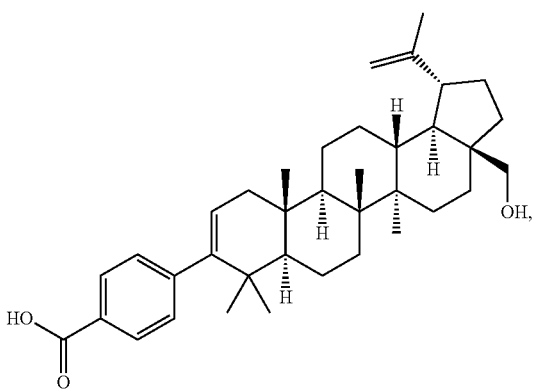

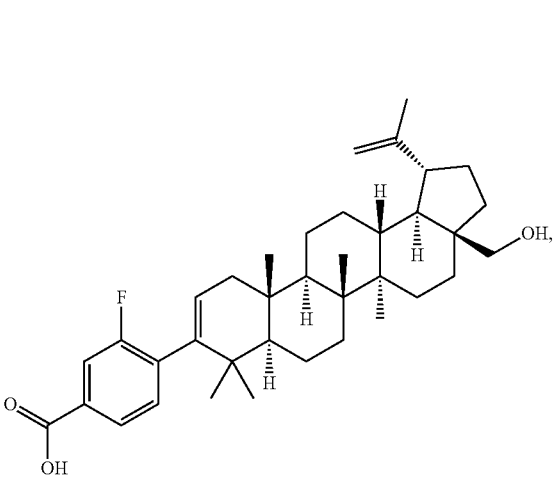

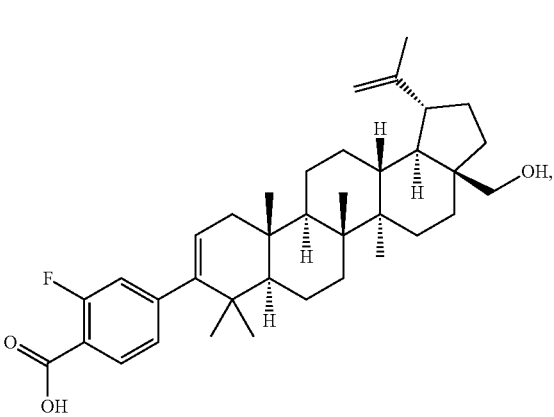

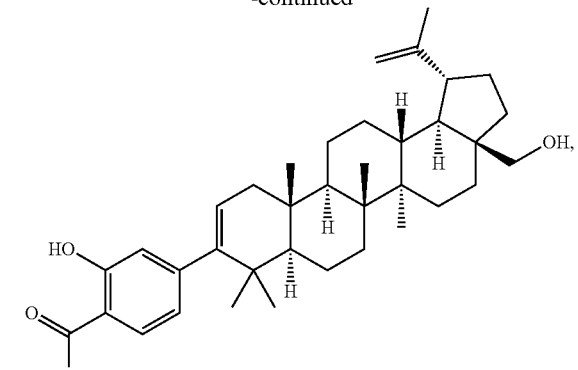

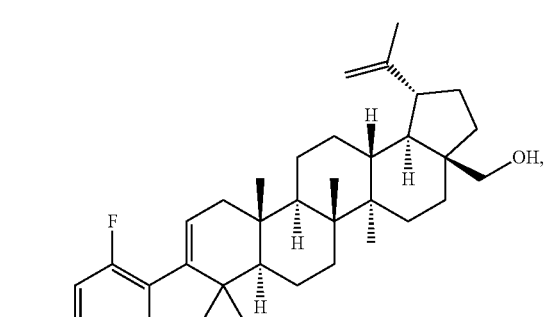

Also preferred as part of the invention are the compounds of Formula I wherein X is 5 or 6-membered heteroaryl ring. In particular, the compounds of Formula I wherein X is a 5-membered heteroaryl ring having the following structure are particularly preferred:

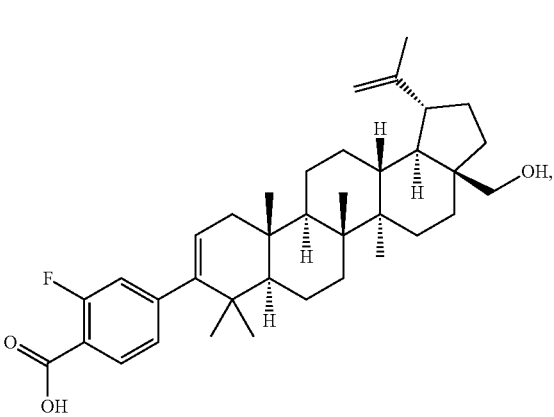

wherein each of U, V and W is selected from the group consisting of C, N, O and S, with the proviso that at least one of U, V and W is other than C. Of these, the compounds wherein X is selected from the group of thiophene, pyrazole, isoxazole, and oxadiazole groups are particularly preferred. Also preferred are the compounds of Formula I wherein X is a 6-membered heteroaryl ring selected from the group of pyridyl and pyrimidine rings.

Other compounds derived from Formula I (wherein X is a 5 or 6-membered heteroaryl ring) which are preferred as part of the invention include the following:

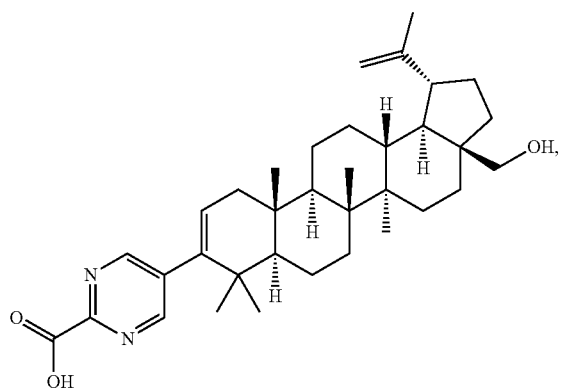

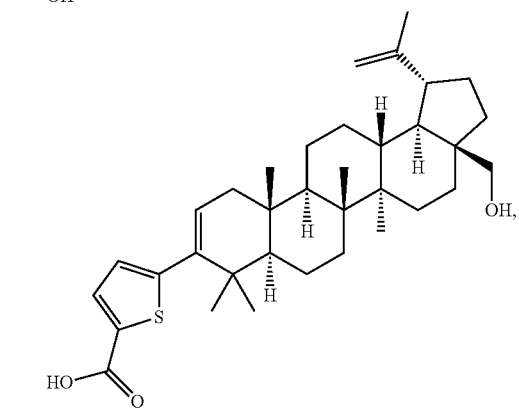

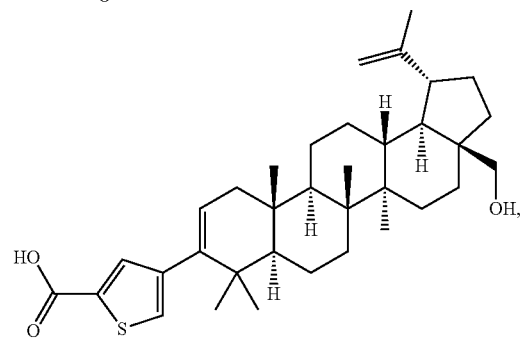

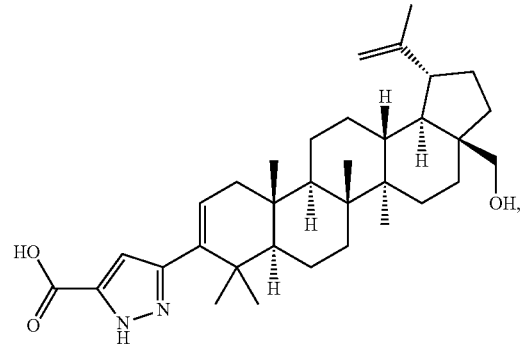

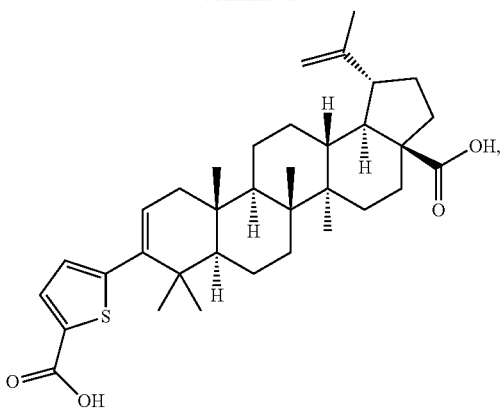

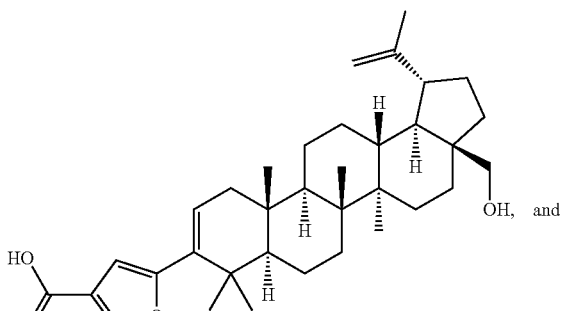

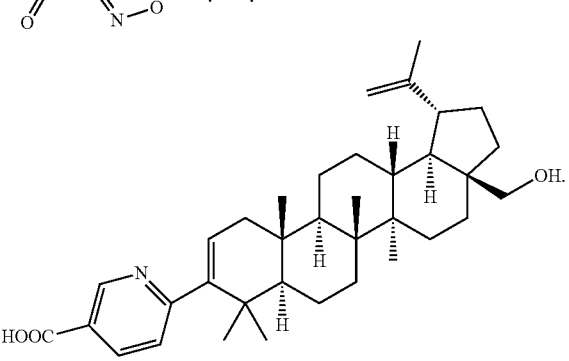

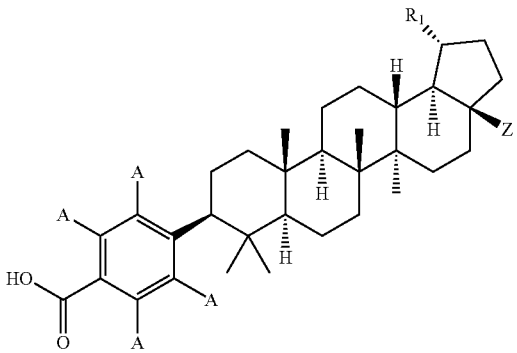

Other preferred compounds of the invention include those which are encompassed by Formula II as set forth above. Of these, the compounds wherein X is a phenyl group and Y is —COOH in the para position (and A is as previously set forth) according to Formula IIa below are particularly preferred:

Formula IIa

Other preferred compounds of Formula II include the following:

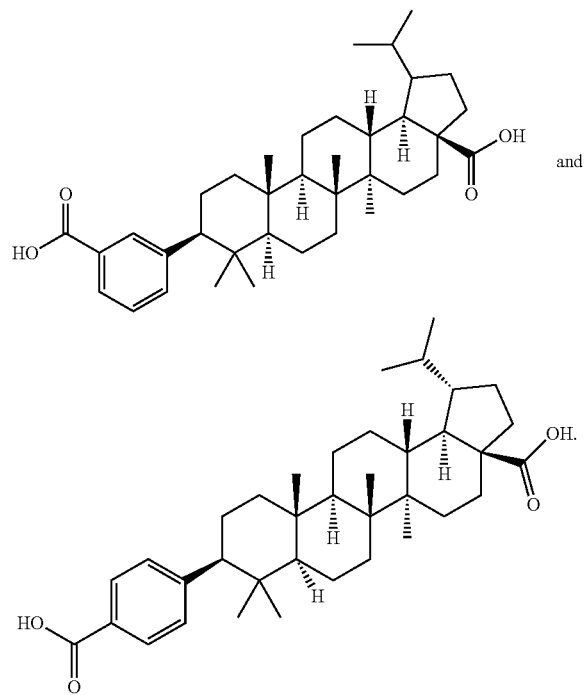

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II and/or III herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |

-continued

| Drug Name | Manufacturer | Indication |
|---|---|---|
| Amprenavir<br>141 W94<br>GW 141 | Glaxo Wellcome | HIV infection,<br>AIDS, ARC<br>(protease inhibitor) |
| Abacavir (1592U89)<br>GW 1592 | Glaxo Wellcome | HIV infection,<br>AIDS, ARC<br>(RT inhibitor) |
| Acemannan | Carrington Labs<br>(Irving, TX) | ARC |
| Acyclovir | Burroughs Wellcome | HIV infection, AIDS,<br>ARC |
| AD-439 | Tanox Biosystems | HIV infection, AIDS,<br>ARC |
| AD-519 | Tanox Biosystems | HIV infection, AIDS,<br>ARC |
| Adefovir dipivoxil | Gilead Sciences | HIV infection |
| AL-721 | Ethigen<br>(Los Angeles, CA) | ARC, PGL<br>HIV positive, AIDS |
| Alpha Interferon | Glaxo Wellcome | Kaposi's sarcoma,<br>HIV in combination<br>w/Retrovir |
| Ansamycin<br>LM 427 | Adria Laboratories<br>(Dublin, OH)<br>Erbamont<br>(Stamford, CT) | ARC |
| Antibody which<br>Neutralizes pH<br>Labile alpha aberrant<br>Interferon | Advanced Biotherapy<br>Concepts<br>(Rockville, MD) | AIDS, ARC |
| AR177 | Aronex Pharm | HIV infection, AIDS,<br>ARC |
| Beta-fluoro-ddA | Nat'l Cancer Institute | AIDS-associated<br>diseases |
| BMS-234475<br>(CGP-61755) | Bristol-Myers Squibb/<br>Novartis | HIV infection,<br>AIDS, ARC<br>(protease inhibitor) |
| CI-1012 | Warner-Lambert | HIV-1 infection |
| Cidofovir | Gilead Science | CMV retinitis,<br>herpes, papillomavirus |
| Curdlan sulfate | AJI Pharma USA | HIV infection |
| Cytomegalovirus<br>Immune globin | MedImmune | CMV retinitis |
| Cytovene<br>Ganciclovir | Syntex | Sight threatening<br>CMV<br>peripheral CMV<br>retinitis |
| Darunavir | Tibotec- J & J | HIV infection, AIDS, ARC<br>(protease inhibitor) |
| Delaviridine | Pharmacia-Upjohn | HIV infection,<br>AIDS, ARC<br>(RT inhibitor) |
| Dextran Sulfate | Ueno Fine Chem.<br>Ind. Ltd. (Osaka,<br>Japan) | AIDS, ARC, HIV<br>positive<br>asymptomatic |
| ddC<br>Dideoxycytidine | Hoffman-La Roche | HIV infection, AIDS,<br>ARC |
| ddI<br>Dideoxyinosine | Bristol-Myers Squibb | HIV infection, AIDS,<br>ARC; combination<br>with AZT/d4T |
| DMP-450 | AVID<br>(Camden, NJ) | HIV infection,<br>AIDS, ARC<br>(protease inhibitor) |
| Efavirenz<br>(DMP 266, Sustiva ®)<br>(-)6-Chloro-4-(S)-<br>cyclopropylethynyl-<br>4(S)-trifluoro-<br>methyl-1,4-dihydro-<br>2H-3,1-benzoxazin-<br>2-one, STOCRINE | Bristol Myers Squibb | HIV infection,<br>AIDS, ARC<br>(non-nucleoside RT<br>inhibitor) |
| EL10 | Elan Corp, PLC<br>(Gainesville, GA) | HIV infection |
| Etravirine | Tibotec/J & J | HIV infection, AIDS, ARC<br>(non-nucleoside<br>reverse transcriptase<br>inhibitor) |

-continued

| Drug Name | Manufacturer | Indication |
| --- | --- | --- |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |

-continued

| Drug Name | Manufacturer | Indication |
|---|---|---|
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Maraviroc SELZENTRY ®; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®)) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®)), EMTRIVA ® (Emtricitabine), and SUSTIVA ® (Efavirenz) |
| 4'-ethynyl-d4T | Bristol-Myers Squibb | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |

-continued

| Drug Name | Manufacturer | Indication |
|---|---|---|
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |

| Drug Name | Manufacturer | Indication |
| --- | --- | --- |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this disclosure with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

General Chemistry

Methods of Synthesis

The present invention comprises compounds of Formulas I, II and III, their pharmaceutical formulations, and their use in patients suffering from or susceptible to HIV infection. The compounds of Formulas I, II and III include pharmaceutically acceptable salts thereof. General procedures to construct compounds of Formulas I, II and III and intermediates useful for their synthesis are described in the following Schemes (after the Abbreviations).

ABBREVIATIONS

One or more of the following abbreviations, most of which are conventional abbreviations well known to those skilled in the art, may be used throughout the description of the disclosure and the examples:

h=hour(s)
min=minute(s)
rt=room temperature
mol=mole(s)
mmol=millimole(s)
g=gram(s)
mg=milligram(s)
mL=milliliter(s)
TFA=trifluoroacetic Acid
DCE=1,2-Dichloroethane
DMAP=4-dimethylaminopyridine
DMF=N,N-dimethylformamide
KHMDS=potassium hexamethyldisilazide
TMS=trimethylsilyl
DCM=dichloromethane
MeOH=methanol
THF=tetrahydrofuran
EtOAc=ethyl acetate
DME=dimethoxyethane
TLC=thin layer chromatography
DMSO=dimethylsulfoxide
PCC=pyridinium chlorochromate
ATM=atmosphere(s)
HOAc=acidic acid
TBAF=tetrabutylammonium fluoride
TBDPSCl=tertbutyldiphenylchlorosilane
Hex=hexane(s)

Preparation of Compounds of Formulas I, II and III General Chemistry Schemes:

Compounds of Formula I and II can be prepared from commercially available (Aldrich, others) betulinic acid and/or betulin, by chemistry described in the following schemes. General reaction schemes are set forth as follows:

Scheme 1

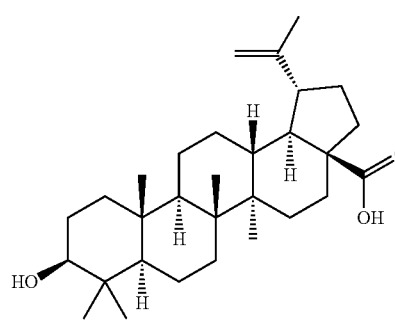

Betulinic acid

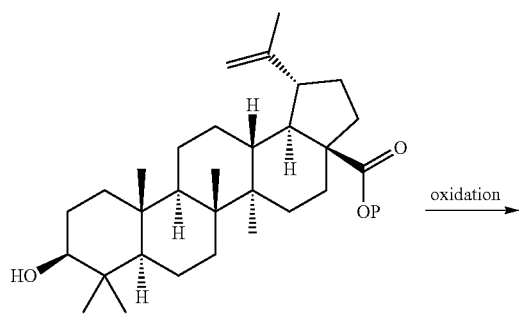

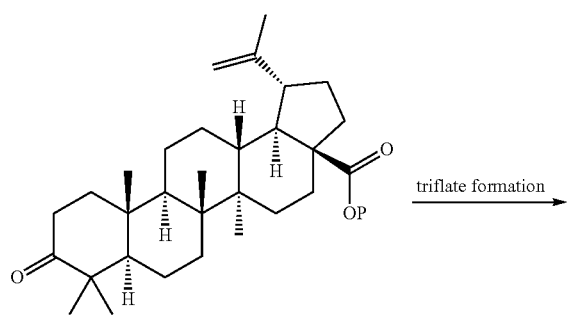

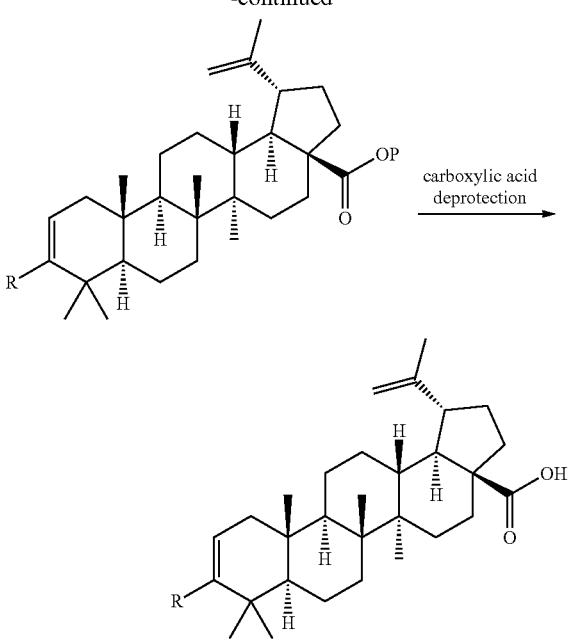

The carboxylic acid in the C-28 position can be protected with a suitable protective group. Standard oxidation (i.e. PCC, Dess-Martin, Swern) produces the C-3 ketone which is then converted into the triflate using methods available to those skilled in the art. Palladium catalyzed cross coupling with boronic acid or stannanes (standard Suzuki or Stille couplings) followed by deprotection of the carboxylic acid affords the C-3 modified betulinic acid derivatives. Compounds of Formula II derived from betulinic acid can be prepared by taking compounds of formula I with the C-28 acid and hydrogenating stepwise or in one single step the double bonds present in the molecule as shown in scheme 2.

Scheme 2

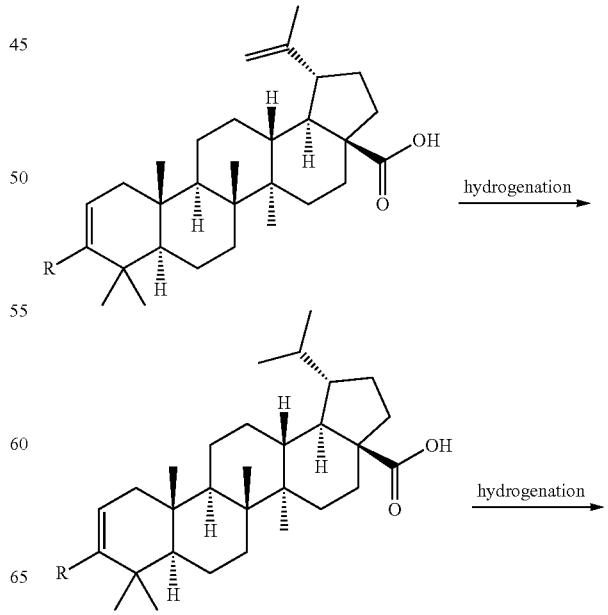

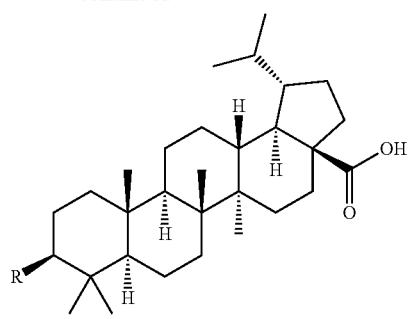
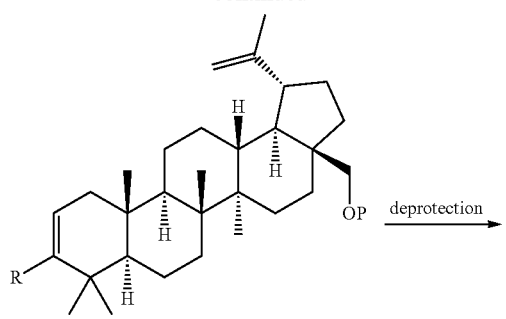

Scheme 3

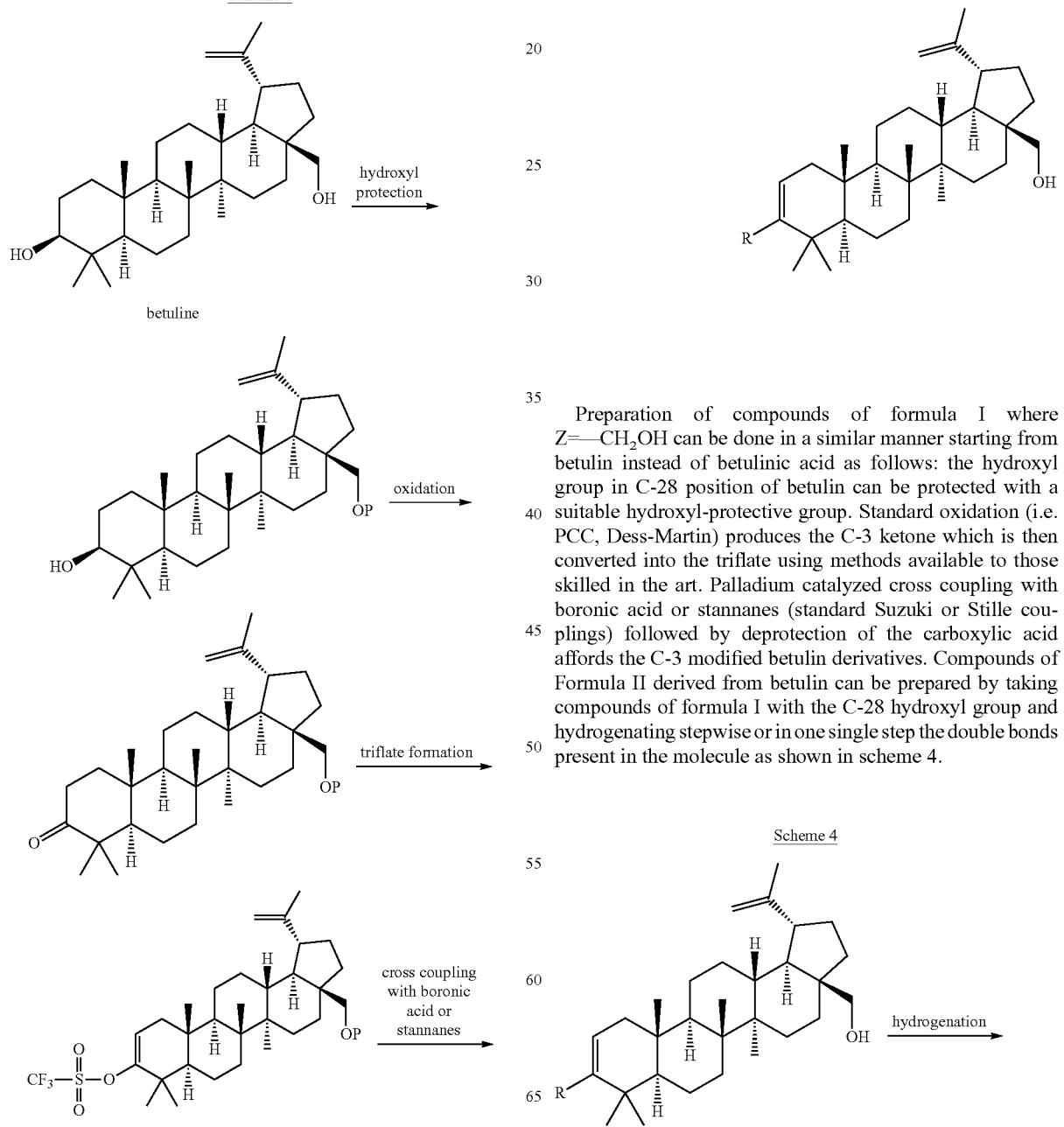

betuline

Preparation of compounds of formula I where Z=—CH₂OH can be done in a similar manner starting from betulin instead of betulinic acid as follows: the hydroxyl group in C-28 position of betulin can be protected with a suitable hydroxyl-protective group. Standard oxidation (i.e. PCC, Dess-Martin) produces the C-3 ketone which is then converted into the triflate using methods available to those skilled in the art. Palladium catalyzed cross coupling with boronic acid or stannanes (standard Suzuki or Stille couplings) followed by deprotection of the carboxylic acid affords the C-3 modified betulin derivatives. Compounds of Formula II derived from betulin can be prepared by taking compounds of formula I with the C-28 hydroxyl group and hydrogenating stepwise or in one single step the double bonds present in the molecule as shown in scheme 4.

Scheme 4

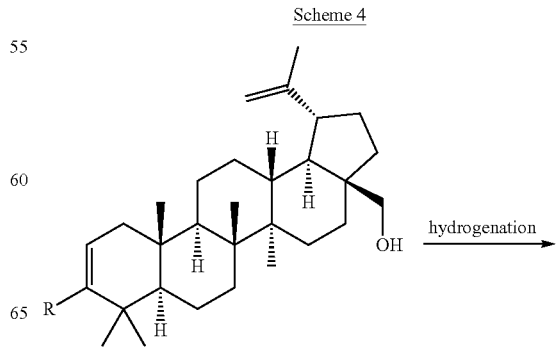

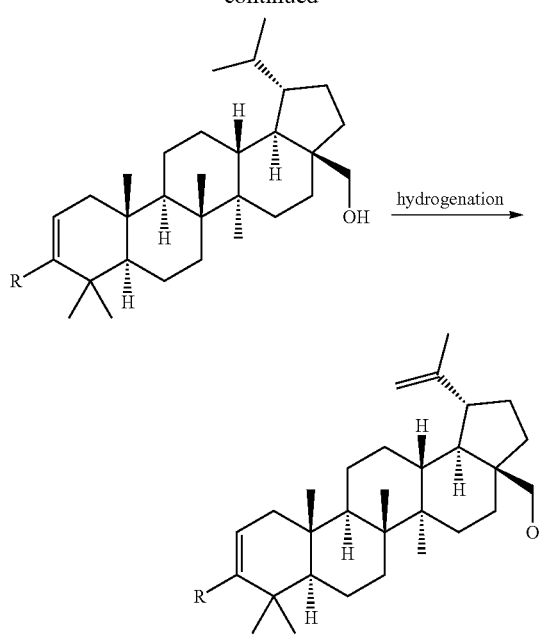

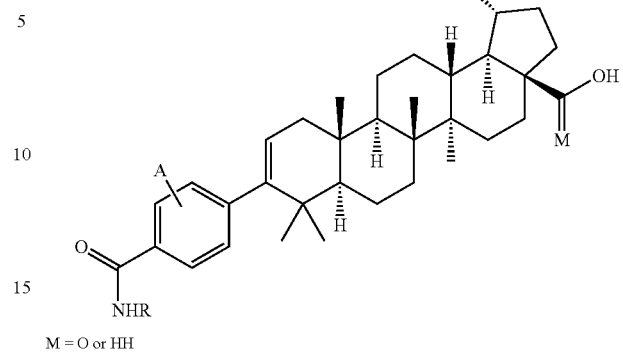

M = O or HH

Some compounds of Formula I containing a carboxylic acid in the substituent in the C-3 position of the core can be further derivatized by converting the carboxylic acid in an acid chloride followed by addition of an amine. Deprotection of the C-28 acid or carboxylic acid produces the final compounds.

The same synthetic methods can be applied to prepare compounds of Formula III using ursolic acid, oleanoic acid or moronic acid (oxidation is not necessary in this case, since the C-3 ketone is already present) as starting material instead of betulinic acid or betulin as shown, for example, in the following scheme:

Scheme 5

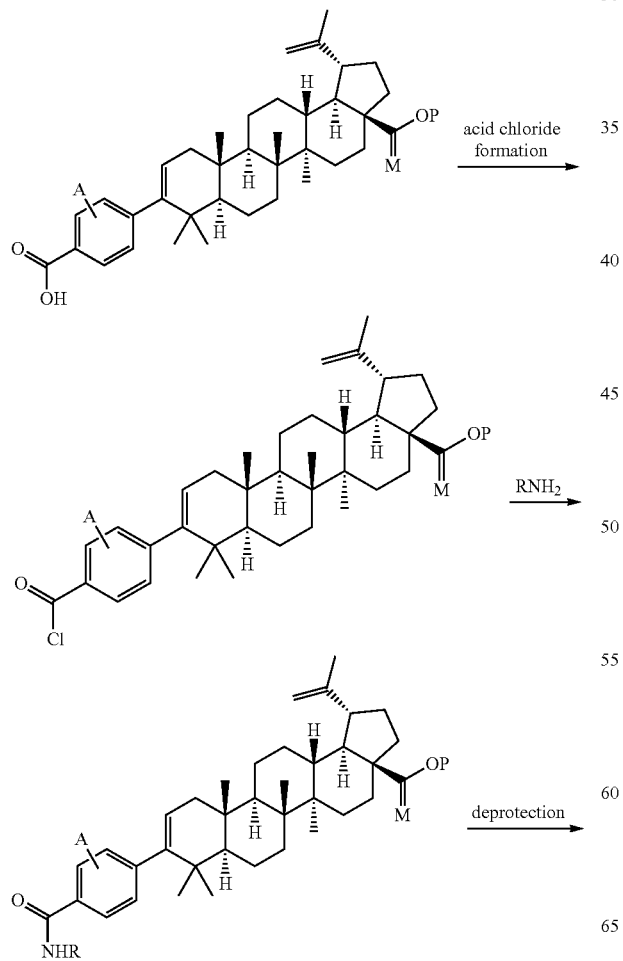

Scheme 6

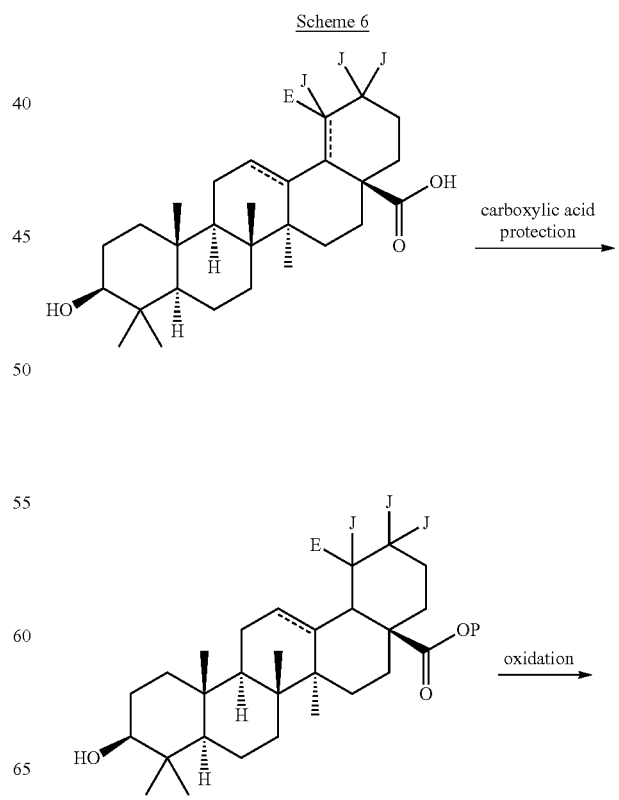

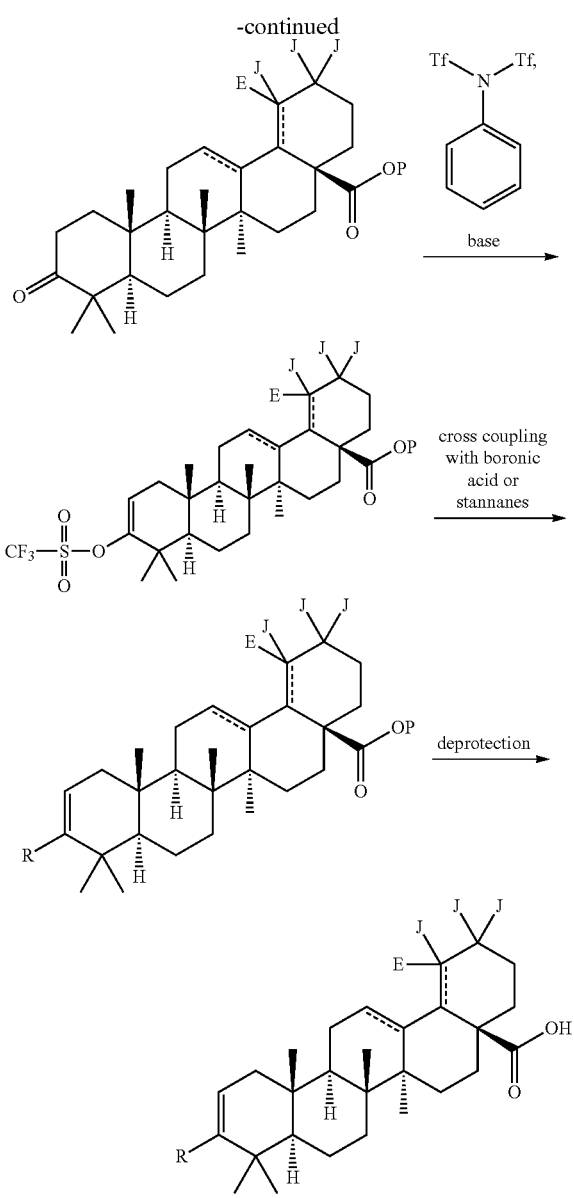

EXAMPLES

The following examples illustrate typical syntheses of the compounds of Formulas I, II and III as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), Acetic-d$_4$ (Acetic Acid d$_4$) ($\delta_H$ 11.6, 2.07), DMSOmix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods

Method 1
Start % B=0, Final % B=100 over 2 minute gradient
Flow Rate=4 mL/Min
Solvent A=95% Water/5% Acetonitrile/10 mM Ammonium Acetate
Solvent B=5% Water/95% Acetonitrile/10 mM Ammonium Acetate
Column =PHENOMENEX-LUNA 3.0×50 mm S10

Method 2
Start % B=30, Final % B=95 over 5 minute gradient
Flow Rate=2 mL/Min
Solvent A=100% Water/10 mM Ammonium Acetate
Solvent B=100% Acetonitrile/10 mM Ammonium Acetate
Column=Supelco Acentis 4.6×50 mm 2.7 um C18

Method 3
Start % B=30, Final % B=95 over 6 minute gradient
Flow Rate=1.5 mL/Min
Solvent A=100% Water/10 mM Ammonium Acetate
Solvent B=100% Acetonitrile/10 mM Ammonium Acetate
Column=Supelco Acentis 4.6×50 mm 2.7 um C18

Method 4
Start % B=30, Final % B=95 over 6 minute gradient
Flow Rate=2 mL/Min
Solvent A=100% Water/10 mM Ammonium Acetate
Solvent B=100% Acetonitrile/10 mM Ammonium Acetate
Column=Supelco Acentis 4.6×50 mm 2.7 um C18

Method 5
Start % B=0, Final % B=100 over 4 minute gradient
Flow Rate=4 mL/Min
Solvent A=95% Water/5% Acetonitrile/10 mM Ammonium Acetate
Solvent B=5% Water/95% Acetonitrile/10 mM Ammonium Acetate
Column=LUNA 3.0×50 mm S10

Method 6
Start % B=10, Final % B=95 over 7 minute gradient
Flow Rate=2 mL/Min
Solvent A=100% Water/10 mM Ammonium Acetate
Solvent B=100% Acetonitrile
Column=Ascentis C-18, 4.6×50 mm 2.7 um Method 7
Start % B=0, Final % B=100 over 2 minute gradient
Flow Rate=4 mL/Min
Solvent A=95% Water/5% Methanol/10 mM Ammonium Acetate
Solvent B=5% Water/95% Methanol/10 mM Ammonium Acetate
Column=PHENOMENEX-LUNA 3.0×50 mm S10

Method 8
Start % B=20, Final % B=95 over 12 minute gradient
Flow Rate=1 mL/Min
Solvent A=100% Water/10 mM Ammonium Acetate
Solvent B=100% Methanol/10 mM Ammonium Acetate
Column=PHENOMENEX-LUNA 4.6×150 mm 5 um C5

Method 9
Start % B=70, Final % B=95 over 5 minute gradient
Flow Rate=1.2 mL/Min
Solvent A=100% Water/10 mM Ammonium Acetate
Solvent B=100% Methanol/10 mM Ammonium Acetate
Column=Waters Xbridge 4.6×50 mm 5 um C18

Preparation of Compounds

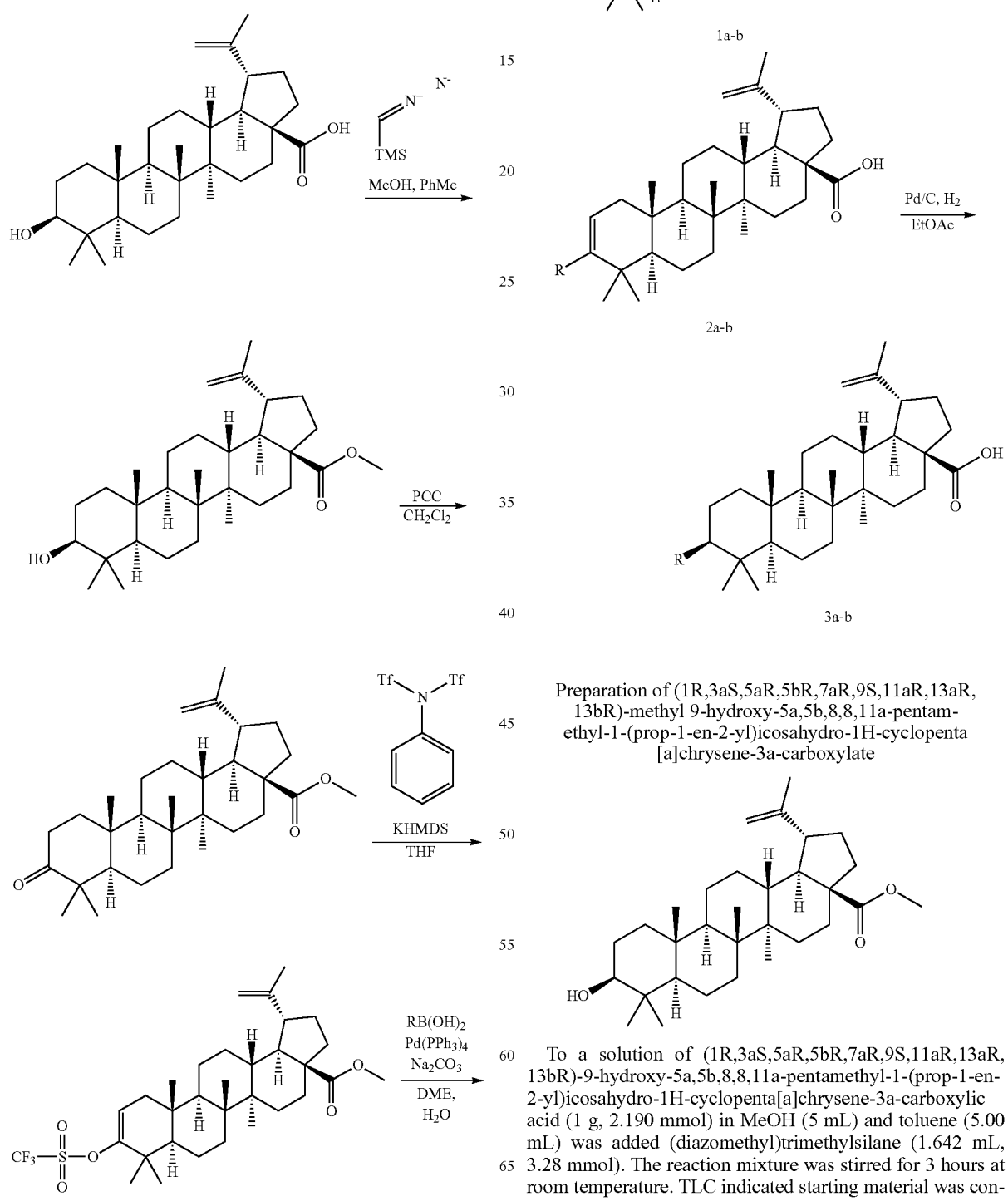

Preparation of (1R,3aS,5aR,5bR,7aR,9S,11aR,13aR, 13bR)-methyl 9-hydroxy-5a,5b,8,8,11a-pentamethyl-1-(prop-1-en-2-yl)icosahydro-1H-cyclopenta[a]chrysene-3a-carboxylate To a solution of (1R,3aS,5aR,5bR,7aR,9S,11aR,13aR, 13bR)-9-hydroxy-5a,5b,8,8,11a-pentamethyl-1-(prop-1-en-2-yl)icosahydro-1H-cyclopenta[a]chrysene-3a-carboxylic acid (1 g, 2.190 mmol) in MeOH (5 mL) and toluene (5.00 mL) was added (diazomethyl)trimethylsilane (1.642 mL, 3.28 mmol). The reaction mixture was stirred for 3 hours at room temperature. TLC indicated starting material was consumed and a new product was formed. The reaction mixture was concentrated under reduced pressure to give the desired product (1R,3aS,5aR,5bR,7aR,9S,11aR,13aR,13bR)-methyl 9-hydroxy-5a,5b,8,8,11a-pentamethyl-1-(prop-1-en-2-yl) icosahydro-1H-cyclopenta[a]chrysene-3a-carboxylate as a white solid (1 g, 97%). $^1$H NMR (500 MHz, DMSO-D6) δ ppm 0.65 (s, 3H), 0.76 (s, 3H), 0.87 (d, J=12.67 Hz, 6H), 0.94 (s, 3H), 0.96-1.63 (m, 18H), 1.65 (s, 3H), 1.72-1.87 (m, 2H), 2.03-2.16 (m, 2H), 2.85-3.09 (m, 3H), 3.60 (s, 3H), 4.26 (d, J=4.58 Hz, 1H), 4.58 (s, 1H), 4.70 (d, J=1.83 Hz, 1H).

Preparation of (1R,3aS,5aR,5bR,7aR,11aR,13aR,13bR)-methyl 5a,5b,8,8,11a-pentamethyl-9-oxo-1-(prop-1-en-2-yl)icosahydro-1H-cyclopenta[a]chrysene-3a-carboxylate

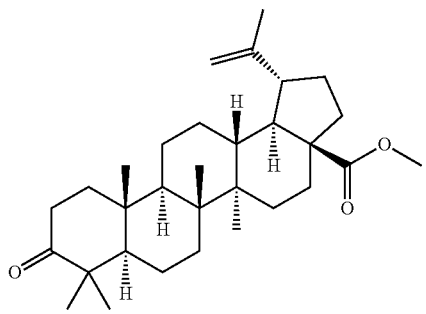

To a solution of (1R,3aS,5aR,5bR,7aR,9S,11aR,13aR,13bR)-methyl 9-hydroxy-5a,5b,8,8,11a-pentamethyl-1-(prop-1-en-2-yl)icosahydro-1H-cyclopenta[a]chrysene-3a-carboxylate (4 g, 8.50 mmol) in CH$_2$Cl$_2$ (100 mL) was added PCC (5.50 g, 25.5 mmol). The reaction mixture was stirred for 15 hours at room temperature. TLC indicated starting material was consumed and a new compound was generated. The reaction mixture was concentrated under reduced pressure and the residue was purified by biotage using ethyl acetate/hexanes (0-20%) to give the desired product (1R,3aS,5aR,5bR,7aR,11aR,13aR,13bR)-methyl 5a,5b,8,8,11a-pentamethyl-9-oxo-1-(prop-1-en-2-yl)icosahydro-1H-cyclopenta[a]chrysene-3a-carboxylate as a white solid (4 g, 100%). $^1$H NMR (500 MHz, DMSO-D6) δ ppm 0.85 (s, 3H), 0.88 (s, 3H), 0.93 (s, 3H), 0.95 (s, 3H), 0.98 (s, 3H), 1.00-1.64 (m, 17H), 1.65 (s, 3H), 1.73-1.84 (m, 3H), 2.07-2.23 (m, 2H), 2.28-2.39 (m, 1H), 2.39-2.48 (m, 1H), 2.86-3.00 (m, 1H), 3.56-3.63 (s, 3H), 4.58 (s, 1H), 4.71 (d, J=1.83 Hz, 1H).

Preparation of (1R,3aS,5aR,5bR,7aR,11aR,13aR,13bR)-methyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate

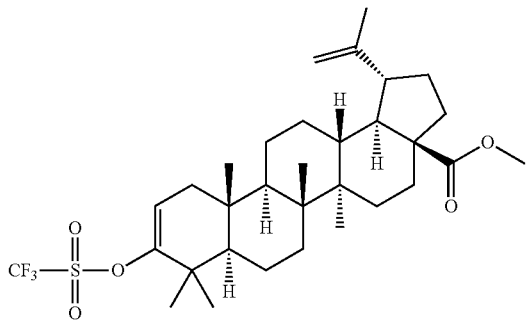

To a solution of (1R,3aS,5aR,5bR,7aR,11aR,13aR,13bR)-methyl 5a,5b,8,8,11a-pentamethyl-9-oxo-1-(prop-1-en-2-yl) icosahydro-1H-cyclopenta[a]chrysene-3a-carboxylate (2 g, 4.27 mmol) and 1,1,1-trifluoro-N-phenyl-N-(trifluoromethylsulfonyl)methanesulfonamide (3.05 g, 8.53 mmol) in THF (30 mL) at −78° C. was slowly added KHMDS (0.5 M in Toluene) (17.07 mL, 8.53 mmol). The reaction mixture was stirred for 1 hour at −78° C. TLC indicated starting material was consumed and one new compound was generated. The reaction mixture was quenched with brine, and extracted with diethyl ether. The combined organic layer was dried over Na$_2$SO$_4$, filtered and concentrated under reduced pressure. The residue was dissolved in toluene and purified by biotage using ethyl acetate/hexanes (0-5%) to provide (1R,3aS,5aR,5bR,7aR,11aR,13aR,13bR)-methyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate as a white solid (1.8 g, 70%). $^1$H NMR (400 MHz, CHLOROFORM-D) δ ppm 0.92 (s, 3H), 0.97 (d, J=7.78 Hz, 3H), 1.01-1.05 (m, 6H), 1.13 (s, 3H), 1.15-1.67 (m, 15H), 1.68-1.82 (m, 5H), 1.84-1.98 (m, 2H), 2.17 (dd, J=17.07, 6.78 Hz, 1H), 2.22-2.34 (m, 2H), 2.88-3.12 (m, 1H), 3.69 (s, 3H), 4.62 (s, 1H), 4.75 (s, 1H), 5.57 (dd, J=6.78, 1.76 Hz, 1H).

General Procedure for Preparation of Examples 1a-b

Example 1a

Preparation of 3-((1R,3aS,5aR,5bR,7aR,11aS,13aR,13bR)-3a-(methoxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

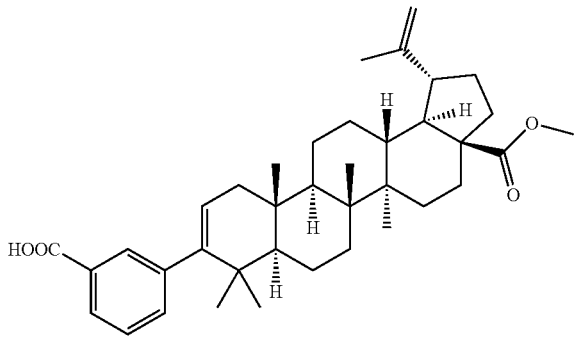

A mixture of (1R,3aS,5aR,5bR,7aR,11aR,13aR,13bR)-methyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (240 mg, 0.399 mmol), 3-boronobenzoic acid (133 mg, 0.799 mmol), sodium carbonate (212 mg, 1.997 mmol) and Pd(Ph$_3$P)$_4$ (46.2 mg, 0.040 mmol) in DME (2.000 ml) and water (2 ml) was heated to 100° C. for 3 hours. TLC and LCMS indicated starting material was consumed, and the desired product was formed. The reaction mixture was cooled to room temperature, neutralized with 1N HCl, extracted with ethyl acetate, dried over sodium sulfate, filtered and concentrated under reduced pressure. The residue was purified by biotage using ethyl acetate/hexanes (0-100%) ethyl acetate/hexanes to give the desired product 3-((1R,3aS,5aR,5bR,7aR,11aS,13aR,13bR)-3a-(methoxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid as a white solid (120 mg, 50%). LCMS: m/e 571.47 (M−H)$^-$, 3.91 min (method 5). $^1$H NMR (500 MHz, DMSO-D6) δ ppm 0.88 (d, J=5.19 Hz, 6H), 0.92 (s, 3H), 0.95 (s, 3H), 0.98 (s, 3H), 1.00-1.56 (m, 15H), 1.57-1.73 (m, 5H), 1.73-1.86 (m, 2H), 2.07 (dd, J=17.24, 6.26 Hz, 1H), 2.11-2.17 (m, 1H), 2.18-2.28 (m, 1H), 2.85-3.03 (m, 1H), 3.61 (s, 3H), 4.59 (s, 1H), 4.72 (d, J=1.83 Hz, 1H), 5.25 (d, J=4.58 Hz, 1H), 7.33 (d, J=7.32 Hz, 1H), 7.40 (t, J=7.63 Hz, 1H), 7.65 (s, 1H), 7.82 (d, J=7.93 Hz, 1H).

Example 1b

Preparation of 4-((1R,3aS,5aR,5bR,7aR,11aS,13aR,13bR)-3a-(methoxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

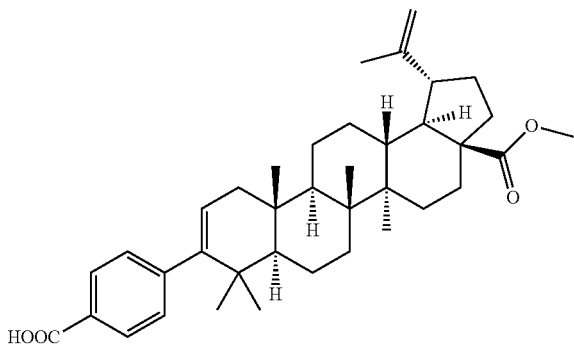

The title compound was prepared following the method described above for compound 3-((1R,3aS,5aR,5bR,7aR,11aS,13aR,13bR)-3a-(methoxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (example 1a) using 4-boronobenzoic acid as the reactant boronic acid. The product was isolated as a white solid (60 mg, 26%). LCMS: m/e 571.47 (M−H)$^-$, 8.27 min (method 6). $^1$H NMR (500 MHz, DMSO-d$_6$) δ ppm 0.89 (s, 6H), 0.92 (s, 3H), 0.94 (s, 3H), 0.98 (s, 3H), 1.00-1.72 (m, 17H), 1.67 (s, 3H), 1.74-1.86 (m, 2H), 2.03-2.11 (m, 1H), 2.11-2.17 (m, 1H), 2.17-2.28 (m, 1H), 2.89-3.02 (m, 1H), 3.61 (s, 3H), 4.59 (s, 1H), 4.72 (d, J=2.14 Hz, 1H), 5.24 (dd, J=6.10, 1.53 Hz, 1H), 7.21 (d, J=8.24 Hz, 2H), 7.86 (d, J=8.55 Hz, 2H).

General Procedure for Preparation of Example 2a-b

Example 2a

Preparation of (1R,3aS,5aR,5bR,7aR,11aS,13aR,13bR)-9-(3-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid

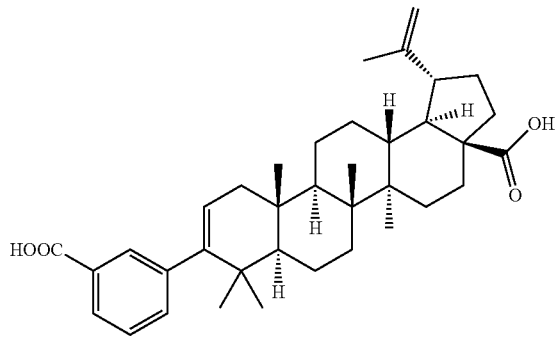

A mixture of 3-((1R,3aS,5aR,5bR,7aR,11aS,13aR,13bR)-3a-(methoxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid (140 mg, 0.244 mmol) and lithium bromide (425 mg, 4.89 mmol) in DMF (2 mL) was heated to 100° C. for 2 days. TLC indicated starting material was consumed and desired product was observed. The reaction mixture was filtered and the clear solution was purified by HPLC to provide the desired product (1R,3aS,5aR,5bR,7aR,11aS,13aR,13bR)-9-(3-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid as a white solid (25 mg, 17%). LCMS: m/e 557.48 (M−H)$^-$, 5.67 min (method 6). $^1$H NMR (400 MHz, DMSO-d$_6$) δ ppm 0.89 (s, 3H), 0.91 (s, 3H), 0.96 (s, 3H), 0.98 (s, 3H), 1.00 (s, 3H), 1.01-1.76 (m, 17H), 1.68 (s, 3H), 1.79-1.89 (m, 2H), 2.04-2.19 (m, 2H), 2.27-2.32 (m, 1H), 2.93-3.05 (m, 1H), 4.59 (s, 1H), 4.73 (d, J=2.01 Hz, 1H), 5.26 (d, J=4.77 Hz, 1H), 7.29-7.35 (m, 1H), 7.40 (t, J=7.65 Hz, 1H), 7.66 (s, 1H), 7.83 (d, J=7.53 Hz, 1H).

Example 2b

Preparation of (1R,3aS,5aR,5bR,7aR,11aS,13aR,13bR)-9-(4-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid

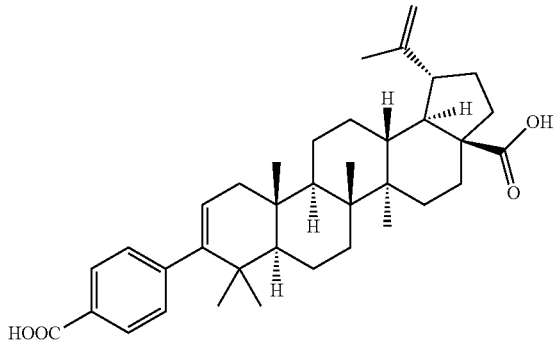

The title compound was prepared following the method described above for compound (1R,3aS,5aR,5bR,7aR,11aS,13aR,13bR)-9-(3-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (example 2a). The product was isolated as a white solid (40 mg, 19%). LCMS: m/e 557.46 (M−H)$^-$, 5.44 min (method 6). $^1$H NMR (500 MHz, DMSO-d$_6$) δ ppm 0.88 (s, 3H), 0.89 (s, 3H), 0.94 (s, 6H), 0.98 (s, 3H), 0.99-1.72 (m, 17H), 1.66 (s, 3H), 1.77-1.88 (m, 2H), 2.01-2.17 (m, 2H), 2.24-2.34 (m, 1H), 2.92-3.04 (m, 1H), 4.58 (s, 1H), 4.71 (d, J=2.14 Hz, 1H), 5.22 (d, J=4.58 Hz, 1H), 7.13 (d, J=7.93 Hz, 2H), 7.81 (d, J=8.24 Hz, 2H).

General Procedure for Preparation of Examples 3a-b

Example 3a

Preparation of (3aS,5aR,5bR,7aS,9S,11aS,13aR,13bR)-9-(3-carboxyphenyl)-1-isopropyl-5a,5b,8,8,11a-pentamethylicosahydro-1H-cyclopenta[a]chrysene-3a-carboxylic acid

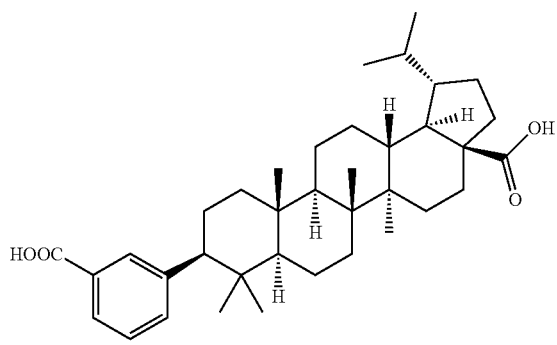

To a solution of (1R,3aS,5aR,5bR,7aR,11aS,13aR,13bR)-9-(3-carboxyphenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (20 mg, 0.036 mmol) in EtOAc (3 mL) was added 10% Pd/C (4 mg, 0.0036 mmol). The reaction mixture was stirred at room temperature under 1 ATM of $H_2$ for 36 h. LCMS indicated the reaction was complete and the desired product was formed. The reaction mixture was filtered through a celite pad which was washed with ethyl acetate. The filtrate was concentrated under reduced pressure to provide (3aS,5aR,5bR,7aS,9S,11aS,13aR,13bR)-9-(3-carboxyphenyl)-1-isopropyl-5a,5b,8,8,11a-pentamethylicosahydro-1H-cyclopenta[a]chrysene-3a-carboxylic acid as a white solid (8 mg, 38%). LCMS: m/e 561.45 (M–H)⁻, 3.53 min (method 5). $^1$H NMR (500 MHz, DMSO-$d_6$) δ ppm 0.64 (s, 3H), 0.71 (s, 3H), 0.74 (d, J=6.71 Hz, 3H), 0.80-0.86 (m, 3H), 0.92 (s, 3H), 0.93 (s, 3H), 0.95-0.98 (m, 3H), 0.98-1.66 (m, 18H), 1.68-1.82 (m, 3H), 2.07-2.22 (m, 3H), 2.23-2.34 (m, 1H), 2.42 (dd, J=13.12, 2.75 Hz, 1H), 7.36 (t, J=7.48 Hz, 1H), 7.39-7.46 (m, 1H), 7.70-7.80 (m, 2H).

Example 3b

Preparation of (1S,3aS,5aR,5bR,7aS,9S,11aS,11bR,13aR,13bR)-9-(4-carboxyphenyl)-1-isopropyl-5a,5b,8,8,11a-pentamethylicosahydro-1H-cyclopenta[a]chrysene-3a-carboxylic acid

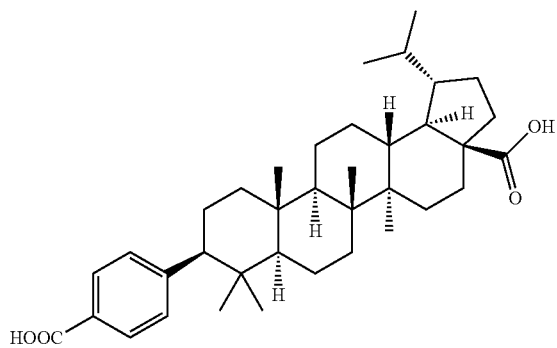

The title compound was prepared following the method described above for compound (3aS,5aR,5bR,7aS,9S,11aS,13aR,13bR)-9-(3-carboxyphenyl)-1-isopropyl-5a,5b,8,8,11a-pentamethylicosahydro-1H-cyclopenta[a]chrysene-3a-carboxylic acid (example 3a). The product was isolated as a white solid (2.2 mg, 9%). LCMS: m/e 561.59 (M–H)⁻, 5.60 min (method 2). $^1$H NMR (599 MHz, DMSO_CDCl$_3$) δ ppm 0.71 (s, 3H), 0.77 (s, 3H), 0.79 (d, J=7.03 Hz, 3H), 0.88 (d, J=6.44 Hz, 3H), 0.97 (s, 3H), 0.98 (s, 3H), 1.01 (s, 3H), 1.02-1.87 (m, 21H), 2.11-2.26 (m, 3H), 2.29-2.39 (m, 1H), 2.42-2.50 (m, 1H), 7.31 (d, J=7.62 Hz, 2H), 7.87 (d, J=7.62 Hz, 2H).

Intermediate 1: Preparation of (1R,3aS,5aR,5bR,7aR,9S,11aR,11bR,13aR,13bR)-benzyl 9-hydroxy-5a,5b,8,8,11a-pentamethyl-1-(prop-1-en-2-yl)icosahydro-1H-cyclopenta[a]chrysene-3a-carboxylate

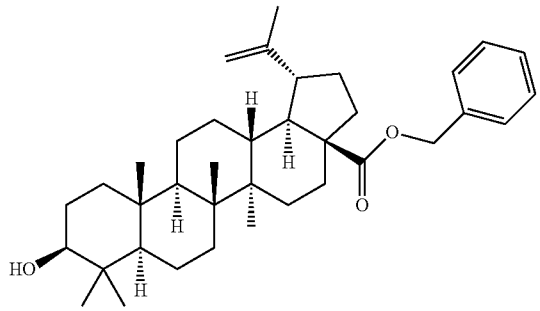

To a suspension of betulinic acid (12 g, 26.3 mmol) and potassium carbonate (7.26 g, 52.6 mmol) in DMF (150 mL) was added benzyl bromide (3.28 mL, 27.6 mmol). The mixture was heated to 60° C. for 3.5 h, and was cooled to rt. Solids started to precipitate upon cooling. The mixture was diluted with 200 mL of water and the solids that formed were collected by filtration to give (1R,3aS,5aR,5bR,7aR,9S,11aR,11bR,13aR,13bR)-benzyl 9-hydroxy-5a,5b,8,8,11a-pentamethyl-1-(prop-1-en-2-yl)icosahydro-1H-cyclopenta[a]chrysene-3a-carboxylate (13.92 g, 25.5 mmol, 97% yield) as a white solid. $^1$H NMR (500 MHz, CHLOROFORM-d) δ ppm 0.74 (s, 3H), 0.75 (s, 3H), 0.79 (s, 3H), 0.82-1.71 (m, 20H), 0.93 (s, 3H), 0.95 (s, 3H), 1.67 (s, 3H), 1.81-1.93 (m, 2H), 2.13-2.21 (m, 1H), 2.27 (ddd, J=12.36, 3.20, 3.05 Hz, 1H), 3.01 (td, J=10.99, 4.88 Hz, 1H), 3.17 (ddd, J=11.44, 5.65, 5.49 Hz, 1H), 4.59 (s, 1H), 4.71 (d, J=1.83 Hz, 1H), 5.06-5.16 (m, 2H), 7.28-7.39 (m, 5H).

Intermediate 2: Preparation of (1R,3aS,5aR,5bR,7aR,11aR,11bR,13aR,13bR)-benzyl 5a,5b,8,8,11a-pentamethyl-9-oxo-1-(prop-1-en-2-yl)icosahydro-1H-cyclopenta[a]chrysene-3a-carboxylate

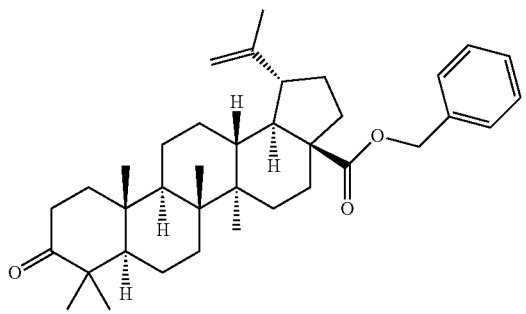

To a solution of (1R,3aS,5aR,5bR,7aR,9S,11aR,11bR,13aR,13bR)-benzyl 9-hydroxy-5a,5b,8,8,11a-pentamethyl-1-(prop-1-en-2-yl)icosahydro-1H-cyclopenta[a]chrysene-3a-carboxylate (7.1 g, 12.98 mmol) in DCM (100 mL) was added PCC (4.20 g, 19.48 mmol). After stirring for five minutes, the mixture turned a deep crimson color. The mixture was further stirred for 5.5 h. The mixture was filtered through a pad of celite and silica gel which was washed with dichloromethane and then a 1:1 mixture of ethyl acetate:hexanes. The filtrate was concentrated under reduced pressure to give (1R,3aS,5aR,5bR,7aR,11aR,11bR,13aR,13bR)-benzyl 5a,5b,8,8,11a-pentamethyl-9-oxo-1-(prop-1-en-2-yl)icosahydro-1H-cyclopenta[a]chrysene-3a-carboxylate (6.92 g, 12.7 mmol, 98% yield) as a white foam. $^1$H NMR (500 MHz, CHLOROFORM-d) δ ppm 0.78 (s, 3H), 0.89 (s, 3H), 0.94 (s, 3H), 0.95-1.73 (m, 17H), 1.01 (s, 3H), 1.05 (s, 3H), 1.67 (s, 3H), 1.82-1.94 (m, 3H), 2.21 (td, J=12.28, 3.51 Hz, 1H), 2.28 (dt, J=12.59, 3.17 Hz, 1H), 2.34-2.42 (m, 1H), 2.43-2.51 (m, 1H), 3.01 (td, J=10.99, 4.88 Hz, 1H), 4.59 (s, 1H), 4.72 (d, J=1.83 Hz, 1H), 5.06-5.17 (m, 2H), 7.28-7.38 (m, 5H).

Intermediate 3: Preparation of (1R,3aS,5aR,5bR,7aR,11aR,11bR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate

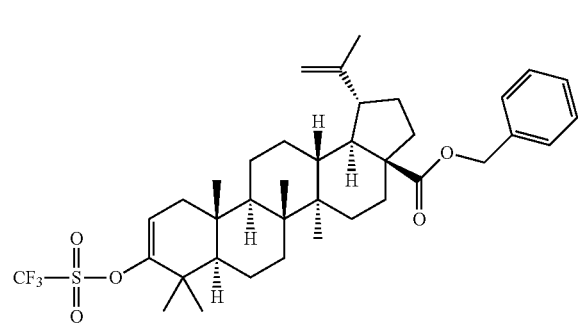

To a solution of (1R,3aS,5aR,5bR,7aR,11aR,13aR,13bR)-benzyl 5a,5b,8,8,11a-pentamethyl-9-oxo-1-(prop-1-en-2-yl)icosahydro-1H-cyclopenta[a]chrysene-3a-carboxylate (6.9 g, 12.67 mmol) and 1,1,1-trifluoro-N-phenyl-N-(trifluoromethylsulfonyl)methanesulfonamide (9.05 g, 25.3 mmol) in THF (200 mL) at −78° C. was added KHMDS (50.7 mL, 25.3 mmol) slowly. The reaction mixture was stirred for 1 hour at −78° C. TLC indicated starting material was consumed and desired product was formed. The reaction mixture was quenched with brine, extracted with diethyl ether. The extracts were dried over Na$_2$SO$_4$, filtered and concentrated under reduced pressure. The residue was dissolved in toluene and purified by biotage 2-10% toluene/hexanes and 5-10% ethyl acetate/hexanes to provide the desired product. $^1$H NMR (500 MHz, CHLOROFORM-d) δ ppm 0.77 (s, 3H), 0.88 (s, 3H), 0.91-1.77 (m, 17H), 0.94 (s, 3H), 1.00 (s, 3H), 1.10 (s, 3H), 1.67 (s, 3H), 1.81-1.96 (m, 2H), 2.14 (dd, J=17.09, 6.71 Hz, 1H), 2.22 (td, J=12.21, 3.36 Hz, 1H), 2.25-2.31 (m, 1H), 3.02 (td, J=10.99, 4.58 Hz, 1H), 4.59 (s, 1H), 4.72 (d, J=1.53 Hz, 1H), 5.05-5.12 (m, 1H), 5.13-5.18 (m, 1H), 5.54 (dd, J=6.71, 1.53 Hz, 1H), 7.29-7.41 (m, 5H).

General Method for the Preparation of Examples 4a-o

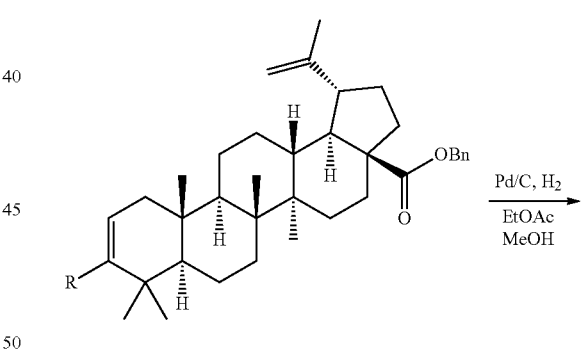

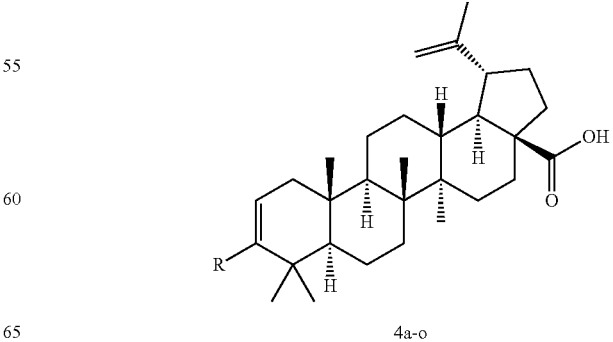

4a-o

Example 4a

Step 1

Suzuki Coupling

Preparation of 3-(4-((1R,3aS,5aR,5bR,7aR,11aS,13aR,13bR)-3a-(benzyloxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)propanoic acid

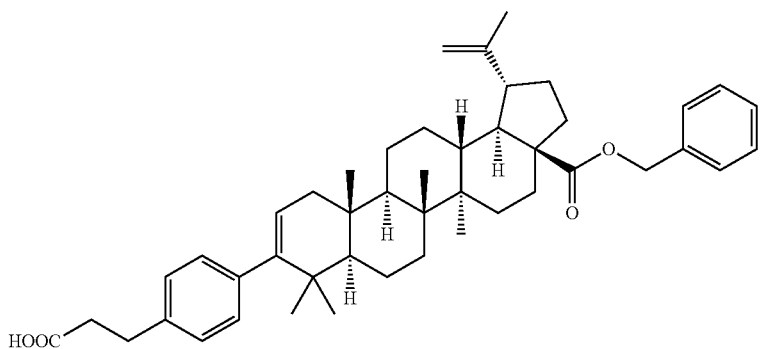

A mixture of (1R,3aS,5aR,5bR,7aR,11aR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (100 mg, 0.148 mmol), 3-(4-boronophenyl)propanoic acid (43.0 mg, 0.222 mmol), Pd(Ph$_3$P)$_4$ (17.07 mg, 0.015 mmol) and sodium carbonate (78 mg, 0.739 mmol) in DME (1 mL) and Water (1 mL) was heated to 100° C. for 1.5 hours. LCMS indicated desired product was formed. The reaction mixture was cooled to the room temperature and neutralized to pH=4-5 using 1N HCl. The reaction mixture was extracted with ethyl acetate. The extracts were dried over Na$_2$SO$_4$, filtered through a celite pad and concentrated under reduced pressure. The residue was purified by 80-100% ethyl acetate/hexanes to give the desired product, 3-(4-((1R,3aS,5aR,5bR,7aR,11aS,13aR,13bR)-3a-(benzyloxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)propanoic acid, as colorless oil (60 mg, 55%). LCMS: m/e 675.63 (M−H)$^-$, 4.78 min (method 5). $^1$H NMR (500 MHz, CHLOROFORM-d) d ppm 0.82 (s, 3H), 0.89 (s, 3H), 0.90 (s, 3H), 0.95 (s, 3H), 0.97 (s, 3H), 0.99-1.73 (m, 17H), 1.69 (s, 3H), 1.80-1.97 (m, 2H), 2.04-2.11 (m, 1H), 2.19-2.37 (m, 2H), 2.62-2.73 (m, 2H), 2.93 (t, J=7.78 Hz, 2H), 3.04 (td, J=10.91, 4.73 Hz, 1H), 4.60 (s, 1H), 4.73 (d, J=2.14 Hz, 1H), 5.05-5.20 (m, 2H), 5.21-5.29 (m, 1H), 6.92-7.00 (m, 2H), 7.06 (d, J=7.63 Hz, 1H), 7.17 (t, J=7.48 Hz, 1H), 7.28-7.41 (m, 5H).

Step 2

Deprotection of Benzyl Ester (Method A)

Preparation of (1R,3aS,5aR,5bR,7aR,11aS,11bR,13aR,13bR)-9-(4-(2-carboxyethyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid

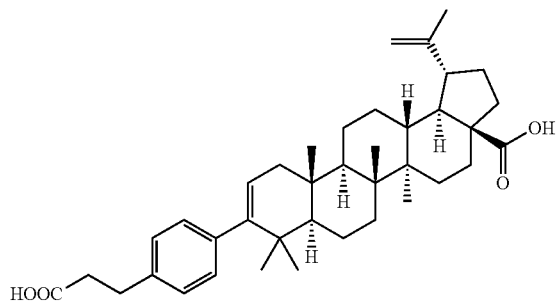

A mixture of 3-(4-((1R,3aS,5aR,5bR,7aR,11aS,13aR,13bR)-3a-(benzyloxycarbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)propanoic acid (60 mg, 0.089 mmol) and 10% Pd/C (28.3 mg, 0.027 mmol) in Ethyl acetate (2 mL) was stirred under 1 ATM of H$_2$ for 24 hours. LCMS indicated the completion of the reaction. The reaction mixture was filtered and the white solid was collected. The solid was purified by Prep. HPLC to provide the desired product, (1R,3aS,5aR,5bR,7aR,11aS,11bR,13aR,13bR)-9-(4-(2-carboxyethyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid, as white solid (10.32 mg, 30%). LCMS: m/e 585.59 (M−H)$^-$, 4.38 min (method 2). ¹H NMR (599 MHz, DMSO-D6_CDCl₃) δ ppm 0.91 (s, 3H), 0.93 (s, 3H), 1.00 (s, 6H), 1.02 (s, 3H), 1.05-1.72 (m, 17H), 1.71 (s, 3H), 1.84-1.95 (m, 2H), 2.10 (dd, J=17.58, 6.44 Hz, 1H), 2.20 (d, J=11.72 Hz, 1H), 2.30-2.39 (m, 1H), 2.60 (s, 2H), 2.85 (t, J=7.62 Hz, 2H), 3.02 (td, J=10.25, 5.27 Hz, 1H), 4.61 (br. s, 1H), 4.74 (s, 1H), 5.23 (d, J=5.27 Hz, 1H), 6.94 (d, J=7.62 Hz, 1H), 6.98 (s, 1H), 7.12 (d, J=8.20 Hz, 1H), 7.20 (t, J=7.62 Hz, 1H).

Example 4b

Preparation of (1R,3aS,5aR,5bR,7aR,11aS,11bR, 13aR,13bR)-9-(4-(3-carboxypropanamido)phenyl)- 5a,5b,8,8,11a-pentamethyl-1-(prop-1-en-2-yl)-2,3, 3a,4,5,5a,5b,6,7,7a,8,11,11a,11b,12,13,13a,13b- octadecahydro-1H-cyclopenta[a]chrysene-3a- carboxylic acid

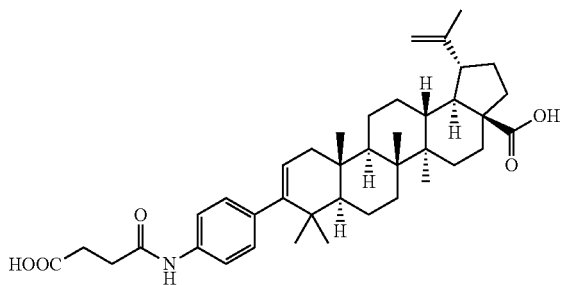

The title compound was prepared following the methods described above for (1R,3aS,5aR,5bR,7aR,11aS,11bR,13aR, 13bR)-9-(4-(2-carboxyethyl)phenyl)-5a,5b,8,8,11a-pentam-ethyl-1-(prop-1-en-2-yl)-2,3,3a,4,5,5a,5b,6,7,7a,8,11,11a, 11b,12,13,13a,13b-octadecahydro-1H-cyclopenta[a]chrysene-3a-carboxylic acid (example 4a) using 4-(4-boronophenylamino)-4-oxobutanoic acid as the reactant boronic acid. The product was isolated as a white solid (2.98 mg, 9%). LCMS: m/e 628.63 (M−H)⁻, 3.71 min (method 2). ¹H NMR (599 MHz, DMSO-D6_CDCl₃) δ ppm 0.91 (s, 3H), 0.93 (s, 3H), 0.98 (s, 3H), 0.99 (s, 3H), 1.02 (s, 3H), 1.03-1.71 (m, 17H), 1.71 (s, 3H), 1.84-1.93 (m, 2H), 2.09 (dd, J=17.87, 5.57 Hz, 1H), 2.20 (d, J=12.30 Hz, 1H), 2.29-2.39 (m, 1H), 2.59-2.62 (m, 2H), 2.97-3.10 (m, 1H), 3.30-3.33 (m, 2H), 4.61 (br. s, 1H), 4.74 (s, 1H), 5.24 (d, J=5.27 Hz, 1H), 7.03 (d, J=8.79 Hz, 2H), 7.51 (d, J=8.20 Hz, 2H).

Example 4c

Preparation of (1R,3aS,5aR,5bR,7aR,11aS,11bR, 13aR,13bR)-9-(4-(1-carboxycyclopropyl)phenyl)-5a, 5b,8,8,11a-pentamethyl-1-(prop-1-en-2-yl)-2,3,3a,4, 5,5a,5b,6,7,7a,8,11,11a,11b,12,13,13a,13b- octadecahydro-1H-cyclopenta[a]chrysene-3a- carboxylic acid

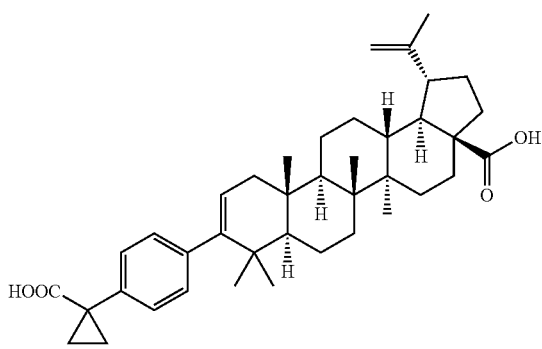

The title compound was prepared following the methods described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 1-(4-boronophenyl)cyclopropanecarboxylic acid as the reactant boronic acid. The product was isolated as a white solid (1.76 mg, 5%). LCMS: m/e 597.64 (M−H)⁻, 4.43 min (method 2). ¹H NMR (599 MHz, DMSO-D6_CDCl₃) δ ppm 0.92 (s, 3H), 0.94 (s, 3H), 0.99 (d, J=3.52 Hz, 6H), 1.02 (s, 3H), 1.03-1.71 (m, 21H), 1.71 (s, 3H), 1.82-1.95 (m, 2H), 2.10 (dd, J=17.28, 6.15 Hz, 1H), 2.20 (d, J=12.30 Hz, 1H), 2.30-2.39 (m, 1H), 2.97-3.09 (m, 1H), 4.61 (br. s, 1H), 4.74 (s, 1H), 5.25 (d, J=4.69 Hz, 1H), 7.04 (d, J=7.62 Hz, 2H), 7.25 (d, J=7.62 Hz, 2H).

Example 4d

Preparation of (1R,3aS,5aR,5bR,7aR,11aS,11bR, 13aR,13bR)-9-(4-carboxy-3-fluorophenyl)-5a,5b,8, 8,11a-pentamethyl-1-(prop-1-en-2-yl)-2,3,3a,4,5,5a, 5b,6,7,7a,8,11,11a,11b,12,13,13a,13b- octadecahydro-1H-cyclopenta[a]chrysene-3a- carboxylic acid

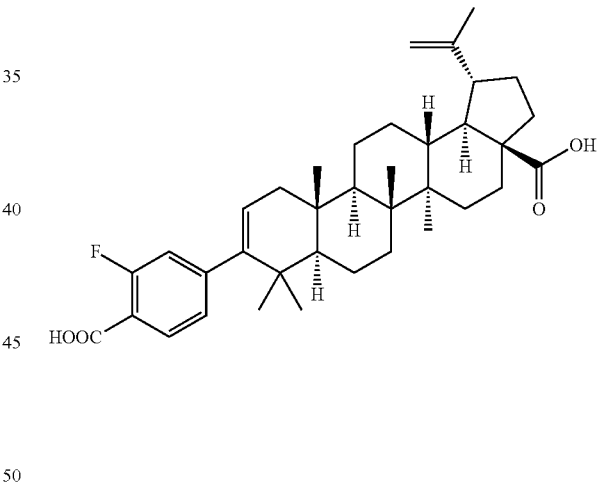

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 4-borono-2-fluorobenzoic acid as the reactant boronic acid. The product was isolated as a white solid (6.46 mg, 19%). LCMS: m/e 575.54 (M−H)⁻, 3.88 min (method 2). ¹H NMR (599 MHz, DMSO-D6_CDCl₃) δ ppm 0.95 (s, 6H), 0.98 (s, 3H), 1.00 (s, 3H), 1.02 (s, 3H), 1.04-1.76 (m, 17H), 1.71 (s, 3H), 1.88 (d, J=7.03 Hz, 2H), 2.13 (dd, J=17.58, 6.44 Hz, 1H), 2.20 (d, J=12.30 Hz, 1H), 2.29-2.39 (m, 1H), 2.98-3.07 (m, 1H), 4.61 (s, 1H), 4.74 (s, 1H), 5.33 (d, J=5.27 Hz, 1H), 6.96 (d, J=11.13 Hz, 1H), 7.02 (d, J=8.20 Hz, 1H), 7.79 (t, J=7.62 Hz, 1H).

Example 4e

Preparation of (1R,3aS,5aR,5bR,7aR,11aS,11bR, 13aR,13bR)-5a,5b,8,8,11a-pentamethyl-9-(3-(N-methylsulfamoyl)phenyl)-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylic acid

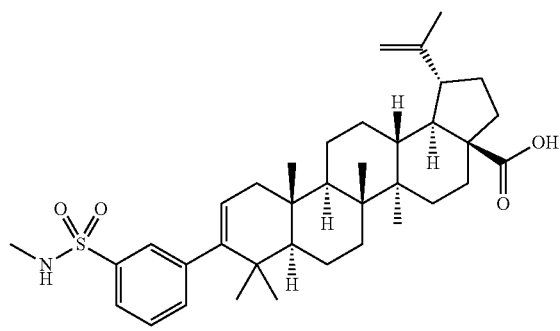

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 3-(N-methylsulfamoyl)phenylboronic acid as the reactant boronic acid. The product was isolated as a white solid (32.47 mg, 62%). LCMS: m/e 606.58 (M−H)⁻, 4.47 min (method 2). ¹H NMR (599 MHz, DMSO-D6_CDCl₃) δ ppm 0.94 (s, 3H), 0.95 (s., 3H), 1.00 (br. s., 6H), 1.03 (s, 3H), 1.04-1.78 (m, 17H), 1.71 (s, 3H), 1.88 (t, J=7.03 Hz, 2H), 2.14 (dd, J=17.28, 6.15 Hz, 1H), 2.20 (d, J=12.30 Hz, 1H), 2.31-2.39 (m, 1H), 2.46 (d, J=4.69 Hz, 3H), 2.99-3.08 (m, 1H), 4.61 (s., 1H), 4.74 (s, 1H), 5.34 (d, J=5.86 Hz, 1H), 7.39 (d, J=8.20 Hz, 1H), 7.46 (q, J=5.27 Hz, 1H), 7.51-7.58 (m, 2H), 7.71 (d, J=7.62 Hz, 1H).

Example 4f

Preparation of (1R,3aS,5aR,5bR,7aR,11aS,11bR, 13aR,13bR)-9-(4-hydroxyphenyl)-5a,5b,8,8,11a-pentamethyl-1-(prop-1-en-2-yl)-2,3,3a,4,5,5a,5b,6,7, 7a,8,11,11a, 11b,12,13,13a,13b-octadecahydro-1H-cyclopenta[a]chrysene-3a-carboxylic acid

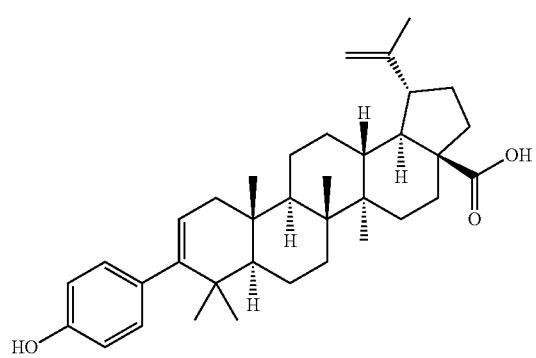

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 4-hydroxyphenylboronic acid as the reactant boronic acid. The product was isolated as a white solid (1.25 mg, 4%). LCMS: m/e 529.55 (M−H)⁻, 4.34 min (method 2).

Example 4g

Preparation of (1R,3aS,5aR,5bR,7aR,11aS,11bR, 13aR,13bR)-5a,5b,8,8,11a-pentamethyl-9-(3-(methylsulfonamido)phenyl)-1-(prop-1-en-2-yl)-2,3,3a,4, 5,5a,5b,6,7,7a,8,11,11a,11b,12,13,13a,13b-octadecahydro-1H-cyclopenta[a]chrysene-3a-carboxylic acid

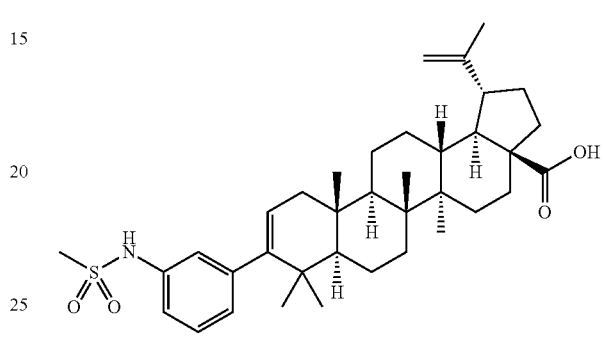

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 3-(methylsulfonamido)phenylboronic acid as the reactant boronic acid. The product was isolated as a white solid (46.41 mg, 90%). LCMS: m/e 606.58 (M−H)⁻, 4.37 min (method 2). ¹H NMR (599 MHz, DMSO-D6_CDCl₃) δ ppm 0.93 (s, 6H), 0.99 (s, 3H), 1.02 (s, 3H), 1.03-1.74 (m, 17H), 1.71 (s, 3H), 1.84-1.96 (m, 2H), 2.11 (dd, J=16.99, 5.86 Hz, 1H), 2.20 (d, J=12.30 Hz, 1H), 2.30-2.39 (m, 1H), 2.96 (s, 3H), 2.99-3.07 (m, 1H), 4.61 (s., 1H), 4.74 (s, 1H), 5.28 (d, J=4.69 Hz, 1H), 6.87 (d, J=7.62 Hz, 1H), 7.03 (s, 1H), 7.14 (d, J=8.20 Hz, 1H), 7.25 (t, J=7.62 Hz, 1H).

Example 4h

Preparation of (1R,3aS,5aR,5bR,7aR,11aS,11bR, 13aR,13bR)-9-(4-((E)-2-carboxyvinyl)phenyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysene-3a-carboxylic acid

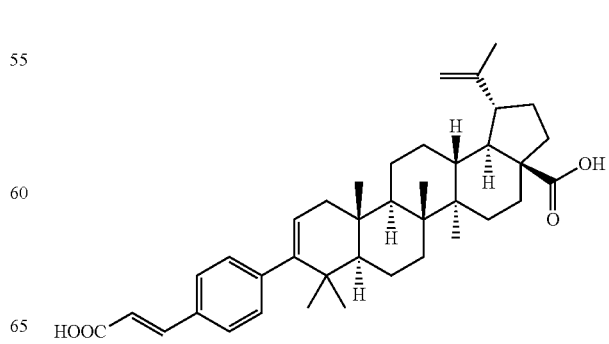

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using (E)-3-(4-boronophenyl)acrylic acid as the reactant boronic acid. The product was isolated as a white solid (3.65 mg, 11%). LCMS: m/e 583.60 (M−H)⁻, 5.03 min (method 2). ¹H NMR (599 MHz, DMSO-D6_CDCl₃) δ ppm 0.94 (d, J=3.52 Hz, 6H), 1.00 (s, 6H), 1.02 (s, 3H), 1.03-1.76 (m, 17H), 1.71 (s, 3H), 1.88 (d, J=7.03 Hz, 2H), 2.08-2.16 (m, 1H), 2.20 (d, J=12.30 Hz, 1H), 2.30-2.40 (m, 1H), 3.02 (d, J=5.27 Hz, 1H), 4.61 (s., 1H), 4.74 (s, 1H), 5.28 (d, J=4.69 Hz, 1H), 6.49 (d, J=15.82 Hz, 1H), 7.17 (d, J=8.20 Hz, 2H), 7.54-7.71 (m, 3H).

Example 41

Preparation of (1R,3aS,5aR,5bR,7aR,11aS,11bR, 13aR,13bR)-9-(3-(2H-tetrazol-5-yl)phenyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxylic acid

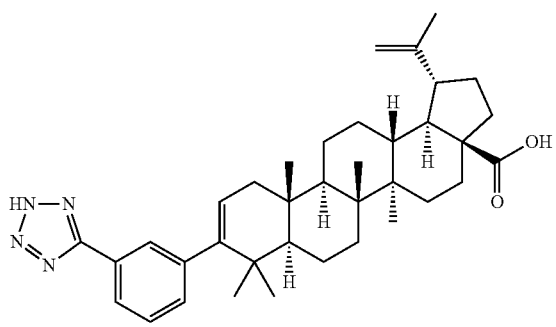

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 3-(2H-tetrazol-5-yl)phenylboronic acid as the reactant boronic acid. The product was isolated as a white solid (4.56 mg, 26%). LCMS: m/e 581.53 (M−H)⁻, 4.12 min (method 3). ¹H NMR (400 MHz, <DMSOmix>) δ ppm 0.95 (d, J=4.10 Hz, 6H), 0.99 (s, 3H), 1.01 (s, 6H), 1.03-1.76 (m, 17H), 1.69 (s, 3H), 1.81-1.93 (m, 2H), 2.07-2.23 (m, 2H), 2.34 (dd, J=13.47, 2.34 Hz, 1H), 2.95-3.06 (m, 1H), 4.58 (s, 1H), 4.72 (s, 1H), 5.32 (d, J=4.39 Hz, 1H), 7.22 (d, J=6.44 Hz, 1H), 7.38-7.51 (m, 1H), 7.81 (s, 1H), 7.92 (d, J=7.32 Hz, 1H).

Example 4j

Preparation of (1R,3aS,5aR,5bR,7aR,11aS,11bR, 13aR,13bR)-5a,5b,8,8,11a-pentamethyl-9-(4-(methylsulfonyl)phenyl)-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxylic acid

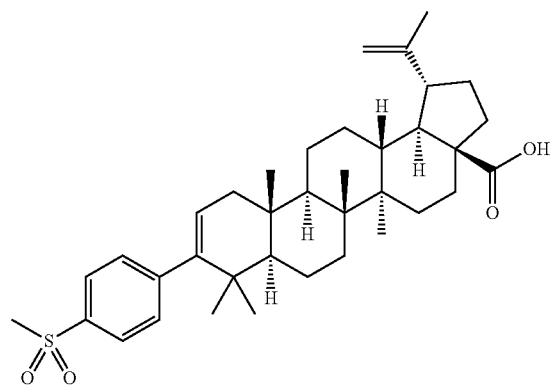

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 4-(methylsulfonyl)phenylboronic acid as the reactant boronic acid. The product was isolated as a white solid (3.5 mg, 20%). LCMS: m/e 591.61 (M−H)⁻, 6.74 min (method 3). ¹H NMR (400 MHz, <DMSOmix>) δ ppm 0.92 (s, 6H), 0.98 (s, 6H), 1.00 (s, 3H), 1.02-1.77 (m, 17H), 1.68 (s, 3H), 1.79-1.97 (m, 2H), 2.05-2.23 (m, 2H), 2.32 (t, J=13.47 Hz, 1H), 2.90-3.06 (m, 1H), 3.19 (s, 3H), 4.58 (s, 1H), 4.71 (s, 1H), 5.29 (d, J=5.57 Hz, 1H), 7.36 (d, J=6.44 Hz, 2H), 7.85 (d, J=8.20 Hz, 2H).

Example 4k

Preparation of (1R,3aS,5aR,5bR,7aR,11aS,11bR, 13aR,13bR)-9-(3-(2-carboxyethyl)phenyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxylic acid

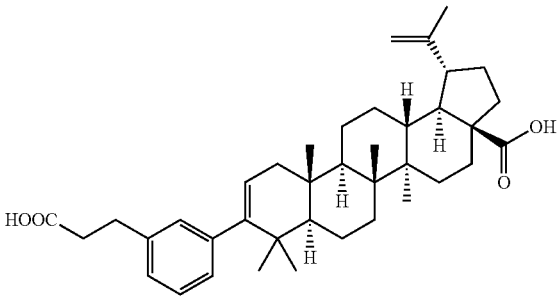

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using (E)-3-(3-boronophenyl)acrylic acid as the reactant boronic acid. The product was isolated as a white solid (34.4 mg, 80%). LCMS: m/e 585.63 (M−H)$^-$, 6.47 min (method 3). $^1$H NMR (400 MHz, <DMSOmix>) δ ppm 0.89 (d, 6H), 0.97 (s, 6H), 1.00 (s, 3H), 1.01-1.66 (m, 17H), 1.68 (s, 3H), 1.80-1.94 (m, 2H), 2.02-2.12 (m, 1H), 2.13-2.22 (m, 1H), 2.26-2.39 (m, 1H), 2.55-2.60 (m, 2H), 2.83 (t, J=7.62 Hz, 2H), 2.94-3.07 (m, 1H), 4.58 (br. s., 1H), 4.71 (s, 1H), 5.20 (d, J=4.10 Hz, 1H), 6.88-6.98 (m, 2H), 7.08 (d, J=6.44 Hz, 1H), 7.13-7.22 (m, 1H).

Compound 4l: Preparation of (1R,3aS,5aR,5bR,7aR, 11aS,11bR,13aR,13bR)-9-(2-(2-carboxyethyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid

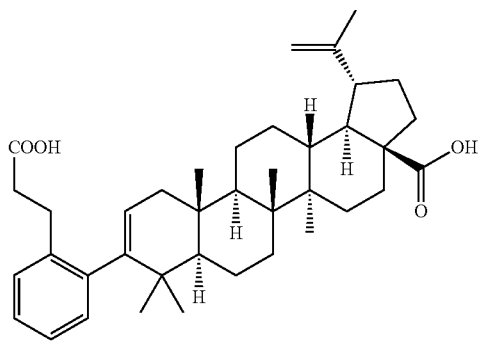

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using (E)-3-(2-boronophenyl)acrylic acid as the reactant boronic acid. The product was isolated as a white solid (37.4 mg, 86%). LCMS: m/e 585.58 (M−H)$^-$, 6.84 min (method 3). $^1$H NMR (400 MHz, <DMSOmix>) δ ppm 0.80 (d, 3H), 0.98 (s, 6H), 1.00 (s, 6H), 1.04-1.73 (m, 17H), 1.68 (s, 3H), 1.79-1.96 (m, 2H), 2.00-2.23 (m, 2H), 2.27-2.37 (m, 1H), 2.71-2.83 (m, 2H), 2.84-2.95 (m, 2H), 2.96-3.05 (m, 1H), 4.59 (s, 1H), 4.72 (s, 1H), 5.24 (d, J=4.98 Hz, 1H), 6.97-7.06 (m, 1H), 7.06-7.14 (m, 1H), 7.14-7.30 (m, 2H).

Compound 4m: Preparation of 3-(4-((1R,3aS,5aR, 5bR,7aR,11aS,11bR,13aR,13bR)-3a-carboxy-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) phenyl)quinoline-4-carboxylic acid

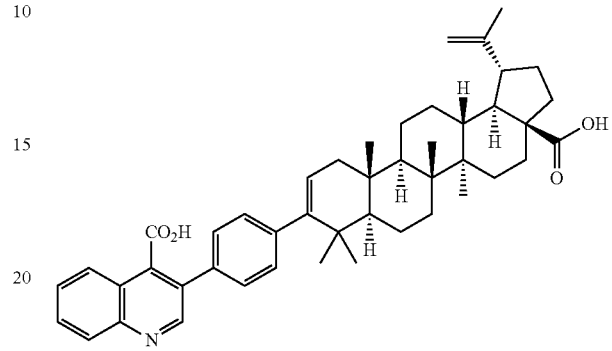

The title compound was prepared following the method described above for compound (1R,3aS,5aR,5bR,7aR,11aS, 11bR,13aR,13bR)-9-(4-(2-carboxyethyl)phenyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 4a) using 2-(4-boronophenyl)quinoline-4-carboxylic acid as the reactant boronic acid. The product was isolated as a white solid (4.7 mg, 27%). LCMS: m/e 684.65 (M−H)$^-$, 5.11 min (method 3). $^1$H NMR (400 MHz, <DMSOmix>) δ ppm 0.95-1.00 (m, 9H), 1.01 (s, 6H), 1.05-1.77 (m, 17H), 1.69 (s, 3H), 1.80-1.94 (m, 2H), 2.07-2.23 (m, 2H), 2.31-2.38 (m, 1H), 2.94-3.06 (m, 1H), 4.59 (s, 1H), 4.72 (s, 1H), 5.33 (d, J=6.15 Hz, 1H), 7.30 (d, J=7.32 Hz, 2H), 7.59-7.67 (m, 1H), 7.74-7.84 (m, 1H), 8.08-8.14 (m, 1H), 8.18 (d, J=8.79 Hz, 2H), 8.32-8.42 (m, 1H), 8.72 (d, J=6.15 Hz, 1H).

Example 4n

Preparation of 5-((1R,3aS,5aR,5bR,7aR,11aS,11bR, 13aR,13bR)-3a-carboxy-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)thiophene-2-carboxylic acid

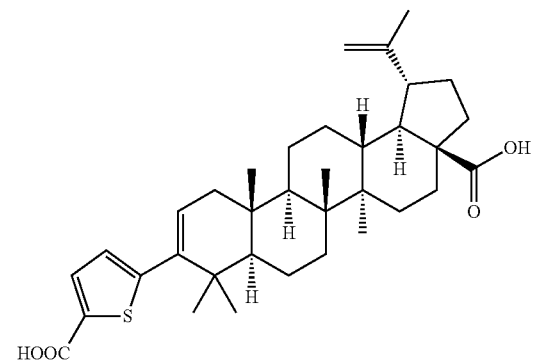

The title compound was prepared following the method described above for compound (1R,3aS,5aR,5bR,7aR,11aS,11bR,13aR,13bR)-9-(4-(2-carboxyethyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (example 4a) using 5-boronothiophene-2-carboxylic acid as the reactant boronic acid. The product was isolated as a white solid (4.15 mg, 23%). LCMS: m/e 563.53 (M−H)⁻, 2.94 min (method 4). ¹H NMR (400 MHz, <DMSOmix>) δ ppm 0.90 (br. s., 3H), 0.96 (s, 3H), 0.98 (s, 3H), 1.04 (s, 3H), 1.06 (s, 3H), 1.09-1.76 (m, 17H), 1.68 (s, 3H), 1.80-1.94 (m, 2H), 2.10-2.23 (m, 2H), 2.25-2.40 (m, 1H), 2.91-3.05 (m, 1H), 4.58 (br. s., 1H), 4.71 (br. s., 1H), 5.75 (d, J=5.86 Hz, 1H), 6.90 (d, J=3.22 Hz, 1H), 7.51 (br. s., 1H).

Compound 4o: Preparation of (1R,3aS,5aR,5bR,7aR,11aS,11bR,13aR,13bR)-9-(4-carboxy-3-chlorophenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid

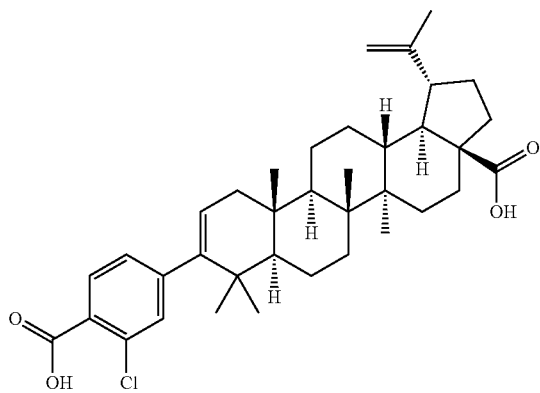

The title compound was prepared following the method described above for compound (1R,3aS,5aR,5bR,7aR,11aS,11bR,13aR,13bR)-9-(4-(2-carboxyethyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (example 4a) using 4-borono-2-chlorobenzoic acid as the reactant boronic acid. Purification of the product was accomplished by first using Biotage flash chromatography with a 0-50% ethyl acetate in hexanes gradient with 0.1% acetic acid added to the mixture. The compound was not sufficiently pure, so further purification by prep HPLC followed (acetonitrile/water mobile phase with TFA buffer on a C18 reverse phase column). After concentrating the desired fractions, the title compound was isolated as a white film (6.1 mg, 6.8% yield over two steps). LCMS: m/e 591.60 (M−H)⁻, 1.54 min (method 1). ¹H NMR (500 MHz, Pyr) δ ppm 0.92 (br. s., 6H), 0.96 (s, 3H), 1.10 (s, 3H), 1.11 (s, 3H), 1.18-1.84 (m, 15H), 1.83 (s, 3H), 1.89 (t, J=13.28 Hz, 1H), 1.99 (br. s., 1H), 2.09 (dd, J=17.09, 6.10 Hz, 1H), 2.24-2.33 (m, 2H), 2.66 (d, J=12.51 Hz, 1H), 2.81 (t, J=11.75 Hz, 1H), 3.54-3.63 (m, 1H), 4.82 (s, 1H), 5.00 (s, 1H), 5.37 (d, J=5.80 Hz, 1H), 7.24 (d, J=8.24 Hz, 1H), 7.51 (s, 1H), 8.21 (d, J=7.63 Hz, 1H).

Intermediate 4: Preparation of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate

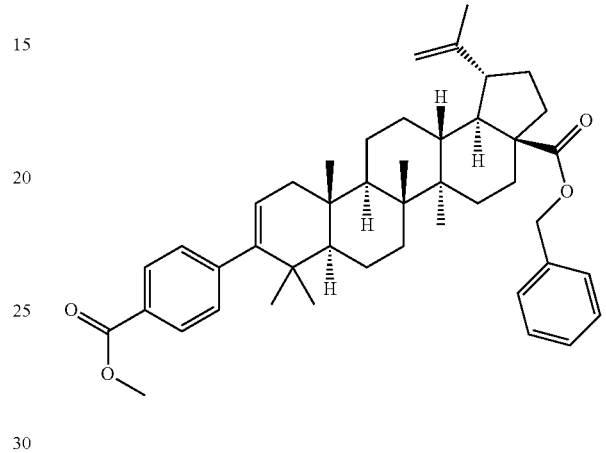

To a round bottom flask containing a solution of (1R,3aS,5aR,5bR,7aR,11aR,11bR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (6.21 g, 9.18 mmol) in dioxane (25 mL) was added 2-propanol (25 mL) and water (15 mL) followed by sodium carbonate monohydrate (3.42 g, 27.5 mmol), 4-methoxycarbonylphenylboronic acid (2.478 g, 13.77 mmol), and tetrakis(triphenylphosphine)palladium(0) (0.318 g, 0.275 mmol). The flask was attached to a reflux condenser, was flushed with N₂, and was heated to reflux overnight. After heating the mixture for 14.5 h, it was cooled to rt and was diluted with water (75 mL). The mixture was extracted with ethyl acetate (3×75 mL) and washed with brine. The combined organic layers were dried with MgSO₄, filtered, and concentrated under reduced pressure. The residue was adsorbed to silica gel and was purified by Biotage flash chromatography using a 0-20% EtOAc in hexanes gradient. The fractions containing the expected product was combined and concentrated under reduced pressure. The expected product, (1R,3aS,5aR,5bR,7aR,11aS,11bR,13aR 13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (4.16 g, 6.28 mmol, 68.4% yield), was isolated as a white foam. ¹H NMR (500 MHz, CHLOROFORM-d) δ ppm 0.82 (s, 3H), 0.87-1.75 (m, 17H), 0.91 (s, 3H), 0.92 (s, 3H), 0.95 (s, 3H), 0.97 (s, 3H), 1.69 (s, 3H), 1.82-1.95 (m, 2H), 2.09 (dd, J=17.24, 6.26 Hz, 1H), 2.20-2.32 (m, 2H), 3.04 (td, J=10.91, 4.73 Hz, 1H), 3.90 (s, 3H), 4.60 (s, 1H), 4.73 (d, J=1.83 Hz, 1H), 5.07-5.19 (m, 2H), 5.28 (dd, J=6.10, 1.83 Hz, 1H), 7.19 (d, J=8.24 Hz, 2H), 7.29-7.40 (m, 5H), 7.92 (d, J=8.24 Hz, 2H).

Deprotection of Benzyl Group (Method B).

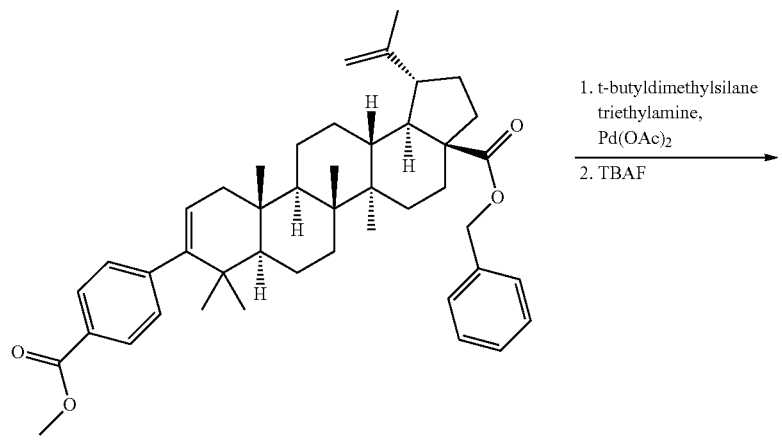

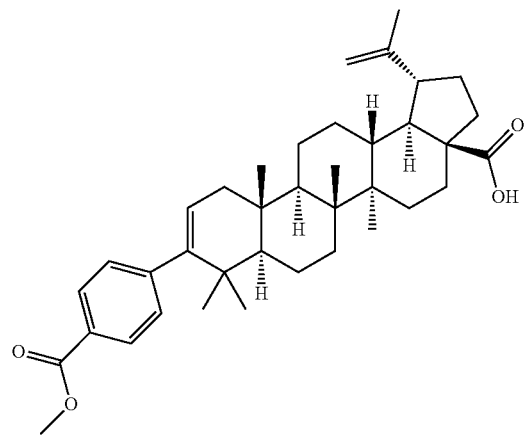

Intermediate 5: Preparation of (1R,3aS,5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate

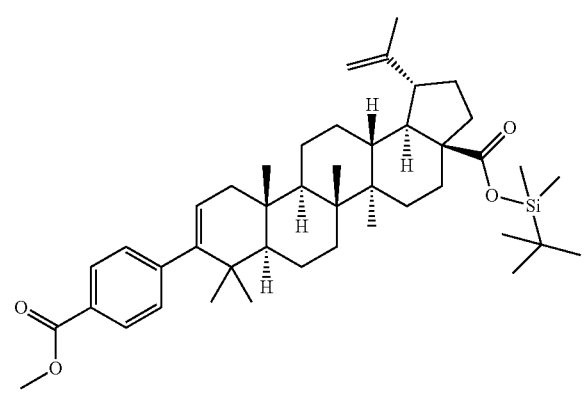

To a solution of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.82 g, 5.76 mmol) in dichloroethane (100 mL) was added triethylamine (1.285 mL, 9.22 mmol), tert-butyldimethylsilane (1.912 mL, 11.52 mmol), and palladium(II) acetate (0.647 g, 2.88 mmol). The mixture was flushed with $N_2$, then was heated to 60° C. After 2 h, the reaction was cooled to rt, was filtered through a pad of celite and silica gel to remove the solids which were washed with 25% EtOAc in hexanes. The filtrate was concentrated under reduced pressure and was treated with 20 mL of acetic acid, 10 mL of THF and 3 mL of water. After stirring for 1 h the solids that formed were collected by filtration and were washed with water to give (1R,3aS,5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (3.62 g, 5.27 mmol, 91% yield) as a white solid. $^1$H NMR (400 MHz, CHLOROFORM-d) δ ppm 0.28-0.32 (m, 6H), 0.90-1.78 (m, 16H), 0.94 (s, 6H), 0.98 (s, 9H), 0.99 (br. s., 3H), 1.01 (s, 6H), 1.71 (s, 3H), 1.84-2.02 (m, 2H), 2.06-2.17 (m, 1H), 2.22-2.35 (m, 2H), 3.08 (td, J=10.92, 4.27 Hz, 1H), 3.92 (s, 4H), 4.62 (s, 1H), 4.75 (d, J=1.76 Hz, 1H), 5.30 (dd, J=6.15, 1.63 Hz, 1H), 7.21 (d, J=8.28 Hz, 2H), 7.94 (d, J=8.28 Hz, 2H).

Preparation of ((1R,3aS,5aR,5bR,7aR,9S,11aR, 11bR,13aR,13bR)-9-hydroxy-5a,5b,8,8,11a-pentamethyl-1-(prop-1-en-2-yl)icosahydro-1H-cyclopenta[a]chrysen-3a-yl)methyl benzoate

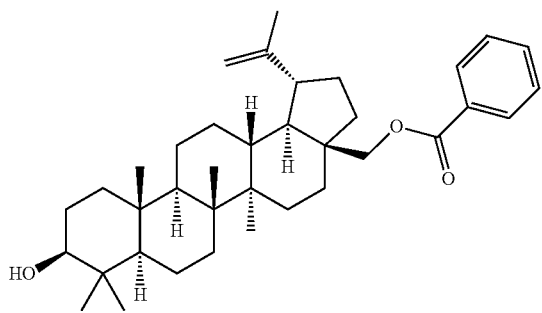

Betuline (2.5 g, 5.65 mmol), Benzoic anhydride (2.147 mL, 11.29 mmol) and DMAP (0.690 g, 5.65 mmol) were heated in pyridine (50 mL) for 3 h. TLC showed no starting material. The reaction was quenched with water and the mixture was concentrated in vacuo to remove most of the pyridine. Methylene chloride was added and the organic phase was separated and dried over $Na_2SO_4$. The drying agent was removed by filtration and the filtrate was concentrated under reduced pressure. The crude material containing ((1R,3aS,5aR,5bR,7aR,9S,11aR,11bR,13bR)-9-hydroxy-5a,5b,8,8,11a-pentamethyl-1-(prop-1-en-2-yl)icosahydro-1H-cyclopenta[a]chrysen-3a-yl)methyl benzoate was taken to the next step without further purification.

Preparation of ((1R,3aS,5aR,5bR,7aR,11aR,11bR, 13aR,13bR)-5a,5b,8,8,11a-pentamethyl-9-oxo-1-(prop-1-en-2-yl)icosahydro-1H-cyclopenta[a]chrysen-3a-yl)methyl benzoate

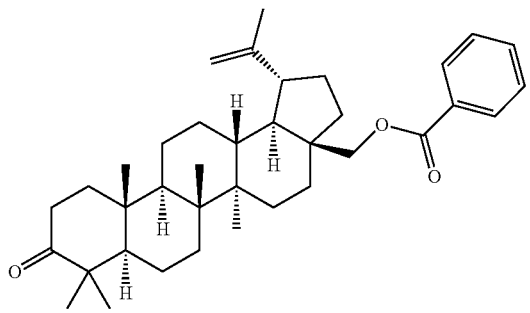

The crude material containing ((1R,3aS,5aR,5bR,7aR,9S,11aR,11bR,13bR)-9-hydroxy-5a,5b,8,8,11a-pentamethyl-1-(prop-1-en-2-yl)icosahydro-1H-cyclopenta[a]chrysen-3a-yl)methyl benzoate (2.98 g, 5.45 mmol) from page above was dissolved in $CH_2Cl_2$ (50 ml) and treated with PCC (1.762 g, 8.18 mmol). The mixture was stirred at rt for 2 h. TLC showed no starting material and one less polar product. The mixture was filtered through celite and silica gel and the filtrate was concentrated in vacuo to afford the title compound as a white solid Preparation of ((1R,3aS,5aR,5bR,7aR,11aR,11bR, 13aR,13bR)-5a,5b,8,8,11a-pentamethyl-1-(prop-1-en-2-yl)-9-(trifluoromethylsulfonyloxy)-2,3,3a,4,5, 5a,5b,6,7,7a,8,11,11a,11b,12,13,13a,13b-octadecahydro-1H-cyclopenta[a]chrysen-3a-yl) methyl benzoate

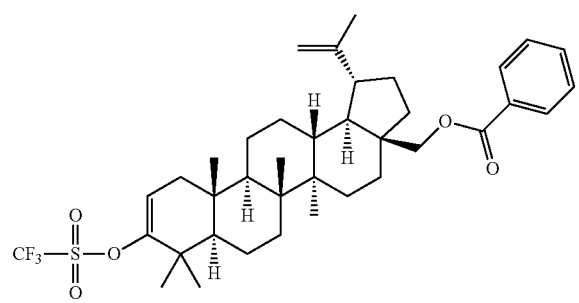

A mixture of ((1R,3aS,5aR,5bR,7aR,11aR,11bR,13bR)-5a, 5b,8,8,11a-pentamethyl-9-oxo-1-(prop-1-en-2-yl)icosahydro-1H-cyclopenta[a]chrysen-3a-yl)methyl benzoate (2.97 g, 5.45 mmol), and N-Phenylbis(trifluoromethane)sulfonimide (3.89 g, 10.90 mmol) was stirred in THF (30 mL) at −78° C. KHMDS (0.5 in Toluene) (21.80 mL, 10.90 mmol) was slowly added and the reaction mixture and was kept at −78° C. for 1 h. TLC showed starting material and a less polar spot. KHMDS (1 eq, 5 ml) was added and the mixture was stirred at −78° C. for 1 h longer. Reaction was quenched with brine and warmed at rt. The organic layer was extracted with ether and dried over $Na_2SO_4$, filtered, concentrated and purified using silica gel (0-10% Toluene/Hexanes) to separate the excess triflate reagent from the product, ((1R,3aS,5aR,5bR, 7aR,11aR,11bR,13bR)-5a,5b,8,8,11a-pentamethyl-1-(prop-1-en-2-yl)-9-(trifluoromethylsulfonyloxy)-2,3,3a,4,5,5a,5b, 6,7,7a,8,11,11a,11b,12,13,13a,13b-octadecahydro-1H-cyclopenta[a]chrysen-3a-yl)methyl benzoate (2.22 g, 3.28 mmol, 60.2% yield for 3 steps), which was isolated as a white solid. $^1$H NMR (400 MHz, CHLOROFORM-d) δ ppm 0.94 (s, 3H), 1.03 (s, 3H), 1.04 (s, 3H), 1.10-1.86 (m, 18H), 1.12 (s, 3H), 1.14 (s, 3H), 1.73 (s, 3H), 1.92-2.13 (m, 3H), 2.18 (dd, J=17.07, 6.78 Hz, 1H), 2.55 (td, J=11.11, 5.90 Hz, 1H), 4.12 (d, J=11.04 Hz, 1H), 4.55 (dd, J=11.04, 1.25 Hz, 1H), 4.64 (s, 1H), 4.75 (d, J=2.01 Hz, 1H), 5.58 (dd, J=6.65, 1.88 Hz, 1H), 7.43-7.49 (m, 2H), 7.55-7.60 (m, 1H), 8.05-8.09 (m, 2H).

General Method for the Preparation of Compounds 5a-u

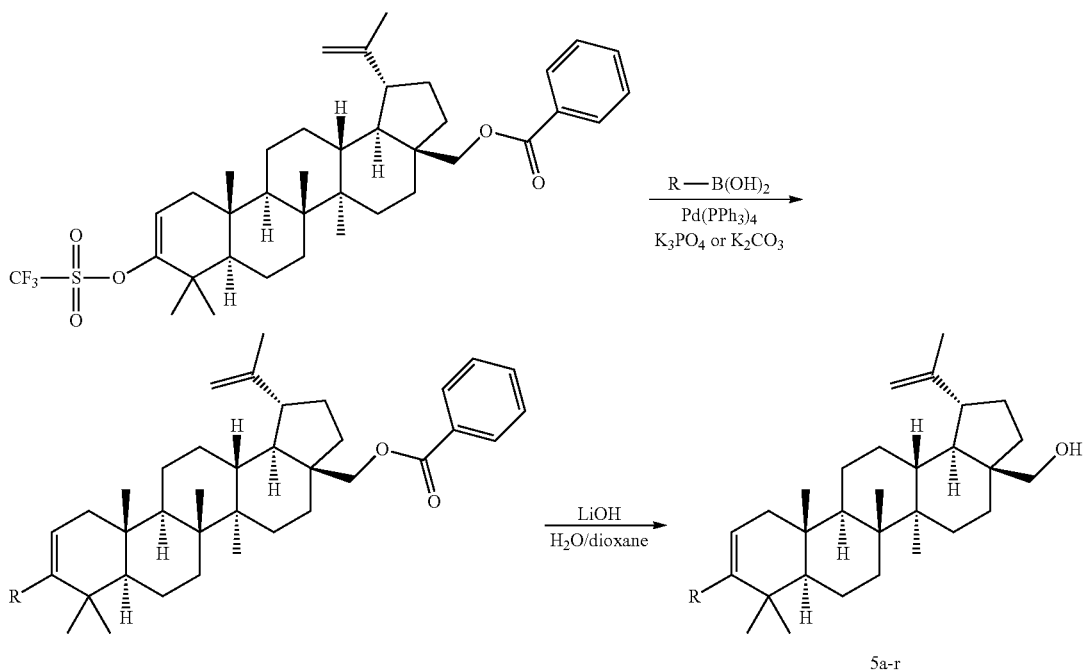

Step 1: Suzuki Coupling

To a sealable vial containing ((1R,3aS,5aR,5bR,7aR,11aR,11bR,13aR,13bR)-5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysen-3a-yl)methyl benzoate (0.074-0.322 mmol) was added the corresponding boronic acid (1.05-1.5 equiv.), base (either $K_3PO_4$ (4 equiv.) or sodium carbonate monohydrate (3 equiv.)), and tetrakis(triphenylphosphine) palladium(0) (0.03-0.1 equiv.). The mixture was diluted with either 1,4-dioxane, a mixture of 1,4-dioxane:water (4:1), a mixture of 2-propanol:water (4:1), or a mixture of 1,4-dioxane:2-propanol:water (2:2:1) to a concentration of 0.059-0.074 M. The vial was flushed with $N_2$, sealed, and heated to 85° C.-100° C. After 3-24 h of heating, the mixture was cooled to rt. The mixture was diluted with either sat. $NH_4Cl$, 1N HCl, or water and was extracted with dichloromethane. The combined organic layers were dried with $Na_2SO_4$. The drying agent was removed by filtration and the filtrate was concentrated under reduced pressure. The residue was either used directly in the next step, or was purified by Biotage flash chromatography to afford the expected C-3 coupled product which was used in the next step.

Step 2: Deprotection of Alcohol

To a solution of the C-3 coupled product from the previous step (0.058-0.295 mmol) in dioxane:water (3:1 or 4:1) was added lithium hydroxide monohydrate (19-43 equiv.). The mixture was heated to 75° C. for 3-15 h, was cooled to rt, and was quenched with 1N HCl. The mixture was extracted with dichloromethane and the organic layers were combined and dried with $Na_2SO_4$. The drying agent was removed by filtration and the filtrate was concentrated under reduced pressure. The residue was purified by either Biotage flash chromatography, crystallization from dioxane and water, or prep HPLC to give the expected deprotected product.

Example 5a

Preparation of 2-chloro-4-((1R,3aS,5aR,5bR,7aR,11aS,11bR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) benzoic acid

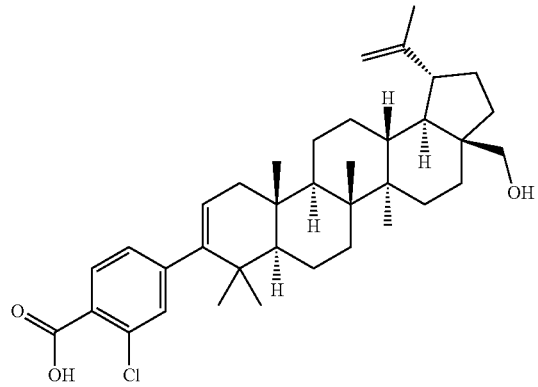

The title compound was prepared by the general method described above using 4-carboxy-3-chlorophenylboronic acid as the reactant boronic acid. The product was purified by biotage flash chromatography using a 25-50% EtOAc in hexanes gradient with 0.1% HOAc added. Fractions containing the product were concentrated to give the title compound as a white solid (20.1 mg, 0.034 mmol, 11.5% yield over two steps). LCMS: m/e 577.6 (M−H)⁻, 1.60 min (method 1). $^1$H NMR (500 MHz, CHLOROFORM-d) δ ppm 0.93 (s, 3H), 0.93 (s, 3H), 0.96 (s, 3H), 1.00-2.12 (m, 22H), 1.01 (s, 3H), 1.08 (s, 3H), 1.69 (s, 3H), 2.40 (td, J=10.99, 5.80 Hz, 1H), 3.36 (d, J=10.68 Hz, 1H), 3.84 (d, J=10.68 Hz, 1H), 4.59 (s, 1H), 4.69 (d, J=1.83 Hz, 1H), 5.31 (dd, J=6.10, 1.53 Hz, 1H), 7.10 (dd, J=7.93, 1.53 Hz, 1H), 7.25 (s, 1H), 7.89 (d, J=7.93 Hz, 1H).

Example 5b

Preparation of 4-((1R,3aS,5aR,5bR,7aR,11aS,11bR, 13bR)-3a-(hydroxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)benzoic acid

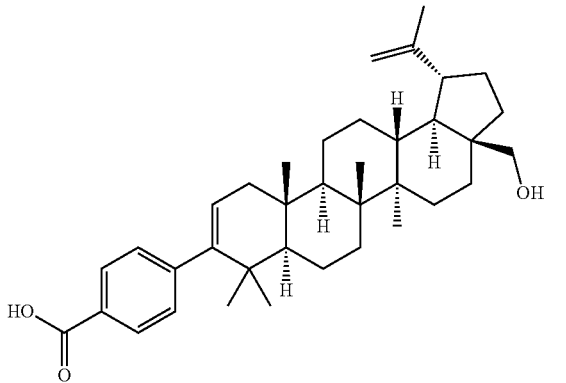

The title compound was prepared by the general method described above using 4-ethoxycarbonylphenylboronic acid as the reactant boronic acid. The product was purified by Biotage flash chromatography using a 0-5% MeOH in dichloromethane gradient followed by crystallization from dioxane and water. The product was isolated as a white solid (12 mg, 0.022 mmol, 29.5% yield over two steps). LCMS: m/e 543.6 (M−H)⁻, 1.82 min (method 1). ¹H NMR (400 MHz, Pyr) δ ppm 1.02 (s, 3H), 1.03 (s, 6H), 1.10 (s, 3H), 1.10 (s, 3H), 1.11-2.02 (m, 18H), 1.82 (s, 3H), 2.09-2.27 (m, 2H), 2.41-2.52 (m, 2H), 2.68 (td, J=10.92, 5.77 Hz, 1H), 3.71 (d, J=10.79 Hz, 1H), 4.14 (d, J=10.79 Hz, 1H), 4.80 (s, 1H), 4.94 (d, J=2.26 Hz, 1H), 5.42 (d, J=4.52 Hz, 1H), 7.42 (d, J=8.03 Hz, 2H), 8.47 (d, J=8.03 Hz, 2H).

Example 5c

Preparation of 5-((1R,3aS,5aR,5bR,7aR,11aS,11bR, 13bR)-3a-(hydroxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)thiophene-2-carboxylic acid

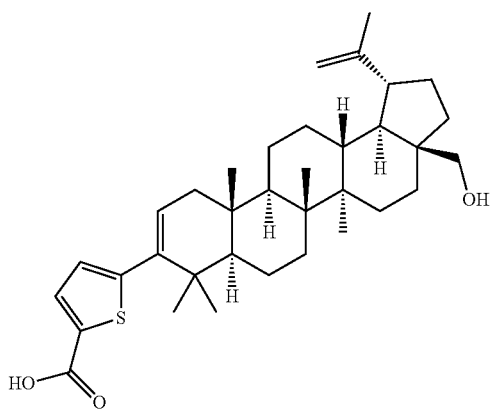

The title compound was prepared by the general method described above using 2-carboxythiophene-5-boronic acid as the reactant boronic acid. The product was purified by crystallization from dioxane and water. The title compound was isolated as an off-white solid (15 mg, 0.027 mmol, 36% yield over two steps). LCMS: m/e 549.5 (M−H)⁻, 1.63 min (method 1). ¹H NMR (400 MHz, Pyr) δ ppm 0.92 (s, 3H), 1.00-2.00 (m, 18H), 1.06 (s, 3H), 1.09 (s, 3H), 1.14 (s, 3H), 1.17 (s, 3H), 1.81 (s, 3H), 2.09-2.27 (m, 2H), 2.40-2.52 (m, 2H), 2.67 (td, J=10.92, 5.77 Hz, 1H), 3.71 (d, J=10.79 Hz, 1H), 4.13 (d, J=10.54 Hz, 1H), 4.80 (s, 1H), 4.94 (d, J=2.26 Hz, 1H), 5.90 (dd, J=6.27, 2.01 Hz, 1H), 7.07 (d, J=3.76 Hz, 1H), 8.05 (d, J=3.76 Hz, 1H).

Example 5d

Preparation of 4-((1R,3aS,5aR,5bR,7aR,11aS,11bR, 13bR)-3a-(hydroxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)thiophene-2-carboxylic acid

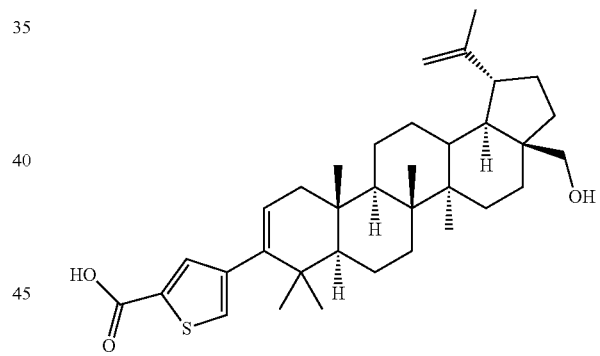

The title compound was prepared by the general method described above using 4-boronothiophene-2-carboxylic acid as the reactant boronic acid. The product was purified by crystallization from dioxane and water followed by Biotage flash chromatography using 0-10% MeOH in dichloromethane with 0.1% HOAc added. The title compound was isolated as a white solid (10 mg, 0.017 mmol, 23% yield over two steps). LCMS: m/e 549.3 (M−H)⁻, 1.55 min (method 1). ¹H NMR (400 MHz, CHLOROFORM-d) δ ppm 0.81-1.79 (m, 24H), 1.03 (s, 3H), 1.10 (br. s., 3H), 1.27 (s, 3H), 1.71 (s, 3H), 1.84-2.15 (m, 4H), 2.37-2.47 (m, 1H), 3.38 (d, J=10.79 Hz, 1H), 3.84 (d, J=10.54 Hz, 1H), 4.61 (s, 1H), 4.71 (s, 1H), 5.44 (br. s., 1H), 7.18 (br. s., 1H), 7.65 (br. s., 1H).

Example 5e

Preparation of 5-((1R,3aS,5aR,5bR,7aR,11aS,13aR, 13bR)-3a-(hydroxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)pyridin-2-ol

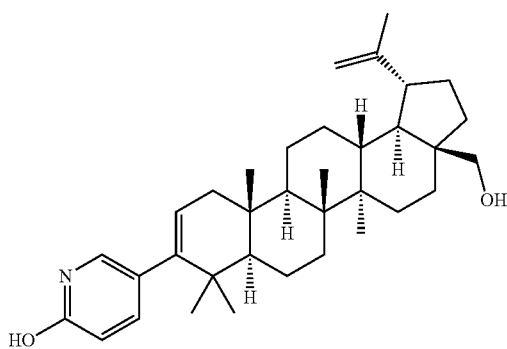

The title compound was prepared following the method described above using 5-(4,4,5,5-tetramethyl-1,3,2-dioxaborolan-2-yl)pyridin-2-ol as the reactant boronic acid. The product was isolated as a white solid (5.46 mg, 33%). LCMS: m/e 518.38 (M+H)$^+$, 5.38 min (method 9). $^1$H NMR (600 MHz, DMSO-D6_CDCl$_3$) ppm 0.88 (s, 3H), 0.91 (s, 3H), 0.93 (s, 3H), 0.99 (s, 3H), 1.07 (s, 3H) 1.00-1.78 (m, 17H), 1.68 (s, 3H), 1.85-1.99 (m, 3H), 2.05 (dd, J=17.28, 6.15 Hz, 1H), 2.35-2.47 (m, 1H), 3.14 (dd, J=10.25, 4.98 Hz, 1H), 3.22 (d, J=5.27 Hz, 1H), 3.53-3.64 (m, 1H), 4.19 (br. s., 1H), 4.56 (br. s., 1H), 4.68 (br. s., 1H), 5.32 (d, J=4.69 Hz, 1H), 6.26 (d, J=9.37 Hz, 1H), 6.96 (br. s., 1H), 7.15-7.30 (m, 1H), 11.46 (br. s., 1H).

Example 5f

Preparation of 2-fluoro-4-((1R,3aS,5aR,5bR,7aR, 11aS,11bR,13aR,13bR)-3a-(hydroxymethyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)phenol

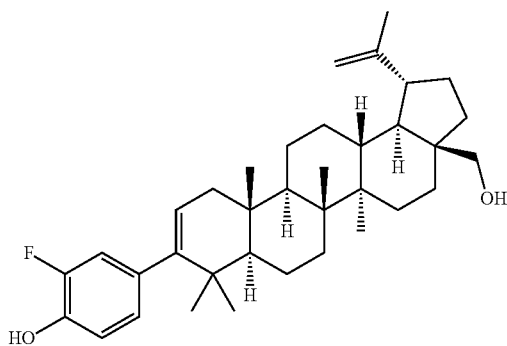

The title compound was prepared following the method described above using 2-fluoro-4-(4,4,5,5-tetramethyl-1,3,2-dioxaborolan-2-yl)phenol as the reactant boronic acid. The product was isolated as a white solid (12.9 mg, 77%). LCMS: m/e 535.46 (M+H)$^+$, 6.27 min (method 9). $^1$H NMR (600 MHz, DMSO-D6_CDCl$_3$) δ ppm 0.89 (s, 3H), 0.91 (s, 3H), 0.94 (s, 3H), 0.99 (s, 3H), 1.07 (s, 3H), 1.01-1.78 (m, 17H), 1.67 (s, 3H), 1.86-1.99 (m, 3H), 2.05 (dd, J=16.99, 6.44 Hz, 1H), 2.38-2.48 (m, 1H), 3.14 (dd, J=9.96, 5.27 Hz, 1H), 3.22 (d, J=5.27 Hz, 1H), 3.59 (dd, J=9.67, 5.57 Hz, 1H), 4.16-4.27 (m, 1H), 4.56 (br. s., 1H), 4.69 (br. s., 1H), 5.24 (d, J=4.69 Hz, 1H), 6.69 (d, J=8.20 Hz, 1H), 6.78 (d, J=12.30 Hz, 1H), 6.84 (t, J=8.79 Hz, 1H), 9.54 (br. s., 1H).

Compound 5g: Preparation of 2-chloro-4-((1R,3aS, 5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)phenol

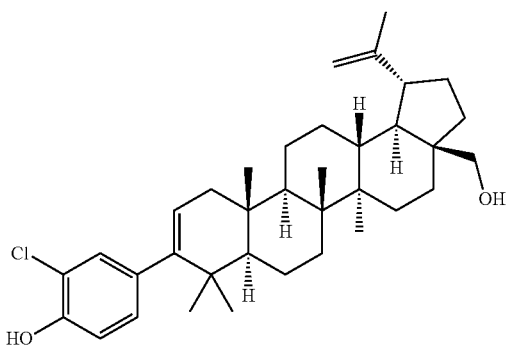

The title compound was prepared following the method described above using 2-chloro-4-(4,4,5,5-tetramethyl-1,3,2-dioxaborolan-2-yl)phenol as the reactant boronic acid. The product was isolated as a white solid (7.56 mg, 45%). LCMS: m/e 551.47 (M−H)$^-$, 6.53 min (method 9). $^1$H NMR (600 MHz, DMSO-D6_CDCl$_3$) δ ppm 0.89 (s, 3H), 0.91 (s, 3H), 0.94 (s, 3H), 0.99 (s, 3H), 1.02-1.78 (m, 17H), 1.08 (s, 3H), 1.68 (s, 3H), 1.86-1.99 (m, 3H), 2.06 (dd, J=16.99, 5.86 Hz, 1H), 2.34-2.47 (m, 1H), 3.14 (dd, J=10.25, 4.98 Hz, 1H), 3.22 (d, J=5.27 Hz, 1H), 3.59 (dd, J=10.25, 4.98 Hz, 1H), 4.19 (br. s., 1H), 4.56 (br. s., 1H), 4.69 (br. s., 1H), 5.23 (d, J=5.27 Hz, 1H), 6.82-6.91 (m, 2H), 6.99 (s, 1H), 9.86 (br. s., 1H).

Compound 5h: Preparation of 4-((1R,3aS,5aR,5bR, 7aR,11aS,11bR,13aR,13bR)-3a-(hydroxymethyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)-3-methylphenol

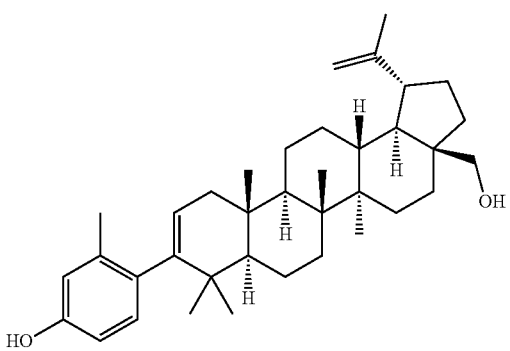

The title compound was prepared following the method described above using 3-methyl-4-(4,4,5,5-tetramethyl-1,3,2-dioxaborolan-2-yl)phenol as the reactant boronic acid. The product was isolated as a white solid (10.42 mg, 62%). LCMS: m/e 531.46 (M+H)+, 6.37 min (method 9). $^1$H NMR (600 MHz, DMSO-D6_CDCl$_3$) δ ppm 1.00 (s, 9H), 1.08 (s, 6H), 1.04-1.81 (m, 17H), 1.68 (s, 3H), 1.86-2.00 (m, 3H), 2.02-2.10 (m, 1H), 2.14 (s, 3H), 2.42 (d, J=6.44 Hz, 1H), 3.14 (dd, J=10.55, 5.27 Hz, 1H), 3.22 (d, J=5.27 Hz, 1H), 3.53-3.66 (m, 1H), 4.19 (br. s., 1H), 4.56 (br. s., 1H), 4.69 (s, 1H), 5.15 (d, J=5.27 Hz, 1H), 6.49 (d, J=8.20 Hz, 1H), 6.57 (br. s., 1H), 6.79 (d, J=7.03 Hz, 1H), 8.98 (br. s., 1H).

Example 5i

Preparation of N-(4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)methanesulfonamide

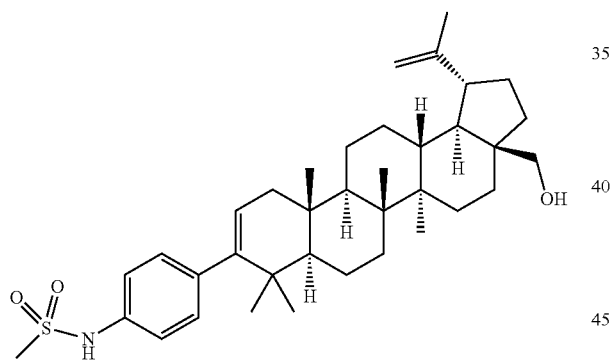

The title compound was prepared following the method described above using 4-(methylsulfonamido)phenylboronic acid as the reactant boronic acid. The product was isolated as a white solid (3.97 mg, 23%). LCMS: m/e 592.78 (M−H)−, 5.76 min (method 9). $^1$H NMR (600 MHz, DMSO-D6_CDCl$_3$) δ ppm 0.90 (s., 3H), 0.91 (s., 3H), 0.96 (s, 3H), 1.00 (s, 3H), 1.08 (s, 3H), 0.97-1.78 (m, 17H), 1.68 (s, 3H), 1.85-2.00 (m, 3H), 2.07 (dd, J=16.70, 6.15 Hz, 1H), 2.37-2.47 (m, 1H), 2.97 (s, 3H), 3.14 (dd, J=10.55, 5.27 Hz, 1H), 3.22 (d, J=5.27 Hz, 1H), 3.55-3.64 (m, 1H), 4.19 (br. s., 1H), 4.56 (br. s., 1H), 4.69 (br. s., 1H), 5.23 (d, J=4.69 Hz, 1H), 7.05 (d, J=8.79 Hz, 2H), 7.13 (d, J=8.79 Hz, 2H), 9.61 (br. s., 1H).

Compound 5j: Preparation of 4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzenesulfonamide

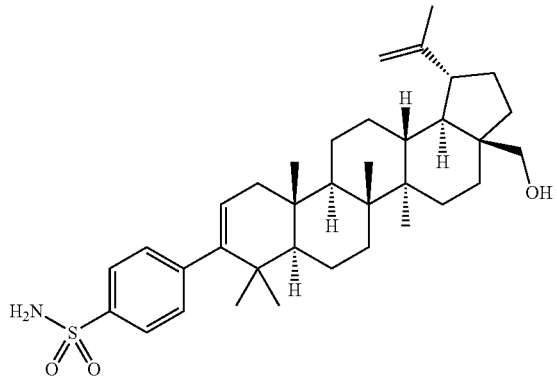

The title compound was prepared following the method described above using 4-(N-cyclopropylsulfamoyl)phenylboronic acid as the reactant boronic acid. White solid (1.87 mg, 12%). LCMS: m/e 578.75 (M−H)−, 5.19 min (method 9). $^1$H NMR (600 MHz, DMSO-D6_CDCl$_3$) δ ppm 0.92 (br. s., 6H), 0.98 (s, 3H), 1.00 (s, 3H), 1.09 (s, 3H), 1.01-1.77 (m, 17H), 1.68 (s, 3H), 1.86-2.01 (m, 3H), 2.10 (dd, J=16.70, 6.15 Hz, 1H), 2.37-2.46 (m, 1H), 3.09-3.18 (m, 1H), 3.22 (d, J=5.27 Hz, 1H), 3.53-3.64 (m, 1H), 4.20 (br. s., 1H), 4.56 (br. s., 1H), 4.69 (br. s., 1H), 5.27 (d, J=4.69 Hz, 1H), 7.24-7.33 (m, 4H), 7.77 (d, J=7.62 Hz, 2H).

Example 5k

Preparation of 3-fluoro-4-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)benzoic acid

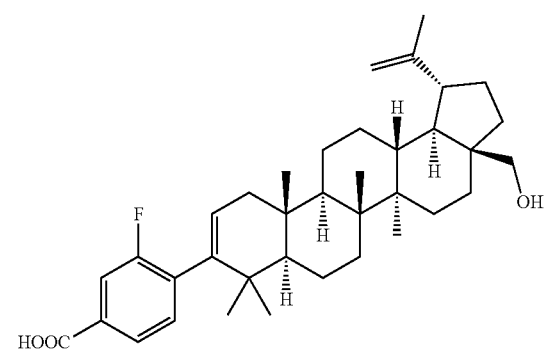

The title compound was prepared following the method described above using 4-(ethoxycarbonyl)-2-fluorophenylboronic acid as the reactant boronic acid. The product was isolated as a white solid (10.57 mg, 25%). LCMS: m/e 563.45 (M+H)$^+$, 14.26 min (method 8). $^1$H NMR (600 MHz, DMSO-D6_CDCl$_3$) δ ppm 0.88 (s, 3H), 0.94 (s, 3H), 0.99 (s, 3H), 1.01 (s, 3H), 1.09 (s, 3H), 1.01-1.79 (m, 17H), 1.68 (s, 3H), 1.84-2.02 (m, 3H), 2.11 (dd, J=17.28, 6.74 Hz, 1H), 2.36-2.47 (m, 1H), 3.14 (d, J=9.37 Hz, 1H), 3.22-3.26 (m, 1H), 3.59 (d, J=10.55 Hz, 1H), 4.18 (br. s., 1H), 4.56 (br. s., 1H), 4.69 (s, 1H), 5.33 (d, J=5.27 Hz, 1H), 7.22 (t, J=7.62 Hz, 1H), 7.61 (d, J=8.79 Hz, 1H), 7.71 (d, J=7.62 Hz, 1H).

Example 5l

Preparation of ((1R,3aS,5aR,5bR,7aR,11aS,11bR, 13aR,13bR)-9-(4-(2H-tetrazol-5-yl)phenyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-3a-yl) methanol

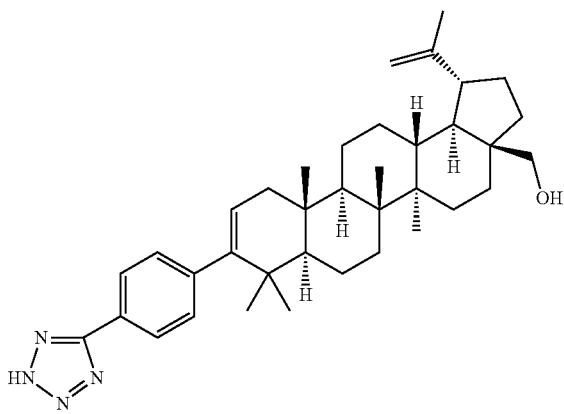

The title compound was prepared following the method described above using 4-(2H-tetrazol-5-yl)phenylboronic acid as the reactant boronic acid. The product was isolated as a white solid (0.66 mg, 1.6%). LCMS: m/e 569.51 (M+H)$^+$, 14.28 min (method 8).

Example 5m

Preparation of 2-fluoro-4-((1R,3aS,5aR,5bR,7aR, 11aS,11bR,13aR,13bR)-3a-(hydroxymethyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

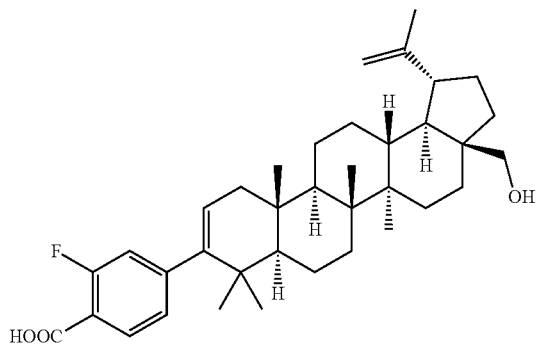

The title compound was prepared following the method described above using 4-borono-2-fluorobenzoic acid as the reactant boronic acid. The product was isolated as a white solid (0.9 mg, 2%). LCMS: m/e 563.35 (M+H)$^+$, 14.19 min (method 8).

Example 5n

Preparation of 3-chloro-4-((1R,3aS,5aR,5bR,7aR, 11aS,11bR,13aR,13bR)-3a-(hydroxymethyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

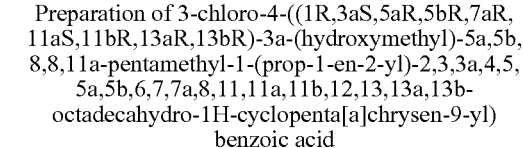

The title compound was prepared following the method described above using 4-borono-3-chlorobenzoic acid as the reactant boronic acid. The product was isolated as a white solid (10.37 mg, 24%). LCMS: m/e 579.67 (M+H)$^+$, 14.44 min (method 8). $^1$H NMR (600 MHz, DMSO-D6_CDCl$_3$) δ ppm 0.92-0.98 (m, 3H), 0.99-1.04 (m, 6H), 1.03-1.08 (m, 3H), 1.09 (s, 3H), 1.11-1.81 (m, 17H), 1.68 (s, 3H), 1.85-2.02 (m, 3H), 2.14 (dd, J=16.70, 5.57 Hz, 1H), 2.38-2.47 (m, 1H), 3.14 (d, J=6.44 Hz, 1H), 3.23-3.27 (m, 1H), 3.59 (d, J=9.96 Hz, 1H), 4.18 (br. s., 1H), 4.56 (s., 1H), 4.69 (s., 1H), 5.31 (d, J=5.27 Hz, 1H), 7.32 (d, J=6.45 Hz, 1H), 7.82 (d, J=8.20 Hz, 1H), 7.94 (s, 1H).

Example 5o

Preparation of 4-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-2-methoxybenzoic acid

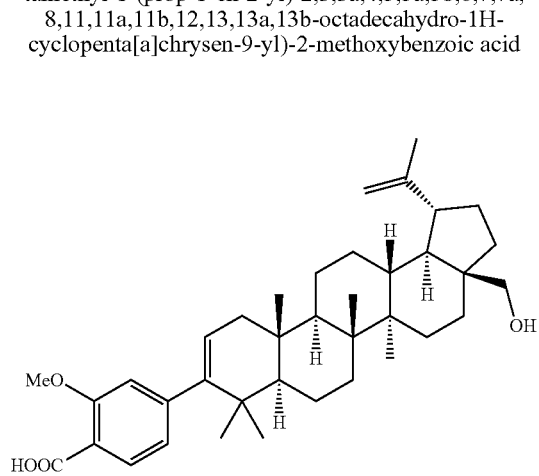

The title compound was prepared following the method described above using 4-borono-2-methoxybenzoic acid as the reactant boronic acid. The product was isolated as a white solid (0.9 mg, 2%). LCMS: m/e 575.50 (M+H)+, 14.29 min (method 8).

Example 5p

Preparation of 2-hydroxy-4-((1R,3aS,5aR,5bR,7aR, 11aS,11bR,13aR,13bR)-3a-(hydroxymethyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoic acid

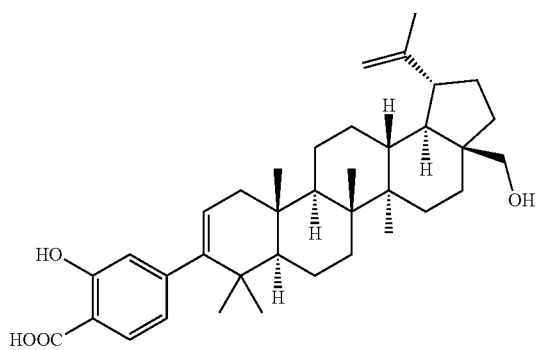

The title compound was prepared following the method described above using 3-hydroxy-4-(methoxycarbonyl)phenylboronic acid as the reactant boronic acid. The product was isolated as a white solid (17.6 mg, 42%). LCMS: m/e 561.39 (M+H)+, 14.15 min (method 8). $^1$H NMR (600 MHz, DMSO-D6_CDCl$_3$) δ ppm 0.94 (s, 6H), 0.96 (s, 3H), 1.00 (s, 3H), 1.08 (s, 3H), 1.02-1.79 (m, 17H), 1.68 (s, 3H), 1.85-2.02 (m, 3H), 2.09 (dd, J=15.82, 4.69 Hz, 1H), 2.38-2.46 (m, 1H), 3.11-3.18 (m, 1H), 3.20-3.22 (m, 1H), 3.59 (d, J=7.62 Hz, 1H), 4.18 (br. s., 1H), 4.56 (br. s., 1H), 4.69 (br. s., 1H), 5.27 (br. s., 1H), 6.63 (br. s., 2H), 7.68 (d, J=7.03 Hz, 1H).

Example 5q

Preparation of 5-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)pyrimidine-2-carboxylic acid

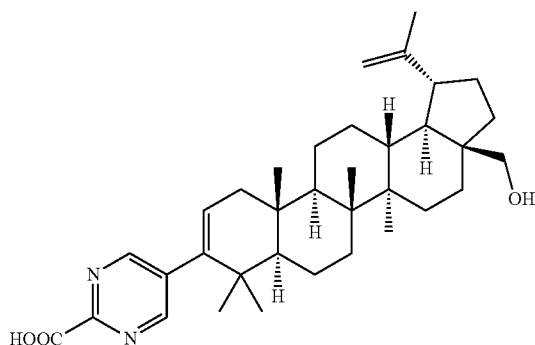

The title compound was prepared following the method described above using 2-cyanopyrimidin-5-ylboronic acid as the reactant boronic acid. The product was isolated as a white solid (1.13 mg, 3%). LCMS: m/e 547.38 (M+H)+, 13.57 min (method 8).

Example 5r

Preparation of 4-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-3-methylbenzoic acid

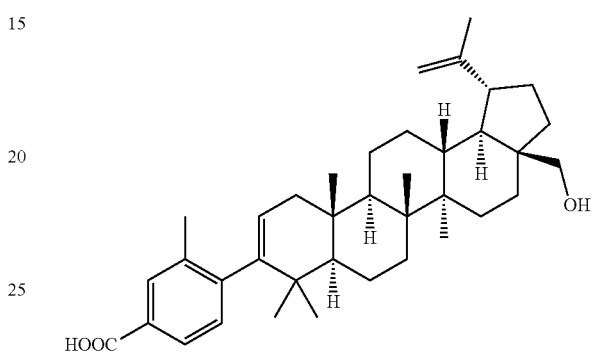

The title compound was prepared following the method described above using 4-(methoxycarbonyl)-2-methylphenylboronic acid as the reactant boronic acid. The product was isolated as a white solid (13 mg, 20%). LCMS: m/e 557.64 (M−H)−, 2.22 min (method 7). $^1$H NMR (500 MHz, CHLOROFORM-d) δ ppm 0.99 (s, 3H), 1.02 (s, 6H), 1.06 (d, J=5.49 Hz, 3H), 1.09 (s, 3H), 1.11-1.78 (m, 15H), 1.69 (s, 3H), 1.83-1.90 (m, 2H), 1.90-2.02 (m, 3H), 2.11 (dd, J=17.24, 5.65 Hz, 1H), 2.31 (s, 3H), 2.36-2.46 (m, 1H), 3.35 (d, J=10.68 Hz, 1H), 3.66-3.68 (m, 1H), 3.83 (d, J=11.60 Hz, 1H), 4.59 (s., 1H), 4.69 (d, J=1.83 Hz, 1H), 5.24 (d, J=4.58 Hz, 1H), 7.14 (d, J=8.24 Hz, 1H), 7.79 (d, J=7.63 Hz, 1H), 7.91 (s., 1H).

Example 5s

Preparation of 4-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-2-(trifluoromethyl) benzoic acid

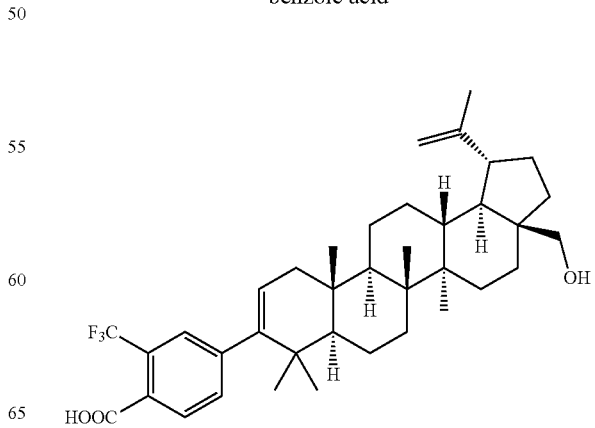

The title compound was prepared following the method described above using 4-borono-2-(trifluoromethyl)benzoic acid as the reactant boronic acid. The product was isolated as a white solid (28 mg, 89%). LCMS: m/e 611.39 (M–H)⁻, 2.2 min (method 7). ¹H NMR (500 MHz, DMSO-d₆) δ 7.32 (d, J=7.9 Hz, 1H), 7.23 (s, 1H), 7.17 (s, 1H), 5.24 (d, J=4.6 Hz, 1H), 4.68 (d, J=2.4 Hz, 1H), 4.55 (s, 1H), 3.55 (d, J=10.7 Hz, 1H), 3.10 (d, J=10.7 Hz, 1H), 2.46-2.36 (m, 1H), 2.06 (dd, J=17.2, 6.3 Hz, 1H), 1.95-1.01 (m, 21H), 1.65 (s, 3H), 1.05 (s, 3H), 0.98 (s, 4H), 0.94 (s, 3H), 0.89 (s, 3H), 0.87 (s, 3H).

Example 5t

Preparation of 4-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)phthalic acid

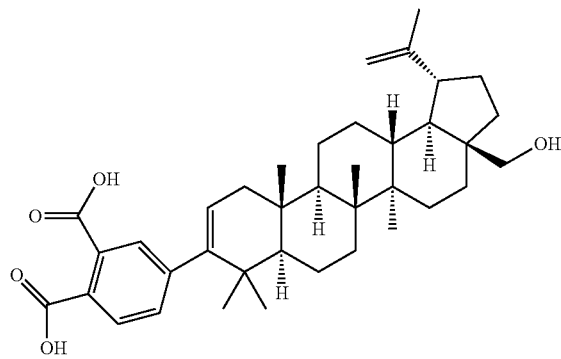

The title compound was prepared following the method described above using 4-boronophthalic acid
as the reactant boronic acid. The product was isolated as a white solid (3 mg, 42%). LCMS: m/e 587.4 (M–H)⁻, 2.25 min (method 7). ¹H NMR (500 MHz, DMSO-d₆) δ 8.08 (d, J=8.2 Hz, 1H), 7.92 (d, J=2.1 Hz, 1H), 7.22 (dd, J=8.1, 2.0 Hz, 1H), 5.24 (d, J=4.9 Hz, 1H), 4.69 (d, J=2.7 Hz, 1H), 4.55 (s, 1H), 3.56 (d, J=10.4 Hz, 1H), 3.10 (d, J=11.3 Hz, 1H), 2.48-2.39 (m, 1H), 2.15-2.03 (m, 1H), 1.96-0.92 (m, 21H), 1.65 (s, 3H), 1.06 (s, 3H), 0.98 (s, 3H), 0.95 (s, 3H), 0.89 (s, 6H).

Example 5u

Preparation of 6-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)nicotinic acid

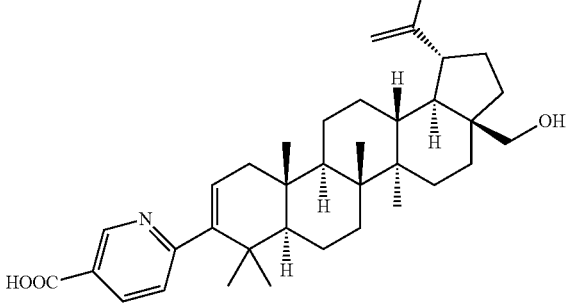

The title compound was prepared following the method described above using 5-(methoxycarbonyl)pyridin-2-ylboronic acid as the reactant boronic acid. The product was isolated as a white solid (2.1 mg, 59%). LCMS: m/e 544.32 (M–H)⁻, 2.11 min (method 7). ¹H NMR (500 MHz, DMSO-d₆) δ 8.87 (d, J=1.2 Hz, 1H), 8.04 (dd, J=7.9, 1.8 Hz, 1H), 7.20 (d, J=7.9 Hz, 1H), 5.57 (d, J=4.3 Hz, 1H), 4.69 (d, J=2.1 Hz, 1H), 4.55 (s, 1H), 3.55 (d, J=11.0 Hz, 1H), 3.10 (d, J=10.7 Hz, 1H), 2.46-2.34 (m, 1H), 2.13 (dd, J=17.4, 6.1 Hz, 1H), 1.92-1.07 (m, 21H), 1.65 (s, 3H), 1.13 (s, 3H), 1.05 (s, 3H), 0.98 (d, J=2.1 Hz, 6H), 0.90 (s., 3H).

Preparation of (1R,3aS,5aR,5bR,7aR,11aS,13aR, 13bR)-benzyl 9-(4-(chlorocarbonyl)phenyl)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysene-3a-carboxylate

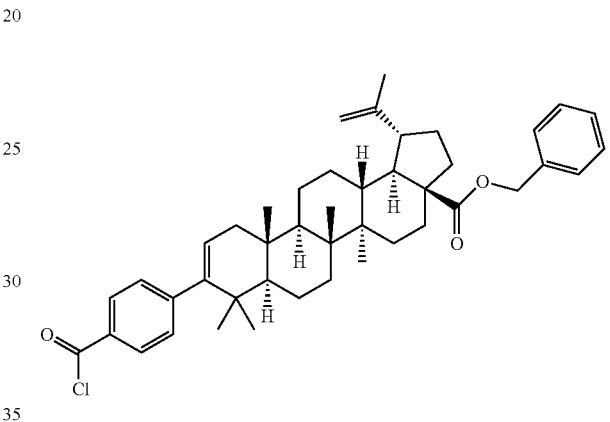

A mixture of (1R,3aS,5aR,5bR,7aR,11aR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a, 11b,12,13,13a,13b-octadecahydro-1H-cyclopenta[a] chrysene-3a-carboxylate (300 mg, 0.443 mmol), 4-boronobenzoic acid (88 mg, 0.532 mmol), Pd(Ph₃P)₄ (15.36 mg, 0.013 mmol) and Na₂CO₃ (141 mg, 1.330 mmol) in Water (1 mL) and DME (1 mL) was heated up at 100° C. for 2 hours. LCMS indicated the formation of the precursor of the desired product. The reaction mixture was quenched with distilled water (5 mL) and extracted with ethyl acetate (3×5 mL). The extracts were combined and dried over Na₂SO₄. The organic solution was filtered and concentrated under reduced pressure to provide the crude precursor of the desired product. LCMS: m/e 647.59 (M–H)⁻, 2.44 min (method 7). The residue was dissolved in CH₂Cl₂ (1.000 mL), then SOCl₂ (0.647 mL, 8.86 mmol) was added. The reaction mixture was refluxed for 17 hours and concentrated under reduced pressure. The residue was dried under vacuum for 3 hours to provide the desired product (1R,3aS,5aR,5bR,7aR,11aS, 13aR,13bR)-benzyl 9-(4-(chlorocarbonyl)phenyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylate as yellow oil (120 mg,

Example 6a

Preparation of (1R,3aS,5aR,5bR,7aR,11aS,13aR, 13bR)-9-(4-(isopropylsulfonylcarbamoyl)phenyl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysene-3a-carboxylic acid

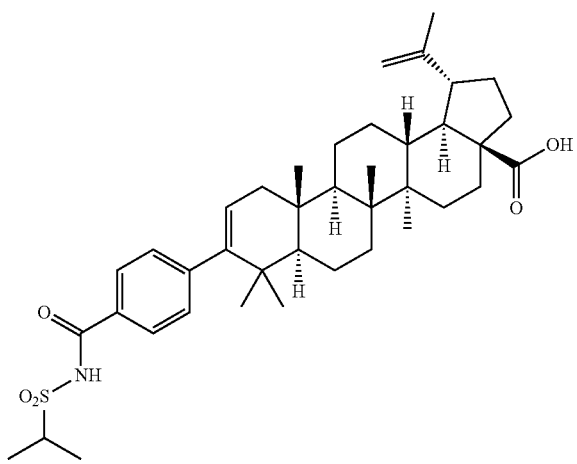

To a mixture of propane-2-sulfonamide (18.46 mg, 0.150 mmol), DMAP (0.915 mg, 7.49 μmol) and Hunig's Base (0.065 mL, 0.375 mmol) in DME (2 mL) was added (1R,3aS, 5aR,5bR,7aR,11aS,13aR,13bR)-benzyl 9-(4-(chlorocarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (50 mg, 0.075 mmol). The reaction mixture was stirred for 16 hours. LCMS indicated the formation of the desired product. The reaction mixture was quenched with distilled water, extracted with ethyl acetate and concentrated under reduced pressure to give crude intermediate (1R,3aS,5aR,5bR,7aR, 11aS,13aR,13bR)-benzyl 9-(4-(isopropylsulfonylcarbamoyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate as a yellow solid. LCMS: m/e 754.60 (M+H)$^+$, 2.36 min (method 7). To this intermediate (50 mg, 0.066 mmol) in EtOAc (2 mL) and MeOH (2.00 mL) was added 10% Pd/C (21.17 mg, 0.020 mmol). The reaction mixture was hydrogentated using a Parr shaker at 40 Psi for 17 hours. LCMS indicated the reaction was completed. The reaction mixture was filtered through a pad of celite and concentrated under reduced. The residue was purified by prep HPLC to provide the desired product, (1R,3aS,5aR,5bR,7aR,11aS,13aR, 13bR)-9-(4-(isopropylsulfonylcarbamoyl)phenyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid, as a white solid (12 mg, 26%). LCMS: m/e 664.48 (M+H)$^+$, 2.18 min (method 7). $^1$H NMR (500 MHz, CHLOROFORM-d) δ ppm 0.91 (s, 6H), 0.96 (s, 3H), 1.00 (d, J=4.27 Hz, 6H), 1.18-1.27 (m, 8H), 1.35-1.55 (m, 13H), 1.60-1.75 (m, 5H), 1.94-2.03 (m, 2H), 2.07-2.14 (m, 1H), 2.22-2.31 (m, 2H), 2.97-3.07 (m, 1H), 3.98-4.08 (m, 1H), 4.61 (s, 1H), 4.74 (s, 1H), 5.28 (d, J=4.88 Hz, 1H), 7.23-7.25 (m, 2H), 7.74 (d, J=8.24 Hz, 2H).

Example 6b

Preparation of (1R,3aS,5aR,5bR,7aR,11aS,13aR, 13bR)-5a,5b,8,8,11a-pentamethyl-9-(4-(methylsulfonylcarbamoyl)phenyl)-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxylic acid

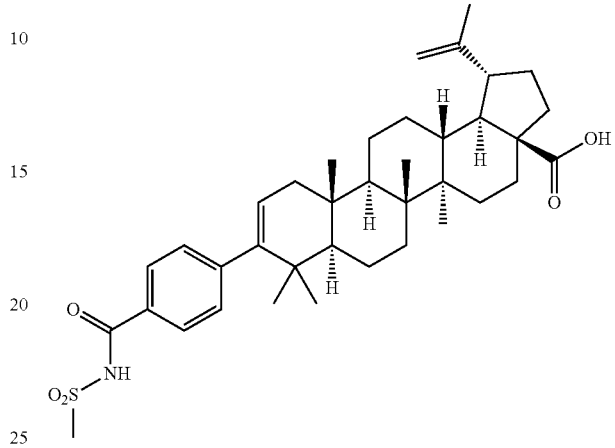

The title compound was prepared from the procedure described above for (1R,3aS,5aR,5bR,7aR,11aS,13aR, 13bR)-benzyl 9-(4-(chlorocarbonyl)phenyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysene-3a-carboxylate using methanesulfonamide as the reactant sulfonamide. The title compound was isolated as a white solid (3.2 mg, 7%). LCMS: m/e 636.51 (M+H)$^+$, 2.13 min (method 7). $^1$H NMR (500 MHz, DMSO-D6) δ ppm 0.88 (d, J=3.05 Hz, 6H), 0.94 (s, 6H), 0.98 (s, 3H), 1.11-1.62 (m, 15H), 1.63-1.72 (m, 5H), 1.77-1.88 (m, 2H), 2.03-2.17 (m, 2H), 2.24-2.35 (m, 1H), 2.97 (d, J=4.58 Hz, 1H), 3.57 (s, 3H), 4.58 (s, 1H), 4.71 (d, J=1.83 Hz, 1H), 5.23 (d, J=4.58 Hz, 1H), 7.17 (d, J=8.24 Hz, 2H), 7.86 (d, J=8.24 Hz, 2H), 12.03 (s, 1H), 12.10 (br. s., 1H).

Example 7

Preparation of (1R,3aS,5aR,5bR,7aR,11aS,11bR, 13aR,13bR)-9-(4-(methoxycarbonyl)phenyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysene-3a-carboxylic acid

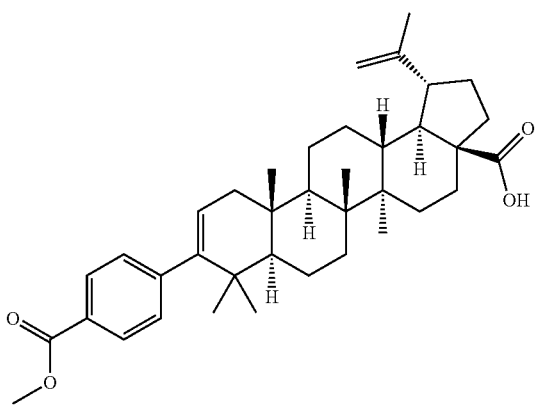

To solution of (1R,3aS,5aR,5bR,7aR,11aS,11bR,13aR, 13bR)-tert-butyldimethylsilyl 9-(4-(methoxycarbonyl)phenyl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylate (3.12 g, 4.54 mmol) in Dioxane (25 mL) was added TBAF (75% wt in water) (2.375 g, 6.81 mmol). The mixture was stirred at rt for 4 h then was diluted with 1N HCl (25 mL) and water (5 mL) and extracted with dichloromethane (3×100 mL). The combined organic layers were dried with $Na_2SO_4$, filtered, and partially concentrated under reduced pressure to a volume of 10 mL. To the partially concentrated mixture was added 1N HCl (50 mL). The solids that formed were collected by filtration and were washed with water. The expected product, (1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysene-3a-carboxylic acid (2.58 g, 4.50 mmol, 99% yield), was isolated as a white solid. LCMS: m/e 571.47 (M–H)⁻, 3.60 min (method 7). $^1$H NMR (500 MHz, CHLOROFORM-d) δ ppm 0.89-1.79 (m, 17H), 0.91 (s, 6H), 0.98 (s, 3H), 1.00 (br. s., 3H), 1.01 (br. s., 3H), 1.70 (s, 3H), 1.94-2.06 (m, 2H), 2.10 (dd, J=17.09, 6.10 Hz, 1H), 2.21-2.33 (m, 2H), 2.99-3.07 (m, 1H), 3.90 (s, 3H), 4.62 (br. s., 1H), 4.75 (s, 1H), 5.26-5.32 (m, 1H), 7.18 (d, J=8.24 Hz, 2H), 7.92 (d, J=8.24 Hz, 2H), 9.80 (br. s., 1H).

Preparation of ethyl 3-((1R,3aS,5aR,5bR,7aR,11aS, 11bR,13aR,13bR)-3a-(benzoyloxymethyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1H-pyrazole-5-carboxylate

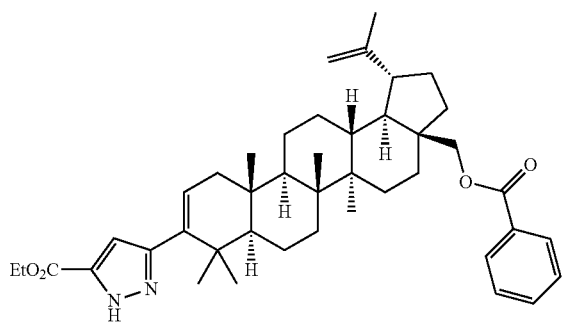

To a sealable vial containing ethyl 3-(tributylstannyl)-1H-pyrazole-5-carboxylate (0.052 g, 0.122 mmol) was added ((1R,3aS,5aR,5bR,7aR,11aR,11bR,13aR,13bR)-5a,5b,8,8, 11a-pentamethyl-1-(prop-1-en-2-yl)-9-(trifluoromethylsulfonyloxy)-2,3,3a,4,5,5a,5b,6,7,7a,8,11,11a,11b,12,13,13a, 13b-octadecahydro-1H-cyclopenta[a]chrysen-3a-yl)methyl benzoate (0.075 g, 0.111 mmol), lithium chloride (0.014 g, 0.332 mmol), and tetrakis(triphenylphosphine)palladium(0) (6.40 mg, 5.54 μmol). The mixture was diluted with 1,4-Dioxane (2 mL) and was flushed with $N_2$. The vial was sealed and heated to 85° C. for 15.5 h. The mixture was cooled to rt, was diluted with water (4 mL) and was extracted with dichloromethane (3×4 mL). The combined organic layers were dried with $Na_2SO_4$. The drying agent was removed by filtration and the filtrate was concentrated under reduced pressure. The residue purified by Biotage flash chromatography using a 0-25% EtOAc in hexanes gradient. The fractions containing the expected product were combined and concentrated under reduced pressure to give ethyl 3-((1R,3aS,5aR,5bR,7aR, 11aS,11bR,13aR,13bR)-3a-(benzoyloxymethyl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)-1H-pyrazole-5-carboxylate (0.070 g, 0.105 mmol, 95% yield) as a white solid. LCMS: m/e 665.66 (M–H)⁻, 2.74 min (method 1). $^1$H NMR (500 MHz, CHLOROFORM-d) δ ppm 0.85-1.84 (m, 21H), 0.91 (s, 3H), 1.02 (s, 3H), 1.03 (br. s., 3H), 1.05 (s, 3H), 1.10 (s, 3H), 1.71 (s, 3H), 1.89-2.07 (m, 3H), 2.15 (dd, J=17.70, 6.41 Hz, 1H), 2.53 (td, J=11.06, 5.95 Hz, 1H), 4.11 (d, J=10.99 Hz, 1H), 4.38 (q, J=7.02 Hz, 2H), 4.52 (d, J=10.07 Hz, 1H), 4.61 (s, 1H), 4.72 (d, J=1.53 Hz, 1H), 5.75 (d, J=4.58 Hz, 1H), 6.73 (s, 1H), 7.44 (t, J=7.78 Hz, 2H), 7.55 (t, J=7.32 Hz, 1H), 8.05 (d, J=7.02 Hz, 2H).

Example 8

Preparation of 3-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-1H-pyrazole-5-carboxylic acid

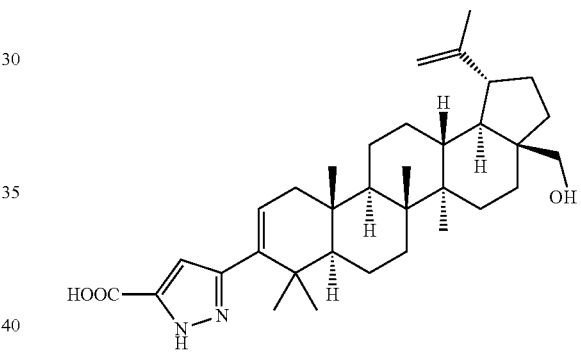

To a solution of ethyl 3-((1R,3aS,5aR,5bR,7aR,11aS, 11bR,13aR,13bR)-3a-(benzoyloxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)-1H-pyrazole-5-carboxylate (0.07 g, 0.105 mmol) in 1,4-Dioxane (4 mL) was added Water (1 mL) and lithium hydroxide monohydrate (0.085 g, 2.026 mmol). The mixture was heated to 75° C. for 18.25 h, was cooled to rt, and was quenched with 1N HCl (7 mL). The mixture was extracted with dichloromethane (4×7 mL) and the combined organic layers were dried with $Na_2SO_4$. The drying agent was removed by filtration and the filtrate was concentrated under reduced pressure. Purification was accomplished by crystallization from dioxane and water to give 3-((1R,3aS,5aR,5bR, 7aR,11aS,11bR,13aR,13bR)-3a-(hydroxymethyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)-1H-pyrazole-5-carboxylic acid (0.03 g, 0.052 mmol, 49.2% yield) as a white solid. LCMS: m/e 533.60 (M–H)⁻, 1.24 min (method 1). $^1$H NMR (500 MHz, Pyr) δ ppm 0.86 (t, J=7.48 Hz, 3H), 0.95 (s, 3H), 1.06 (s, 6H), 1.06-1.99 (m, 22H), 1.80 (s, 3H), 2.14-2.24 (m, 2H), 2.40-2.51 (m, 2H), 2.65 (dt, J=10.99, 5.49 Hz, 1H), 3.69 (d, J=10.68 Hz, 1H), 4.12 (d, J=10.68 Hz, 1H), 4.79 (s, 1H), 4.93 (d, J=2.14 Hz, 1H), 6.13 (br. s., 1H), 7.33 (s, 1H).

89

Preparation of ethyl 5-((1R,3aS,5aR,5bR,7aR,11aS, 11bR,13aR,13bR)-3a-(benzoyloxymethyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) isoxazole-3-carboxylate

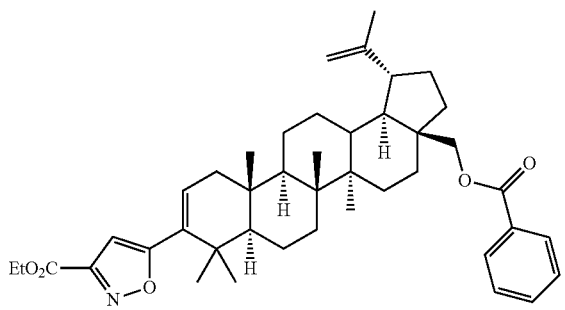

To a sealable vial containing ethyl 5-(tributylstannyl)isoxazole-3-carboxylate (0.052 g, 0.122 mmol) was added ((1R, 3aS,5aR,5bR,7aR,11aR,11bR,13aR,13bR)-5a,5b,8,8,11a-pentamethyl-1-(prop-1-en-2-yl)-9-(trifluoromethylsulfonyloxy)-2,3,3a,4,5,5a,5b,6,7,7a,8,11, 11a,11b,12,13,13a,13b-octadecahydro-1H-cyclopenta[a] chrysen-3a-yl)methyl benzoate (0.075 g, 0.111 mmol), lithium chloride (0.014 g, 0.332 mmol), and tetrakis(triphenylphosphine)palladium(0) (6.40 mg, 5.54 μmol). The mixture was diluted with 1,4-Dioxane (2 mL) and was flushed with $N_2$. The vial was sealed and heated to 85° C. After 15.5 h of heating, the mixture was cooled to rt, was diluted with water (4 mL), and was extracted with dichloromethane (3×4 mL). The combined organic layers were dried over $Na_2SO_4$. The drying agent was removed by filtration and the filtrate was concentrated under reduced pressure. The residue was purified by Biotage flash chromatography using a 0-10% EtOAc in hexanes gradient. The fractions containing the expected product were combined and concentrated under reduced pressure. Ethyl 5-((1R,3aS,5aR,5bR,7aR,11aS, 11bR,13aR,13bR)-3a-(benzoyloxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)isoxazole-3-carboxylate was isolated as an off-white foam (0.015 g total mass, 0.022 mmol, 20.3% yield). LCMS: m/e 668.53 (M+H)$^+$, 3.11 min (method 1).

Example 9

Preparation of 5-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)isoxazole-3-carboxylic acid

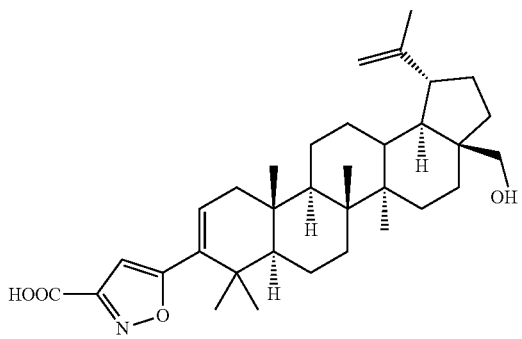

90

To a solution of ethyl 5-((1R,3aS,5aR,5bR,7aR,11aS, 11bR,13aR,13bR)-3a-(benzoyloxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)isoxazole-3-carboxylate (0.015 g, 0.022 mmol) in 1,4-Dioxane (2 mL) was added Water (0.5 mL) and Lithium hydroxide monohydrate (0.17 g, 4.05 mmol). The mixture was heated to 75° C. After 3.5 h the mixture was cooled to rt and was diluted with 1N HCl (7 mL) then was extracted with dichloromethane (4×7 mL). The combined organic layers were dried with $Na_2SO_4$. The drying agent was removed by filtration and the filtrate was concentrated under reduced pressure. The residue was purified by crystallization using dioxane, water, and methanol. The expected product, 5-((1R,3aS,5aR,5bR,7aR,11aS,11bR,13aR,13bR)-3a-(hydroxymethyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)isoxazole-3-carboxylic acid (4 mg, 7.17 mmol, 31.9% yield), was isolated as a white solid. LCMS: m/e 536.35 (M+H)$^+$, 2.03 min (method 7). $^1$H NMR (500 MHz, Pyr) δ ppm 0.87 (s, 3H), 0.96-1.88 (m, 20H), 1.04 (s, 3H), 1.05 (s, 3H), 1.17 (s, 3H), 1.21 (s, 3H), 1.81 (s, 3H), 2.14-2.27 (m, 1H), 2.39-2.53 (m, 1H), 2.59-2.74 (m, 1H), 3.70 (d, J=10.99 Hz, 1H), 4.12 (d, J=10.99 Hz, 1H), 4.80 (br. s., 1H), 4.94 (s, 1H), 6.40 (d, J=6.41 Hz, 1H), 7.08 (s, 1H).

Example 10

Preparation of 4-((1S,3aS,5aR,5bR,7aR,11aS,11bR, 13aR,13bR)-3a-(hydroxymethyl)-1-isopropyl-5a,5b, 8,8,11a-pentamethyl-2,3,3a,4,5,5a,5b,6,7,7a,8,11, 11a,11b,12,13,13a,13b-octadecahydro-1H-cyclopenta[a]chrysen-9-yl)benzoic acid

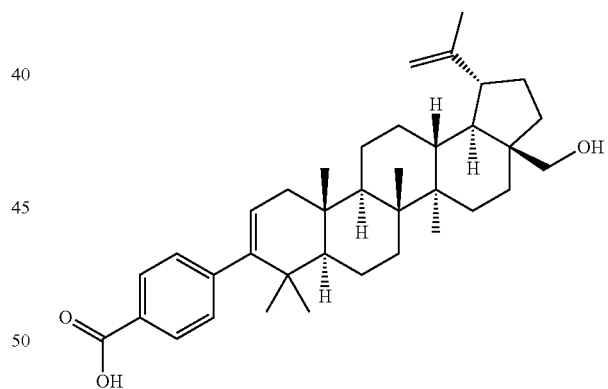

A mixture of 4-((1R,3aS,5aR,5bR,7aR,11aS,11bR,13aR, 13bR)-3a-(hydroxymethyl)-5a,5b,8,8,11a-pentamethyl-1-(prop-1-en-2-yl)-2,3,3a,4,5,5a,5b,6,7,7a, 8,11,11a,11b,12, 13,13a,13b-octadecahydro-1H-cyclopenta[a]chrysen-9-yl) benzoic acid (50 mg, 0.092 mmol) and a catalytic amount of Pd/C (9.77 mg, 0.092 mmol) was dissolved in a mixture of methanol (1 mL) and ethyl acetate (1 mL) and stirred under 1 ATM of $H_2$ for 24 hours. LCMS indicated the completion of the reaction. The reaction mixture was filtered to remove the catalyst. The solution was concentrated in vacuo and the residue was purified using reverse phase prep HPLC to afford the title compound as a white solid. LCMS: m/e 529.29 (M+H−H$_2$O)$^+$, 0.15 min (method 1). $^1$H NMR (500 MHz, CHLOROFORM-d) δ ppm $^1$H NMR (500 MHz, CHLORO- FORM-d) δ ppm 0.80 (d, 3H), 0.88 (d, J=6.71 Hz, 3H), 0.97 (s, 6H), 1.02 (s, 6H), 1.12 (s, 3H), 1.18-2.23 (m, 24H), 3.36 (d, J=10.99 Hz, 1H), 3.84 (d, J=10.68 Hz, 1H), 5.27-5.42 (m, 1H), 7.26 (d, J=7.93 Hz, 2H), 8.01 (d, J=8.24 Hz, 2H).

Example 11

Preparation of methyl 4-((1R,3aS,5aR,5bR,7aR, 11aS,11bR,13aR,13bR)-3a-(hydroxymethyl)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) benzoate c
Step 1: Betuline (2 g, 4.52 mmol) was dissolved in DMF (13 ml) and treated with IMIDAZOLE (0.923 g, 13.55 mmol) and TBDPS-Cl (2.437 ml, 9.49 mmol) at 50° C. for 18 h. TLC showed the reaction was complete. The reaction mixture was cooled to rt and diluted with EtOAc and water. The organic layer was separated dried over sodium sulfate, filtered and concentrated in vacuo. The crude was purified using silica gel chromatography (0-20% EtOAc/Hex) to afford (1R,3aS,5aR, 5bR,7aR,9S,11aR,11bR,13bR)-3a-((tert-butyldiphenylsilyloxy)methyl)-5a,5b,8,8,11a-pentamethyl-1-(prop-1-en-2-yl) icosahydro-1H-cyclopenta[a]chrysen-9-ol (2.75 g, 89% yield) as a white solid. $^1$H NMR (500 MHz, CHLOROFORM-d) δ ppm 0.73 (s, 3H), 0.78 (s, 3H), 0.79 (s, 3H), 0.95 (s, 3H), 0.99 (s, 3H), 1.09 (s, 9H), 0.98-1.66 (m, 19H), 1.67 (s, 3H), 1.80-1.94 (m, 2H), 2.11-2.19 (m, 2H), 2.29 (td, J=11.06, 5.65 Hz, 1H), 3.16-3.24 (m, 1H), 3.35 (d, J=10.07 Hz, 1H), 3.71 (d, J=9.77 Hz, 1H), 3.75-3.81 (m, 1H), 4.55 (s, 1H), 4.62 (d, J=2.14 Hz, 1H), 7.37-7.49 (m, 6H), 7.66-7.75 (m, 4H).

Step 2: (1R,3aS,5aR,5bR,7aR,9S,11aR,11bR,13bR)-3a-((tert-butyldiphenylsilyloxy)methyl)-5a,5b,8,8,11a-pentamethyl-1-(prop-1-en-2-yl)icosahydro-1H-cyclopenta[a]chrysen-9-ol (2.75 g, 4.04 mmol) was dissolved in dichloromethane (50 mL) and treated with PCC (1.480 g, 6.86 mmol) at rt for 18 h. The reaction mixture was diluted with 500 mL of 50% EtOAc/Hexane and stirred at rt for 10 min then filtered through a silica gel and celite pad. The solution obtained was concentrated in vacuo and the residue was dissolved in methylene chloride and purified using silica gel (0-20% EtOAc/Hexanes) to afford: (1R,3aS,5aR,5bR, 7aR,11aR,11bR,13bR)-3a-((tert-butyldiphenylsilyloxy)methyl)-5a,5b,8,8,11a-pentamethyl-1-(prop-1-en-2-yl)octadecahydro-1H-cyclopenta[a]chrysen-9(5bH)-one as a white solid (2.5 g, 91%). $^1$H NMR (400 MHz, CHLOROFORM-d) δ ppm 0.77 (S, 3H), 0.89 (s, 3H), 0.97 (s, 3H), 1.05 (s, 3H), 1.09 (s, 12H), 1.13-1.52 (m, 18H), 1.67 (s, 3H), 1.80-1.96 (m, 2H), 2.11-2.22 (m, 2H), 2.29 (td, J=11.04, 5.77 Hz, 1H), 2.35-2.59 (m, 2H), 3.33-3.42 (m, 1H), 3.71 (d, J=9.79 Hz, 1H), 4.56 (s, 1H), 4.62 (d, J=2.01 Hz, 1H), 7.35-7.52 (m, 6H), 7.65-7.78 (m, 4H).

Step 3: (1R,3aS,5aR,5bR,7aR,11aR,11bR,13bR)-3a-((tert-butyldiphenylsilyloxy)methyl)-5a,5b,8,8,11a-pentamethyl-1-(prop-1-en-2-yl)octadecahydro-1H-cyclopenta[a]chrysen-9(5bH)-one (2.5 g, 3.68 mmol) was dissolved in THF (20 mL) and cooled to −78° C. A solution of KHMDS (14.73 mL, 7.36 mmol) in toluene was added and the mixture was stirred at this temperature for 30 min, then N-Phenylbis(trifluoromethane)sulfonimide (1.447 g, 4.05 mmol) was added and the stirring was continued for 3 h. The reaction was quenched with water and extracted with ethylacetate. The organic layers were combined and dried over sodium sulfate, filtered and concentrated. The residue was purified using silica gel (0-20% EtOAc/Hexanes) to afford (1R,3aS,5aR,5bR,7aR, 11aR,11bR,13bR)-3a-((tert-butyldiphenylsilyloxy)methyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl trifluoromethanesulfonate (3.0 g, 3.70 mmol, 100% yield) as a white solid. This compound was taken to the next step without further purification. HPLC: rt=17.6 min (95% water, 5% MeOH, 10 mm Ammonium Acetate; column: Phenomenex Luna C5 4×6×150 mm 5 u; flow: 1 mL/min)

Step 4: A mixture of (1R,3aS,5aR,5bR,7aR,11aR,11bR, 13aR,13bR)-3a-((tert-butyldiphenylsilyloxy)methyl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl trifluoromethanesulfonate (3 g, 3.70 mmol), 4-methoxycarbonylphenylboronic acid (0.998 g, 5.55 mmol), Na$_2$CO$_3$ (1.176 g, 11.10 mmol) and TETRAKIS (TRIPHENYLPHOSPHINE)PALLADIUM(0) (0.128 g, 0.111 mmol) were refluxed in a mixture of Dioxane (8 mL), 2-Propanol (8.00 mL) and Water (5.00 mL) for 18 h. The reaction mixture was diluted with ethyl acetate and water and the organic layer was separated, dried over sodium sulfate, filtered and concentrated in vacuo. The residue was purified on silica gel to afford methyl 4-((1R,3aS,5aR,5bR,7aR,11aS, 11bR,13aR,13bR)-3a-((tert-butyldiphenylsilyloxy)methyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate (1.5 g, 1.882 mmol, 50.9% yield) as a white solid. $^1$H NMR (500 MHz, CHLOROFORM-d) δ ppm 0.81 (s, 3H), 0.95 (d, J=3.36 Hz, 9H), 1.00 (s, 3H), 1.09 (s, 9H), 1.12-1.66 (m, 18H), 1.69 (s, 3H), 1.81-1.95 (m, 1H), 2.08 (dd, J=17.24, 6.26 Hz, 1H), 2.14-2.23 (m, 2H), 2.31 (td, J=10.99, 5.80 Hz, 1H), 3.37 (d, J=10.07 Hz, 1H), 3.75 (d, J=9.46 Hz, 1H), 3.93 (s, 3H), 4.56 (s, 1H), 4.63 (d, J=1.83 Hz, 1H), 5.27-5.31 (m, 1H), 7.21 (d, J=8.24 Hz, 2H), 7.39-7.52 (m, 6H), 7.66-7.78 (m, 4H), 7.95 (d, J=8.24 Hz, 2H).

Step 5: A mixture of methyl 4-((1R,3aS,5aR,5bR,7aR,11aS, 11bR,13aR,13bR)-3a-((tert-butyldiphenylsilyloxy)methyl)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)benzoate (1.5 g, 1.882 mmol) and tetrabutylammonium fluoride (0.492 g, 1.882 mmol) in THF (15 mL) was heated at 50° C. for 18 h. The reaction quenched with water and diluted with EtOAc. The organic layer was separated, dried over Na$_2$SO$_4$, filtered, concentrated in vacuo and purified on silica gel using 0-50%-EtOAc/ Hex to afford methyl 4-((1R,3aS,5aR,5bR,7aR,11aS,11bR, 13aR,13bR)-3a-(hydroxymethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)benzoate (838 mg, 1.500 mmol, 80% yield) as a white solid. A portion of 20 mg was further purified using reverse phase prep HPLC for characterization. $^1$H NMR (500 MHz, CHLOROFORM-d) δ ppm 0.95 (s, 3H), 1.03 (s, 3H), 1.04 (s, 3H), 1.12 (s, 6H), 0.95-2.63 (m, 26H), 3.38 (d, J=10.99 Hz, 1H), 3.80-3.89 (m, 1H), 3.98 (s, 3H), 4.57-4.65 (m, 1H), 4.72 (d, J=2.44 Hz, 1H), 5.25-5.43 (m, 1H), 7.22 (d, J=8.24 Hz, 2H), 7.95 (d, J=8.24 Hz, 2H).

Example 14

Preparation of (1R,3aS,5aR,5bR,7aR,11aS,11bR, 13aR,13bR)-9-(4-boronophenyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysene-3a-carboxylic acid

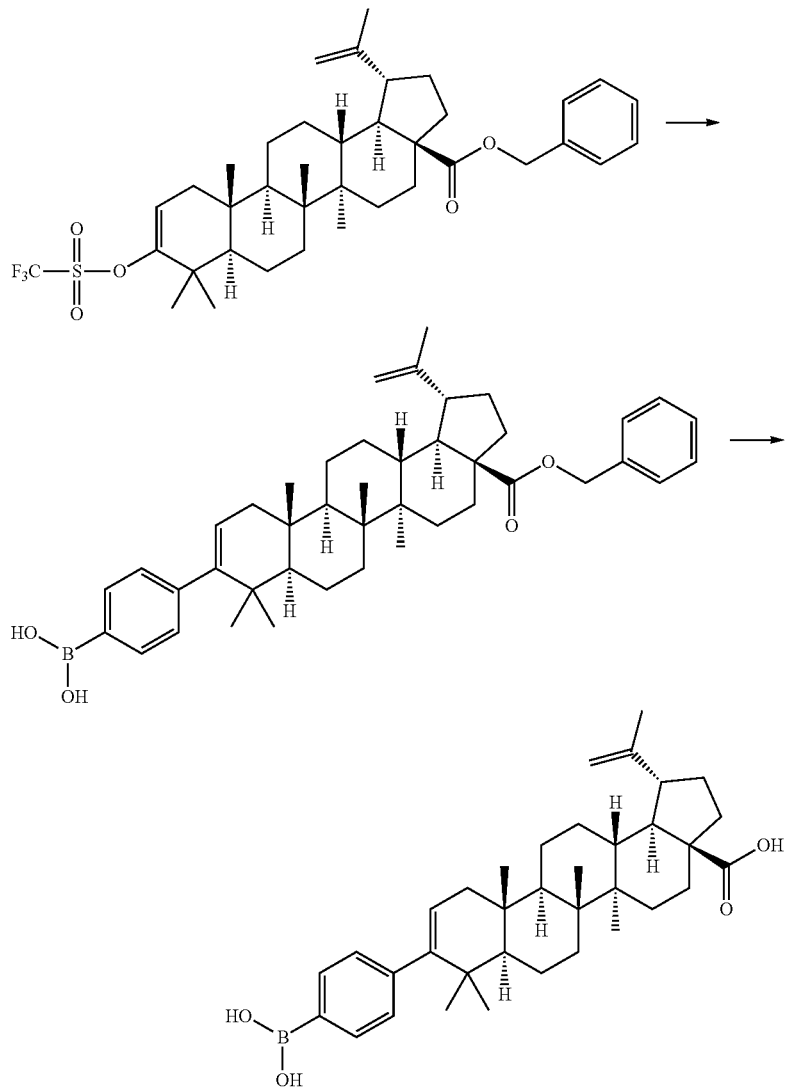

Step 1: To a solution of (1R,3aS,5aR,5bR,7aR,11aR,11bR, 13aR,13bR)-benzyl 5a,5b,8,8,11a-pentamethyl-1-(prop-1-en-2-yl)-9-(((trifluoromethyl)sulfonyl)oxy)-2,3,3a,4,5,5a, 5b,6,7,7a,8,11,11a,11b,12,13,13a,13b-octadecahydro-1H-cyclopenta[a]chrysene-3a-carboxylate (3.0 g, 4.43 mmol) in THF (100 mL) was added 1,4-benzenediboronic acid (1.469 g, 8.86 mmol) and tetrakis(triphenylphosphine)palladium(0) (0.259 g, 0.222 mmol). The resulting yellow mixture was purged with $N_2$. Then, a solution of sodium carbonate (2.82 g, 26.6 mmol) in $H_2O$ (25.00 mL) was added and the reaction mixture was heated to reflux at 90° C. After 6 h, the reaction mixture was cooled to rt, diluted with EtOAc (50 mL) and washed with $H_2O$ (50 mL). The aqueous layer was extracted with EtOAc (2×50 mL). The combined organic layer was filtered through celite pad, washed with brine, dried over $MgSO_4$, filtered and concentrated to afford a light brown solid. The crude material was absorbed onto silica gel (20 g), loaded onto a silica gel column and eluted with 3:1 hexanes: EtOAc to give (4-((1R,3aS,5aR,5bR,7aR,11aS,11bR,13aR, 13bR)-3a-((benzyloxy)carbonyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)phenyl)boronic acid (983 mg, 34.2%) as white solid. $^1$H NMR (500 MHz, CHLOROFORM-d) δ 8.18-8.14 (m, 2H), 7.43-7.38 (m, 4H), 7.38-7.35 (m, 1H), 7.31-7.29 (m, 1H), 5.37-5.34 (m, 1H), 5.17 (t, J=1.0 Hz, 2H), 4.77 (d, J=1.5 Hz, 1H), 4.64 (s, 1H), 3.08 (td, J=10.8, 4.7 Hz, 1H), 2.35-2.30 (m, 1H), 2.30-2.25 (m, 1H), 2.15 (dd, J=17.1, 6.1 Hz, 1H), 1.98-1.89 (m, 2H), 1.73 (s, 3H), 1.69 (d, J=3.7 Hz, 1H), 1.67-1.64 (m, 1H), 1.56-1.37 (m, 10H), 1.37-1.23 (m, 3H), 1.19 (d, J=13.1 Hz, 1H), 1.07 (dd, J=13.1, 4.3 Hz, 1H), 1.02 (s, 6H), 0.99 (br. s., 3H), 0.99 (br. s., 3H), 0.96-0.93 (m, 1H), 0.87 (s, 3H). $^{13}$C NMR (126 MHz, CHLOROFORM-d) δ 175.8, 150.6, 148.41-148.39 (m, 1C), 148.3, 146.8, 136.5, 134.6, 129.7, 128.5, 128.2, 128.1, 123.7, 109.6, 65.7, 56.6, 52.9, 49.6, 49.4, 46.9, 42.4, 41.8, 40.5, 38.4, 37.5, 37.0, 36.3, 33.6, 32.1, 30.6, 29.6, 29.5, 25.7, 21.3, 21.1, 19.8, 19.4, 16.5, 15.6, 14.7.

Step 2: A −78° C. solution of (4-((1R,3aS,5aR,5bR,7aR,11aS,11bR,13aR,13bR)-3a-((benzyloxy)carbonyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)phenyl)boronic acid (0.200 g, 0.308 mmol) in DCM (3 mL) was purged with N$_2$(g). Boron tribromide (1M solution in DCM) (1.079 mL, 1.079 mmol) was added dropwise. The resulting yellow reaction mixture was stirred at −78° C. for 1 h. The cold bath was removed and H$_2$O (5 mL) was added to quench the reaction. The resulting white paste was filtered and washed with H$_2$O. The crude material was dissolved in THF and DCM loaded onto a silica gel column and eluted with 1:1 hexanes:EtOAc. The fractions containing the desired product were reunited and concentrated in vacuo. The residue was further purified by reverse phase HPLC to give (1R,3aS,5aR,5bR,7aR,11aS,11bR,13aR,13bR)-9-(4-boronophenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (45.2 mg, 24.15%) as a white solid. $^1$H NMR (500 MHz, DMSO-d$_6$) δ 12.09 (br. s., 1H), 7.97 (br. s., 2H), 7.68 (d, J=7.9 Hz, 2H), 7.04 (d, J=7.9 Hz, 2H), 5.18 (d, J=4.6 Hz, 1H), 4.70 (s, 1H), 4.57 (s, 1H), 3.02-2.90 (m, 1H), 2.33-2.23 (m, 1H), 2.12 (d, J=6.4 Hz, 1H), 2.05 (dd, J=17.2, 6.3 Hz, 1H), 1.80 (d, J=7.3 Hz, 2H), 1.69-1.66 (m, 1H), 1.65 (s, 3H), 1.56 (t, J=11.3 Hz, 1H), 1.50 (br. s., 1H), 1.45-1.36 (m, 8H), 1.33-1.28 (m, 1H), 1.23 (br. s., 1H), 1.21-1.12 (m, 3H), 1.02-0.98 (m, 1H), 0.97 (s, 3H), 0.93 (s, 6H), 0.87 (s, 3H), 0.86 (s, 3H).

Preparation of Compounds of Formula III.

As previously stated, compounds of formula III can be prepared as described above for compounds of formula I and II, using ursolic acid, oleanolic acid and moronic acid as starting material instead of betulinic acid or betulin to give the corresponding E-ring modified final products. The following is a more specific version of the scheme 6 set forth above:

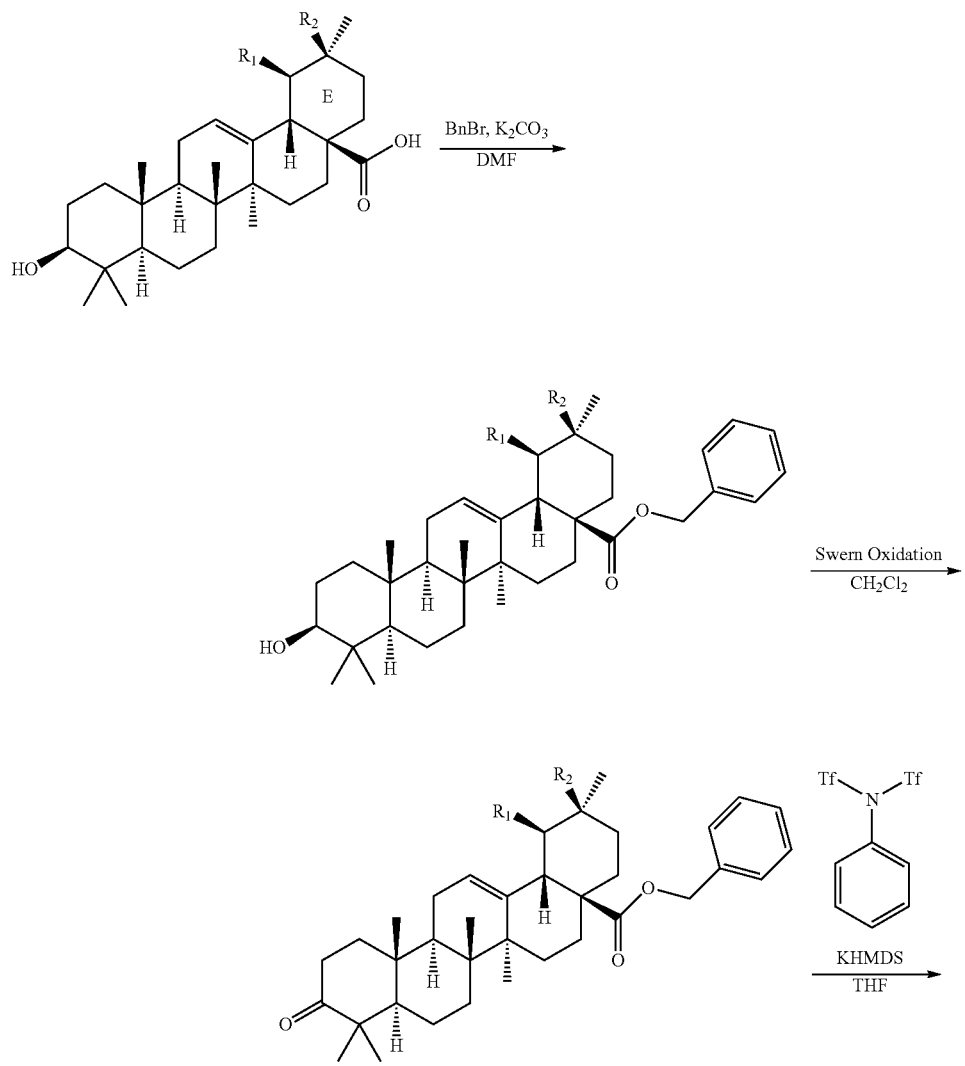

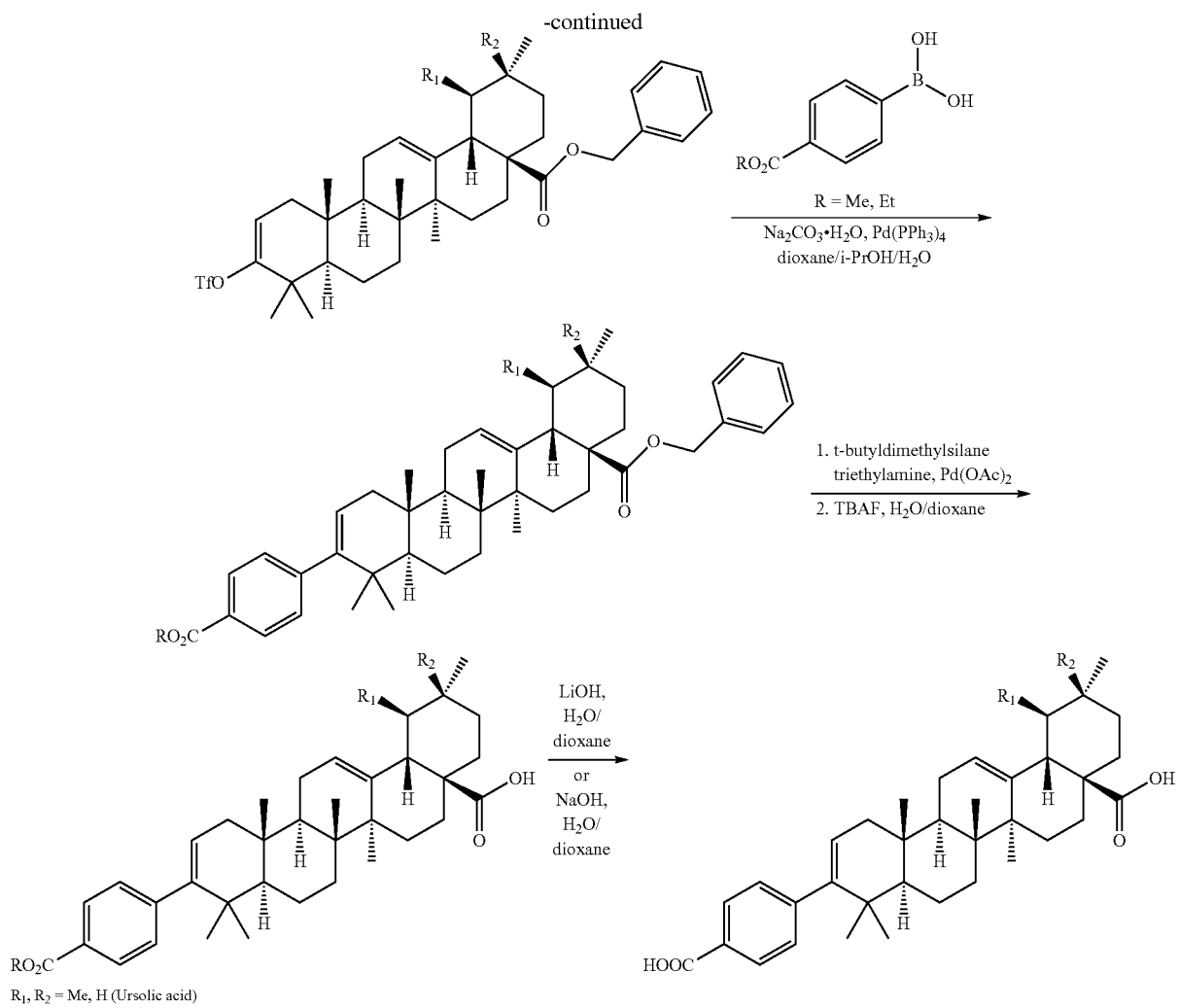

R₁, R₂ = Me, H (Ursolic acid)
R₁, R₂ = H, Me (Oleanolic acid)

Preparation of Intermediates A1, and B1

Intermediate A1: (1S,2R,4aS,6aS,6bR,8aR,10S, 12aR,12bR,14bS)-benzyl 10-hydroxy-1,2,6a,6b,9,9, 12a-heptamethyl-1,2,3,4,4a,5,6,6a,6b,7,8,8a,9,10,11, 12,12a,12b,13,14b-icosahydropicene-4-a-carboxylate

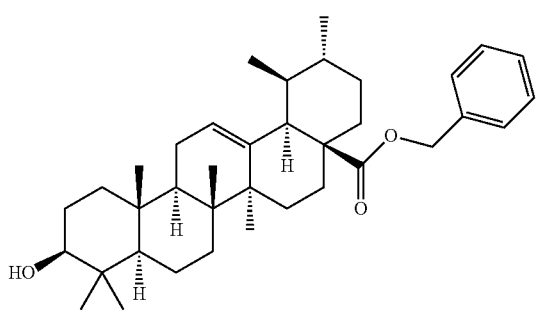

Using ursolic acid as the starting material, the title compound was prepared in accordance to the procedure described for the preparation of (1R,3aS,5aR,5bR,7aR,9S,11aR,11bR,13aR, 13bR)-benzyl 9-hydroxy-5a,5b,8,8,11a-pentamethyl-1-(prop-1-en-2-yl)icosahydro-1H-cyclopenta[a]chrysene-3a-carboxylate. (intermediate 1), (white solid, 98%) ¹H NMR (400 MHz, CHLOROFORM-d) δ ppm 0.79 (s, 3H), 0.86 (d, J=6.53 Hz, 3H), 0.90 (s, 3H), 0.93-0.96 (m, 3H), 0.99 (s, 3H), 1.08 (s, 3H), 1.23-1.42 (m, 7H), 1.42-1.53 (m, 4H), 1.59-1.92 (m, 10H), 1.96-2.08 (m, 1H), 2.23-2.31 (m, 1H), 3.22 (dt, J=11.04, 5.52 Hz, 1H), 4.96-5.14 (m, 2H), 5.25 (t, J=3.64 Hz, 1H), 7.35 (s, 5H).

Intermediate B1: (4aS,6aS,6bR,8aR,10S,12aR,12bR, 14bS)-benzyl 10-hydroxy-2,2,6a,6b,9,9,12a-heptamethyl-1,2,3,4,4a,5,6,6a,6b,7,8,8a,9,10,11,12,12a,12b, 13,14b-icosahydropicene-4-a-carboxylate

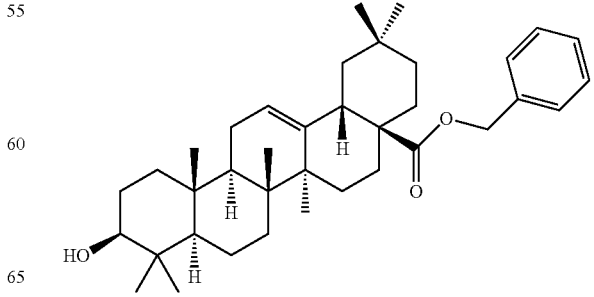

The title compound was obtained following the procedure described above for (1R,3aS,5aR,5bR,7aR,9S,11aR,11bR,13aR,13bR)-benzyl 9-hydroxy-5a,5b,8,8,11a-pentamethyl-1-(prop-1-en-2-yl)icosahydro-1H-cyclopenta[a]chrysene-3a-carboxylate. (intermediate 1), using oleanoic acid as the starting material, (white solid, 94%). $^1$H NMR (400 MHz, CHLOROFORM-d) δ ppm 0.62 (s, 3H), 0.70-0.74 (m, 1H), 0.78 (s, 3H), 0.89 (s, 3H), 0.91 (s, 3H), 0.93 (s, 3H), 0.99 (s, 3H), 1.02-1.08 (m, 1H), 1.13 (s, 3H), 1.16-1.30 (m, 4H), 1.30-1.37 (m, 2H), 1.37-1.48 (m, 2H), 1.51-1.53 (m, 1H), 1.60-1.63 (m, 2H), 1.64-1.66 (m, 1H), 1.67-1.71 (m, 1H), 1.71-1.77 (m, 1H), 1.86 (dd, J=8.78, 3.51 Hz, 2H), 1.92-2.05 (m, 1H), 2.86-2.97 (m, 1H), 3.16-3.28 (m, 1H), 5.01-5.16 (m, 2H), 5.30 (t, J=3.51 Hz, 1H), 7.35 (s, 5H).

Preparation of Intermediates A2, and B2

Swern Oxidation

Intermediate A2: (1S,2R,4aS,6aS,6bR,8aR,12aR,12bR,14bS)-benzyl 1,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate

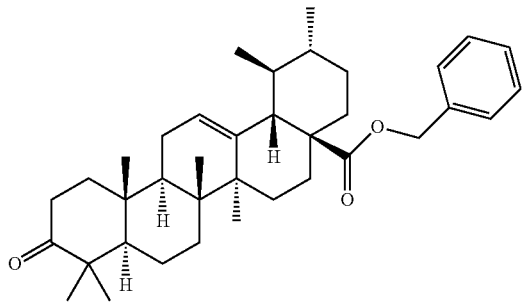

To a solution of oxalyl chloride (2.57 mL, 5.14 mmol) in methylene chloride (5 mL) at −78° C. under nitrogen was added dropwise a solution of DMSO (0.46 mL 6.4 mmol) in methylene chloride (5 mL). The mixture was allowed to warm to −50° C. To this was added a solution of the (1S,2R,4aS,6aS,6bR,8aR,10S,12aR,12bR,14bS)-benzyl 10-hydroxy-1,2,6a,6b,9,9,12a-heptamethyl-1,2,3,4,4a,5,6,6a,6b,7,8,8a,9,10,11,12,12a,12b,13,14b-icosahydropicene-4-a-carboxylate (intermediate A1) (2.34 gm, 4.28 mmol) in methylene chloride (15 mL) forming a white milky suspension. The mixture was stirred for an additional 15 minutes at −50° C. after the addition, it was then treated with triethylamine (1.79 mL, 12.84 mmol) and the reaction mixture was slowly warmed to RT. It was diluted with methylene chloride (100 mL), washed with water (2×100 mL), followed by brine (50 mL). The organic phase was separated out, dried over anhydrous sodium sulfate, and concentrated in vacuo to a syrup. This crude material was partitioned over a silica gel column, eluted with 9:1, hexanes:ethyl acetate solvent to give the title compound as a pale solid (2.22 g, 95%). $^1$H NMR (400 MHz, CHLOROFORM-d) δ ppm 0.69 (s, 3H), 0.87 (d, J=6.53 Hz, 3H), 0.93-0.97 (m, 3H), 1.03 (s, 3H), 1.05 (s, 3H), 1.09 (s, 6H), 1.26-1.40 (m, 4H), 1.40-1.54 (m, 5H), 1.59 (d, J=9.03 Hz, 2H), 1.70 (br. s., 2H), 1.93 (dd, J=9.54, 3.26 Hz, 4H), 1.97-2.08 (m, 2H), 2.29 (d, J=11.04 Hz, 1H), 2.38 (ddd, J=15.94, 6.90, 3.76 Hz, 1H), 2.49-2.61 (m, 1H), 4.97-5.03 (m, 1H), 5.10-5.15 (m, 1H), 5.27 (t, J=3.51 Hz, 1H), 7.31-7.39 (m, 5H).

Intermediate B2: (4aS,6aS,6bR,8aR,12aR,12bR,14bS)-benzyl 2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate

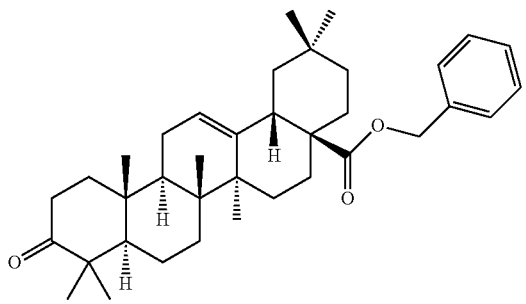

The title compound was obtained via Swern oxidation as described above using intermediate B1 as starting material, (pale solid, 94%). $^1$H NMR (400 MHz, CHLOROFORM-d) δ ppm 0.66 (s, 3H), 0.91 (s, 3H), 0.93 (s, 3H), 1.03 (s, 3H), 1.05 (s, 3H), 1.09 (s, 3H), 1.14 (s, 3H), 1.17-1.24 (m, 2H), 1.25-1.50 (m, 8H), 1.57-1.78 (m, 6H), 1.84-1.94 (m, 3H), 1.95-2.05 (m, 1H), 2.37 (ddd, J=15.81, 6.78, 3.76 Hz, 1H), 2.50-2.60 (m, 1H), 2.93 (dd, J=13.93, 3.89 Hz, 1H), 5.04-5.09 (m, 1H), 5.09-5.14 (m, 1H), 5.32 (t, J=3.64 Hz, 1H), 7.35-7.37 (m, 5H).

Preparation of Intermediates A3 and B3

Intermediate A3: (1S,2R,4aS,6aS,6bR,8aR,12aR,12bR,14bS)-benzyl 1,2,6a,6b,9,9,12a-heptamethyl-10-(trifluoromethylsulfonyloxy)-1,2,3,4,4a,5,6,6a,6b,7,8,8a,9,12,12a, 12b,13,14b-octadecahydropicene-4-a-carboxylate

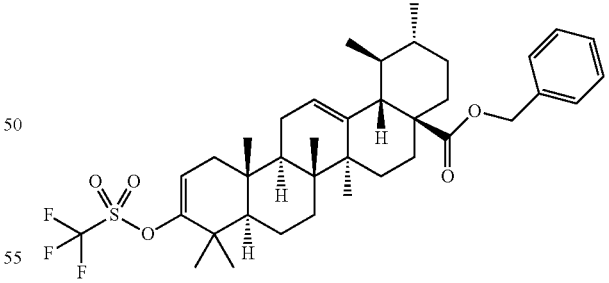

The title compound was prepared using the procedure described previously for the preparation of (1R,3aS,5aR,5bR,7aR,11aR,11bR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (intermediate 3), using ketone intermediate A2 as starting material (45%). $^1$H NMR (400 MHz, CHLOROFORM-d) δ ppm 0.67 (s, 3H), 0.87 (d, J=6.53 Hz, 3H), 0.93-0.97 (m, 3H), 0.99 (s, 3H), 1.04 (s, 3H), 1.08 (s, 3H), 1.14 (s, 3H), 1.17-1.21

(m, 1H), 1.21-1.47 (m, 5H), 1.50 (dd, J=13.05, 3.26 Hz, 2H), 1.56 (s, 3H), 1.58-1.78 (m, 3H), 1.78-1.97 (m, 3H), 1.97-2.07 (m, 2H), 2.15 (dd, J=17.07, 6.78 Hz, 1H), 2.30 (d, J=11.54 Hz, 1H), 4.97-5.02 (m, 1H), 5.10-5.15 (m, 1H), 5.27 (t, J=3.51 Hz, 1H), 5.59 (dd, J=6.78, 2.01 Hz, 1H), 7.35 (s, 5H); $^{19}$F NMR (376.46 MHz, CHLOROFORM-d) δ ppm −74.83.

Intermediate B3: (4aS,6aS,6bR,8aR,12aR,12bR,14bS)-benzyl 2,2,6a,6b,9,9,12a-heptamethyl-10-(trifluoromethylsulfonyloxy)-1,2,3,4,4a,5,6,6a,6b,7,8,8a,9,12,12a,12b,13,14b-octadecahydropicene-4-a-carboxylate

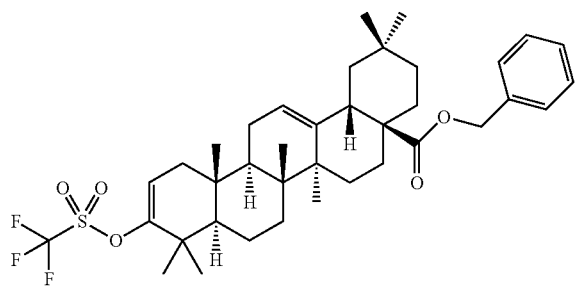

The title compound was prepared using the procedure described previously for the preparation of (1R,3aS,5aR,5bR,7aR,11aR,11bR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a,11b,12,13,13a,13b-octadecahydro-1H-cyclopenta[a]chrysene-3a-carboxylate (intermediate 3), using ketone intermediate B2 as starting material (29%). $^1$H NMR (400 MHz, CHLOROFORM-d) δ ppm 0.65 (s, 3H), 0.91 (s, 3H), 0.94 (s, 3H), 0.97 (s, 3H), 1.04 (s, 3H), 1.05-1.12 (m, 1H), 1.14 (s, 6H), 1.16-1.28 (m, 3H), 1.28-1.42 (m, 2H), 1.42-1.54 (m, 2H), 1.57-1.65 (m, 2H), 1.68 (d, J=14.56 Hz, 2H), 1.73 (d, J=4.52 Hz, 1H), 1.78-1.84 (m, 2H), 1.86 (dd, J=5.90, 4.14 Hz, 1H), 1.90-1.97 (m, 1H), 1.98-2.04 (m, 1H), 2.12 (dd, J=17.07, 6.78 Hz, 1H), 2.93 (dd, J=13.93, 4.14 Hz, 1H), 5.03-5.14 (m, 3H), 5.33 (t, J=3.51 Hz, 1H), 5.58 (dd, J=6.78, 2.01 Hz, 1H), 7.34-7.38 (m, 5H); $^{19}$F NMR (376.46 MHz, CHLOROFORM-d) δ ppm −74.84.

Intermediate A4: Preparation of Intermediates A4 and B4

(1S,2R,4aS,6aS,6bR,8aR,12aS,12bR,14bS)-benzyl 10-(4-(methoxycarbonyl)phenyl)-1,2,6a,6b,9,9,12a-heptamethyl-1,2,3,4,4a,5,6,6a,6b,7,8,8a,9,12,12a,12b,13,14b-octadecahydropicene-4-a-carboxylate

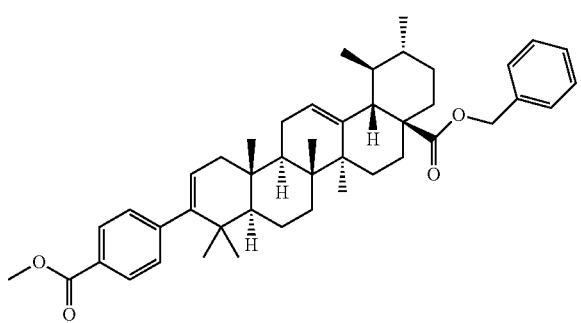

The title compound was prepared via from triflate intermediate A3 using the Suzuki coupling procedure described previously for the preparation of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (intermediate 4), (68%). $^1$H NMR (400 MHz, CHLOROFORM-d) δ ppm 0.73 (s, 3H), 0.88 (d, J=6.53 Hz, 3H), 0.93-0.97 (m, 9H), 1.06 (s, 3H), 1.12 (s, 3H), 1.14-1.19 (m, 1H), 1.25 (d, J=12.30 Hz, 2H), 1.31-1.45 (m, 4H), 1.45-1.54 (m, 2H), 1.57-1.62 (m, 1H), 1.65 (dd, J=13.05, 4.02 Hz, 1H), 1.68-1.79 (m, 3H), 1.80-1.87 (m, 1H), 1.91-1.98 (m, 2H), 2.02 (dd, J=12.92, 4.64 Hz, 1H), 2.10 (dd, J=17.07, 6.27 Hz, 1H), 2.31 (d, J=11.04 Hz, 1H), 3.92 (s, 3H), 4.98-5.03 (m, 1H), 5.11-5.15 (m, 1H), 5.29-5.34 (m, 2H), 7.21 (d, J=8.53 Hz, 2H), 7.31-7.39 (m, 5H), 7.94 (d, J=8.28 Hz, 2H).

Intermediate B4: (4aS,6aS,6bR,8aR,12aS,12bR,14bS)-benzyl 1044-(methoxycarbonyl)phenyl)-2,2,6a,6b,9,9,12a-heptamethyl-1,2,3,4,4a,5,6,6a,6b,7,8,8a,9,12,12a,12b,13,14b-octadecahydropicene-4-a-carboxylate

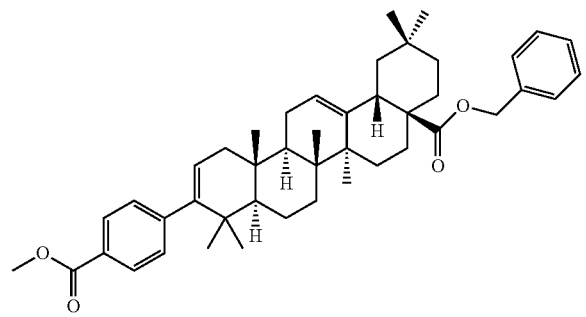

The title compound was prepared via from triflate intermediate B3 using the Suzuki coupling procedure described previously for the preparation of (1R,3aS,5aR,5bR,7aR,11aS,11bR,13aR,13bR)-benzyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (intermediate 4), (65%). $^1$H NMR (400 MHz, CHLOROFORM-d) δ ppm 0.70 (s, 3H), 0.92 (s, 3H), 0.95 (s, 9H), 1.04 (s, 3H), 1.08-1.15 (m, 1H), 1.17 (s, 3H), 1.19-1.25 (m, 2H), 1.27 (br. s., 2H), 1.30-1.38 (m, 2H), 1.40 (dd, J=8.03, 3.51 Hz, 1H), 1.43-1.54 (m, 2H), 1.58-1.68 (m, 3H), 1.68-1.78 (m, 3H), 1.90 (dd, J=6.15, 3.89 Hz, 1H), 1.92-2.03 (m, 2H), 2.07 (dd, J=17.07, 6.27 Hz, 1H), 2.95 (dd, J=13.80, 4.02 Hz, 1H), 3.92 (s, 3H), 5.04-5.15 (m, 2H), 5.31 (dd, J=6.15, 1.88 Hz, 1H), 5.36 (t, J=3.39 Hz, 1H), 7.21 (d, J=8.53 Hz, 2H), 7.33-7.38 (m, 5H), 7.94 (d, J=8.28 Hz, 2H).

Preparation of Intermediates A5 and B5

Intermediate A5: (1S,2R,4aS,6aS,6bR,8aR,12aS, 12bR,14bS)-tert-butyldimethylsilyl 10-(4-(methoxycarbonyl)phenyl)-1,2,6a,6b,9,9,12a-heptamethyl-1,2, 3,4,4a,5,6,6a,6b,7,8,8a,9,12,12a,12b,13,14b-octadecahydropicene-4-a-carboxylate

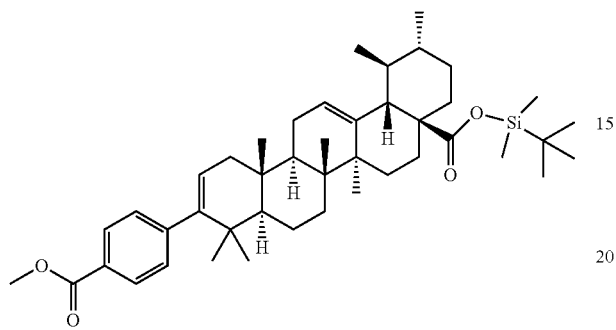

Palladium catalyzed hydrosilylation of the benzyl esters intermediate A4 as described in the preparation of 1R,3aS, 5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysene-3a-carboxylate, (intermediate 5) afforded the title compound (57%). $^1$H NMR (400 MHz, CHLOROFORM-d) δ ppm 0.24 (s, 3H), 0.25 (s, 3H), 0.87-0.90 (m, 6H), 0.93-0.98 (m, 18H), 1.09 (s, 3H), 1.12 (s, 3H), 1.16-1.51 (m, 6H), 1.52-1.59 (m, 7H), 1.59-1.88 (m, 4H), 1.88-2.07 (m, 3H), 2.11 (dd, J=17.07, 6.27 Hz, 1H), 2.22 (d, J=10.29 Hz, 1H), 3.92 (s, 3H), 5.30-5.34 (m, 2H), 7.22 (d, J=8.28 Hz, 2H), 7.94 (d, J=8.28 Hz, 2H);

Intermediate B5: (4aS,6aS,6bR,8aR,12aS,12bR, 14bS)-tert-butyldimethylsilyl 10-(4-(methoxycarbonyl)phenyl)-2,2,6a,6b,9,9,12a-heptamethyl-1,2,3,4, 4a,5,6,6a,6b,7,8,8a,9,12,12a,12b,13,14b-octadecahydropicene-4-a-carboxylate

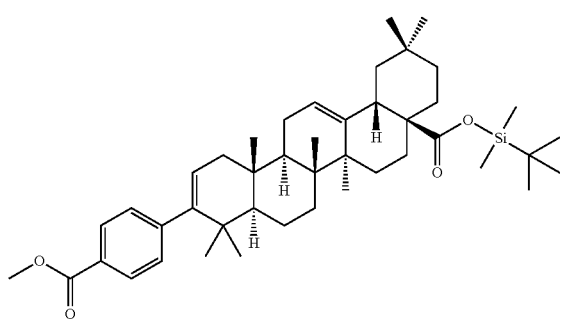

Palladium catalyzed hydrosilylation of the benzyl esters intermediate B4 as described in the preparation of 1R,3aS, 5aR,5bR,7aR,11aS,11bR,13aR,13bR)-tert-butyldimethylsilyl 9-(4-(methoxycarbonyl)phenyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysene-3a-carboxylate, (intermediate 5) afforded the title compound (54%). $^1$H NMR (400 MHz, CHLOROFORM-d) δ ppm 0.25 (s, 3H), 0.26 (s, 3H), 0.87 (s, 3H), 0.92 (s, 3H), 0.93-0.97 (m, 18H), 1.07 (s, 3H), 1.12-1.17 (m, 2H), 1.18 (s, 4H), 1.21-1.30 (m, 3H), 1.30-1.53 (m, 5H), 1.62-1.80 (m, 5H), 1.82-1.95 (m, 1H), 1.95-2.03 (m, 2H), 2.07 (dd, J=17.07, 6.27 Hz, 1H), 2.88 (dd, J=13.93, 4.64 Hz, 1H), 3.92 (s, 3H), 5.31 (dd, J=6.27, 1.76 Hz, 1H), 5.35 (t, J=3.51 Hz, 1H), 7.22 (d, J=8.53 Hz, 2H), 7.94 (d, J=8.28 Hz, 2H).

Preparation of Intermediates A6 and B6

Intermediate A6: (1S,2R,4aS,6aS,6bR,8aR,12aS, 12bR,14bS)-10-(4-(methoxycarbonyl)phenyl)-1,2, 6a,6b,9,9,12a-heptamethyl-1,2,3,4,4a,5,6,6a,6b,7,8, 8a,9,12,12a,12b,13,14b-octadecahydropicene-4-a-carboxylic acid

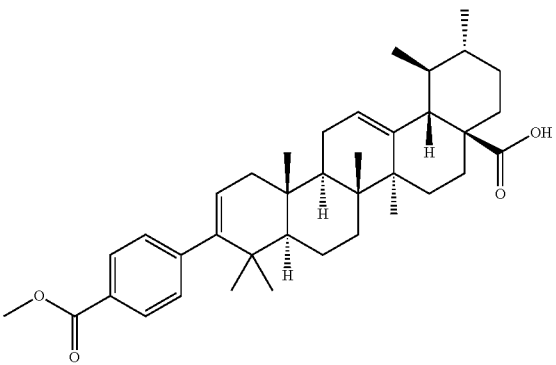

The title compound was prepared following the procedure describe for the preparation of (1R,3aS,5aR,5bR,7aR,11aS, 11bR,13aR,13bR)-9-(4-(methoxycarbonyl)phenyl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (example 7) using intermediate A5 as starting material, (98%). $^1$H NMR (400 MHz, CHLOROFORM-d) δ ppm 0.87 (s, 3H), 0.89 (d, J=6.53 Hz, 3H), 0.93 (s, 3H), 0.94 (s, 3H), 0.96 (s, 3H), 0.98 (s, 3H), 1.03 (t, J=7.28 Hz, 2H), 1.08-1.11 (m, 3H), 1.13 (s, 3H), 1.19 (s, 2H), 1.22-1.82 (m, 10H), 1.84-2.06 (m, 2H), 2.06-2.15 (m, 1H), 2.23 (d, J=11.04 Hz, 1H), 3.32-3.51 (m, 1H), 3.92 (s, 3H), 5.32 (dd, J=5.90, 1.63 Hz, 2H), 7.20 (d, J=8.28 Hz, 2H), 7.94 (d, J=8.28 Hz, 2H).

Intermediate B6: (4aS,6aS,6bR,8aR,12aS,12bR, 14bS)-10-(4-(methoxycarbonyl)phenyl)-2,2,6a,6b,9, 9,12a-heptamethyl-1,2,3,4,4a,5,6,6a,6b,7,8,8a,9,12, 12a,12b,13,14b-octadecahydropicene-4-a-carboxylic acid

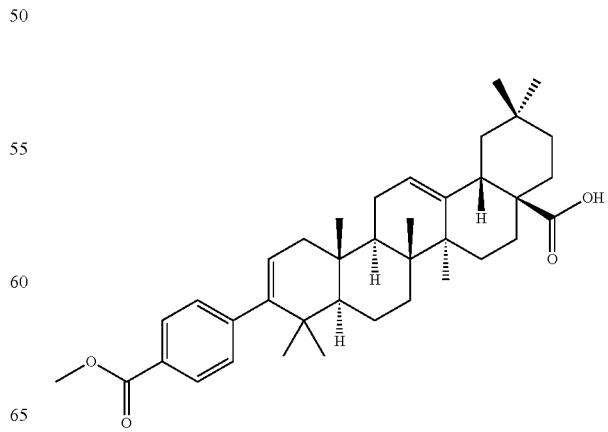

The title compound was prepared following the procedure describe for the preparation of (1R,3aS,5aR,5bR,7aR,11aS,11bR,13aR,13bR)-9-(4-(methoxycarbonyl)phenyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylic acid (example 7) using intermediate B5 as starting material, (95%). $^1$H NMR (400 MHz, CHLOROFORM-d) δ ppm 0.85 (s, 3H), 0.91-0.97 (m, 12H), 1.03 (t, J=7.28 Hz, 2H), 1.08 (s, 3H), 1.12-1.16 (m, 1H), 1.18 (s, 3H), 1.21 (d, J=4.52 Hz, 2H), 1.26 (br. s., 2H), 1.28 (br. s., 1H), 1.32-1.43 (m, 2H), 1.43-1.53 (m, 2H), 1.53-1.61 (m, 2H), 1.63 (d, J=4.27 Hz, 1H), 1.71 (d, J=6.02 Hz, 1H), 1.74-1.82 (m, 2H), 1.82-1.96 (m, 2H), 2.01 (dd, J=7.91, 3.64 Hz, 1H), 2.03-2.13 (m, 1H), 2.87 (dd, J=13.68, 3.89 Hz, 1H), 3.33-3.46 (m, 1H), 3.92 (s, 3H), 5.31 (dd, J=6.15, 1.63 Hz, 1H), 5.36 (t, J=3.39 Hz, 1H), 7.20 (d, J=8.28 Hz, 2H), 7.94 (d, J=8.53 Hz, 2H).

Preparation of Examples 12 and 13

Example 12

(1S,2R,4aS,6aS,6bR,8aR,12aS,12bR,14bS)-10-(4-carboxyphenyl)-1,2,6a,6b,9,9,12a-heptamethyl-1,2,3,4,4a,5,6,6a,6b,7,8,8a,9,12,12a,12b,13,14b-octadecahydropicene-4-a-carboxylic acid

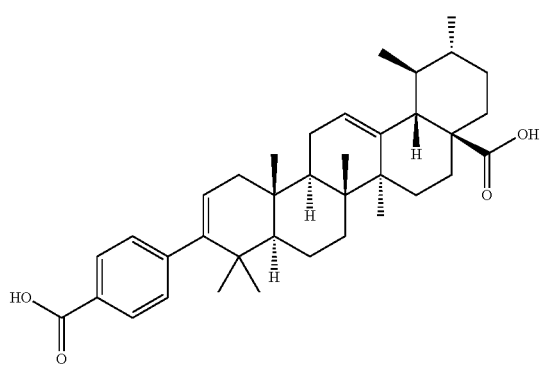

Saponification of the intermediates A6 was conducted as followed: to a solution of (1S,2R,4aS,6aS,6bR,8aR,12aS,12bR,14bS)-10-(4-(methoxycarbonyl)phenyl)-1,2,6a,6b,9,9,12a-heptamethyl-1,2,3,4,4a,5,6,6a,6b,7,8,8a,9,12,12a,12b,13,14b-octadecahydropicene-4-a-carboxylic acid (intermediate A6) (20 mg, 0.035 mmol) in a mixture of dioxane (1 mL) and methanol (0.5 mL) was added a 1N solution of NaOH (0.5 mL, 0.5 mmol). The mixture was warmed to 65° C. for 2 h. The crude product was further purified by preparative HPLC(YMC Combiprep ODS 30×50 mm S5 column) eluted with gradient mixture of MeOH/water/TFA. The desired fractions were combined, evaporated to afford the title compound (12 mg, 61%).

Example 13

(4aS,6aS,6bR,8aR,12aS,12bR,14bS)-10-(4-carboxyphenyl)-2,2,6a,6b,9,9,12a-heptamethyl-1,2,3,4,4a,5,6,6a,6b,7,8,8a,9,12,12a,12b,13,14b-octadecahydropicene-4-a-carboxylic acid The title compound was prepared following the saponification method described above using (4aS,6aS,6bR,8aR,12aS,12bR,14bS)-10-(4-(methoxycarbonyl)phenyl)-2,2,6a,6b,9,9,12a-heptamethyl-1,2,3,4,4a,5,6,6a,6b,7,8,8a,9,12,12a,12b,13,14b-octadecahydropicene-4-a-carboxylic acid (intermediate B6) as starting material (76%). $^1$H NMR (400 MHz, Methanol-d$_4$) δ ppm 0.91 (d, 3H), 0.93 (s, 3H), 0.95-1.00 (m, 10H), 1.14 (s, 3H), 1.17 (s, 3H), 1.27-1.57 (m, 7H), 1.57-1.73 (m, 6H), 1.79 (d, J=16.31 Hz, 2H), 1.88-2.11 (m, 5H), 2.15 (dd, J=17.07, 6.27 Hz, 1H), 2.24 (d, J=11.29 Hz, 1H), 5.30 (t, J=3.39 Hz, 1H), 5.33 (dd, J=6.27, 1.76 Hz, 1H), 7.24 (d, J=8.53 Hz, 2H), 7.93 (d, J=8.53 Hz, 2H). For intermediate 21-$^1$H NMR (400 MHz, Methanol-d$_4$) δ ppm 0.91 (s, 3H), 0.93 (s, 3H), 0.96 (s, 3H), 0.98 (d, J=2.01 Hz, 6H), 1.12 (s, 3H), 1.16 (d, J=13.80 Hz, 2H), 1.21 (s, 3H), 1.31 (d, J=10.79 Hz, 2H), 1.35-1.49 (m, 3H), 1.49-1.67 (m, 5H), 1.67-1.82 (m, 5H), 1.82-1.98 (m, 2H), 1.98-2.06 (m, 2H), 2.07-2.18 (m, 1H), 2.89 (dd, J=13.68, 3.64 Hz, 1H), 5.25-5.38 (m, 2H), 7.24 (d, J=8.03 Hz, 2H), 7.93 (d, J=8.28 Hz, 2H).

Biology Data for the Examples

"μM" means micromolar;

"mL" means milliliter;

"μl" means microliter;

"mg" means milligram;

"μg" means microgram;

The materials and experimental procedures used to obtain the results reported in Tables 1-2 are described below.

HIV cell culture assay—MT-2 cells and 293T cells were obtained from the NIH AIDS Research and Reference Reagent Program. MT-2 cells were propagated in RPMI 1640 media supplemented with 10% heat inactivated fetal bovine serum, 100 μg/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of NL$_{4-3}$ was obtained from the NIH AIDS Research and Reference Reagent Program. A recombinant NL$_{4-3}$ virus, in which a section of the nef gene from NL4-3 was replaced with the Renilla luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) µL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$s data for the compounds is shown in Table 2. Table 1 is the key for the data in Table 2.

Results

TABLE 1

Biological Data Key for $EC_{50}$s

| Compounds with $EC_{50} > 1$ µM | Compounds with $EC_{50} < 1$ µM |
|---|---|
| Group "B" | Group "A" |

TABLE 2

| Example | | $EC50$ |
|---|---|---|
| 1a | 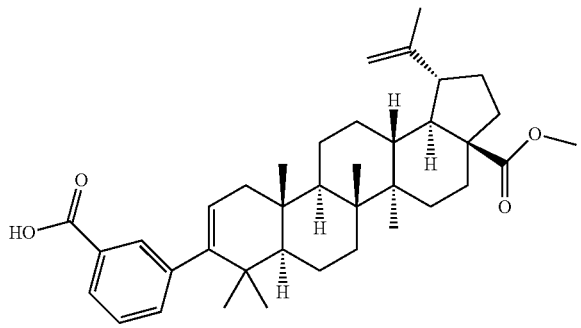 | B |
| 1b | 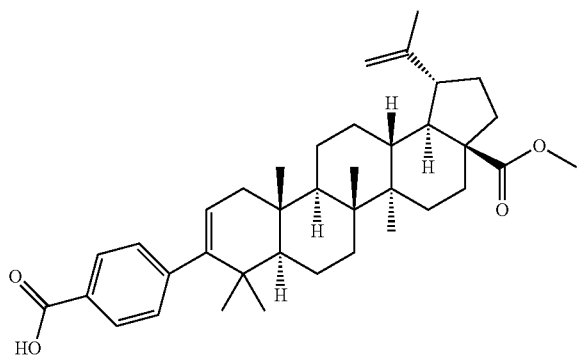 | A |
| 2a | 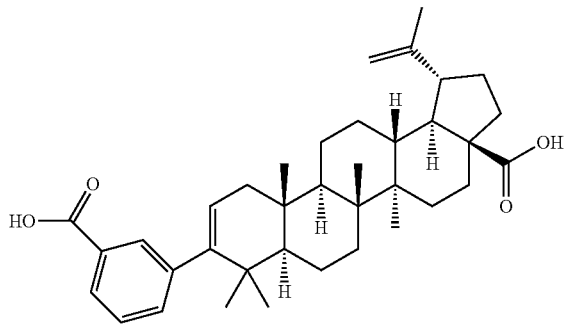 | B |

TABLE 2-continued

| Example | | EC50 |
|---|---|---|
| 2b | (structure) | A |
| 3a | (structure) | 2.0 μM |
| 3b | (structure) | A |
| 4a | (structure) | A |

TABLE 2-continued

| Example | | EC50 |
|---|---|---|
| 4b | [structure] | B |
| 4c | [structure] | A |
| 4d | [structure] | A |
| 4e | [structure] | A |

TABLE 2-continued
| Example | | EC50 |
|---|---|---|
| 4f | 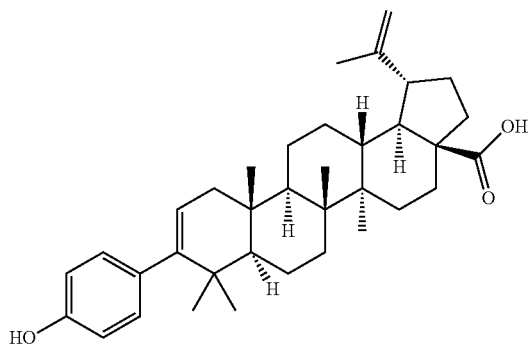 | A |
| 4g | 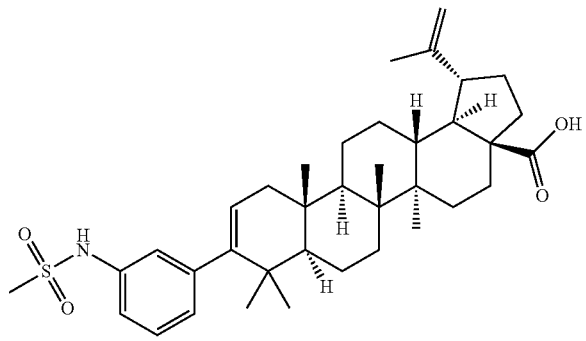 | B |
| 4h | 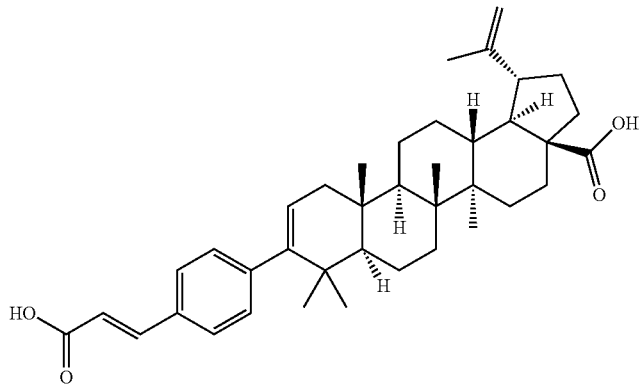 | A |
| 4i | 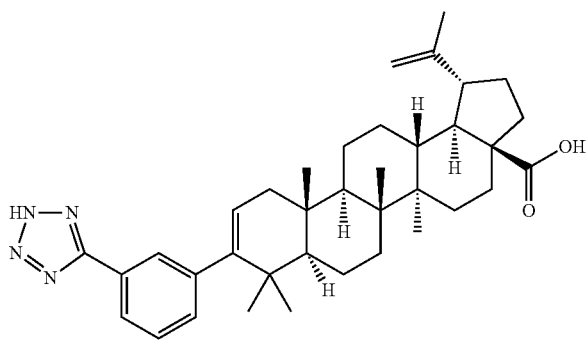 | B |

TABLE 2-continued
| Example | | EC50 |
|---|---|---|
| 4j | 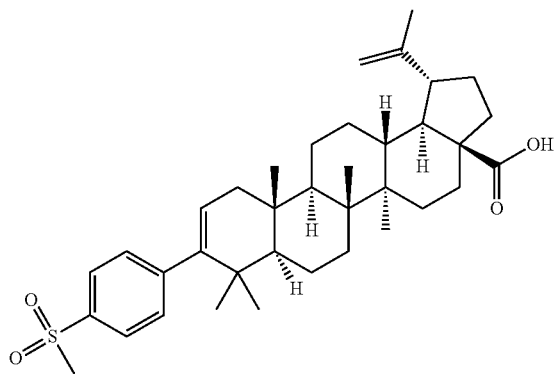 | B |
| 4k | 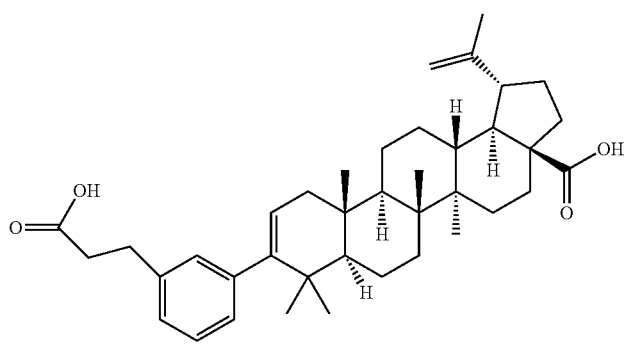 | A |
| 4l | 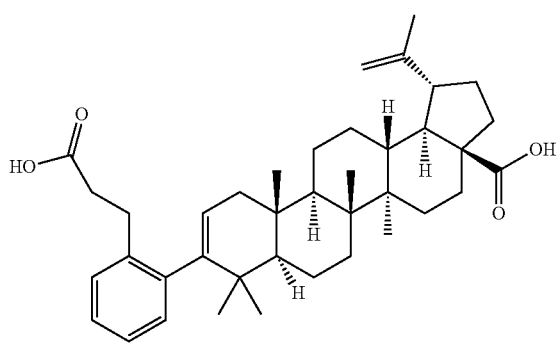 | B |
| 4m | 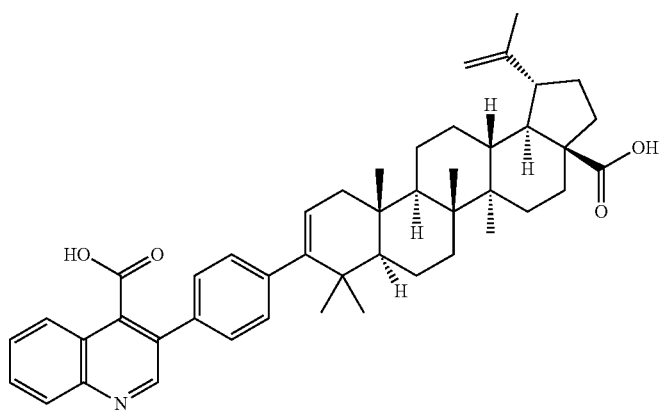 | B |

TABLE 2-continued

| Example | | EC50 |
|---|---|---|
| 4n | | A |
| 4o | | A |
| 5a | | A |
| 5b | | A |

TABLE 2-continued

| Example | EC50 |
|---|---|
| 5c | 0.23 μM |
| 5d | A |
| 5e | B |
| 5f | A |

TABLE 2-continued

| Example | | EC50 |
|---|---|---|
| 5g | (structure: triterpenoid with 3-chloro-4-hydroxyphenyl substituent) | B |
| 5h | (structure: triterpenoid with 3-methyl-4-hydroxyphenyl substituent) | B |
| 5i | (structure: triterpenoid with 4-(methylsulfonylamino)phenyl substituent) | B |
| 5j | (structure: triterpenoid with 4-sulfamoylphenyl substituent) | A |

TABLE 2-continued

| Example | EC50 |
|---|---|
| 5k | A |
| 5l | B |
| 5m | A |
| 5n | A |

TABLE 2-continued
| Example | | EC50 |
|---|---|---|
| 5o | 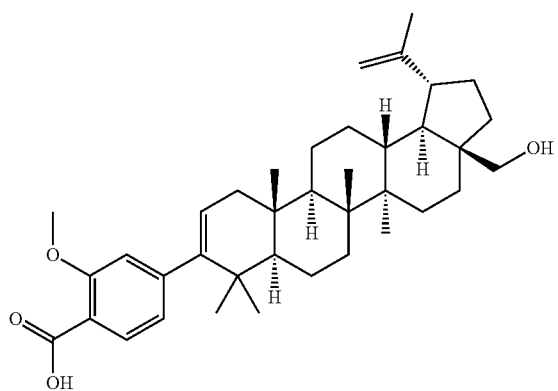 | 0.5 μM |
| 5p | 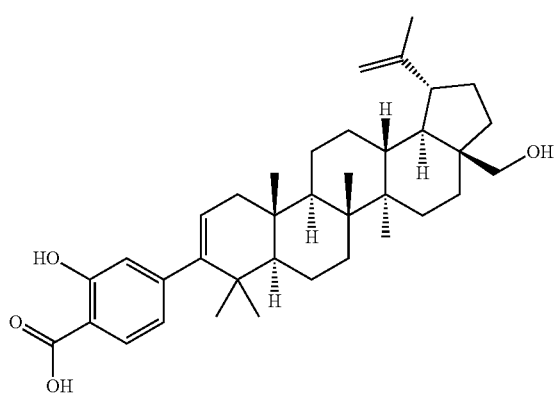 | A |
| 5q | 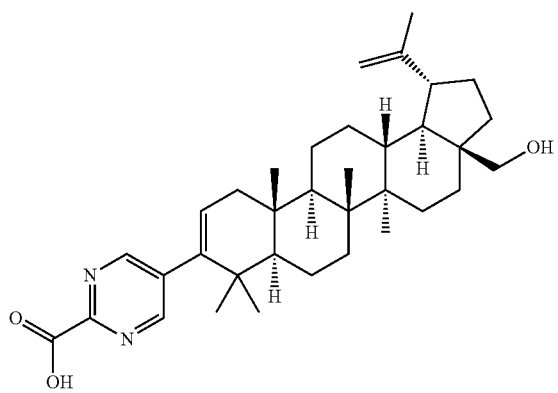 | B |
| 5r | 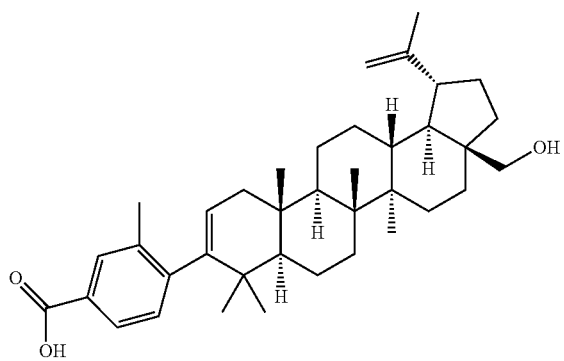 | A |

TABLE 2-continued

| Example | EC50 |
|---|---|
| 5s | A |
| 5t | A |
| 5u | A |
| 6a | A |

TABLE 2-continued
| Example | | EC50 |
|---|---|---|
| 6b | 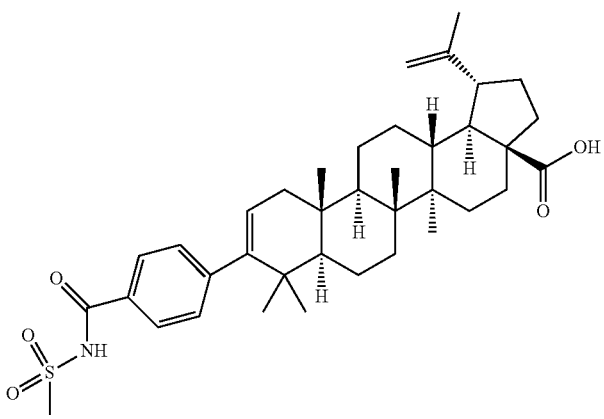 | A |
| 7 | 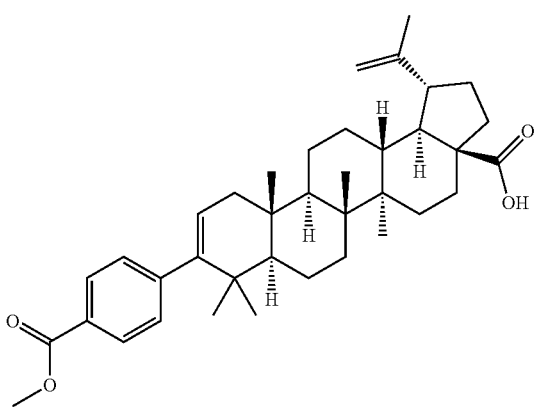 | B |
| 8 | 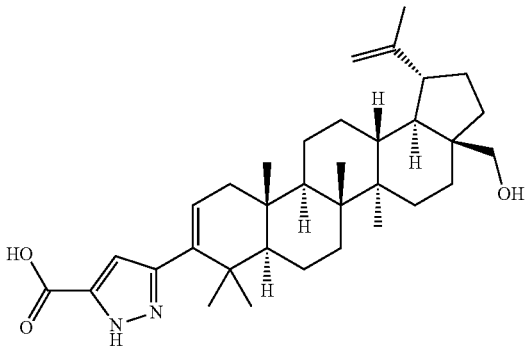 | A |
| 9 | 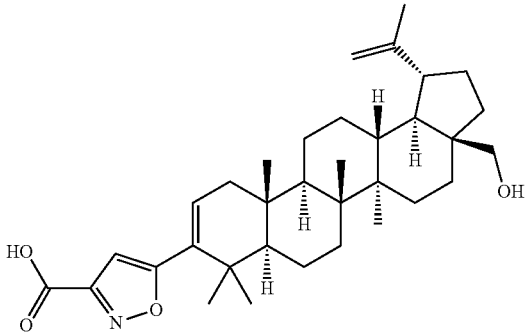 | A |

TABLE 2-continued

| Example | | EC50 |
|---|---|---|
| 10 | | A |
| 11 | | B |
| 12 | | A |
| 13 | | A |

TABLE 2-continued

| Example | EC50 |
|---|---|
| 14 | 13.4 nM |

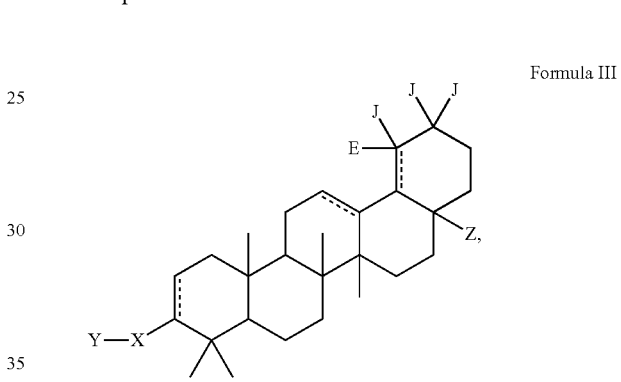

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group of:

a compound of formula I

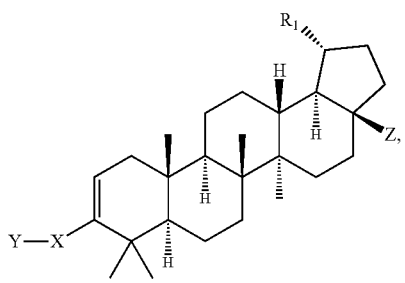

Formula I a compound of formula II

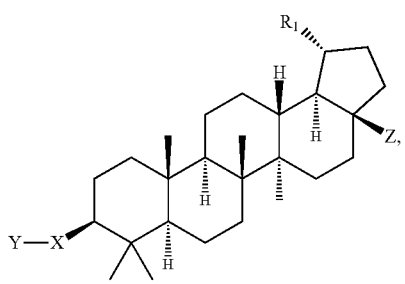

Formula II a compound of formula III

Formula III wherein $R_1$ is isopropenyl or isopropyl;
J and E are —H or —$CH_3$;
E is absent when the double bond is present;
X is a phenyl or heteroaryl ring substituted with A, wherein A is at least one member selected from the group of —H, -halo, -hydroxyl, —$C_{1-6}$ alkyl, —$C_{1-6}$ alkoxy, —$C_{1-6}$ haloalkyl, —$NR_2R_2$, —$COOR_2$, —$C(O)NR_2R_2$, —$C(O)NR_2SO_2R_3$, —$SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, and -bicyclic heteroaryl-$COOR_2$, wherein $R_2$ is H, —$C_{1-6}$ alkyl, or substituted —$C_{1-6}$ alkyl and wherein $R_3$ is $C_{1-6}$ alkyl and further wherein n=1-6;
Y is selected from the group of —$COOR_2$, —$C(O)NR_2R_2$, —$C(O)NR_2SO_2R_3$, —$C(O)NR_2SO_2NR_2R_2$, —$NR_2SO_2R_2$, —$SO_2NR_2R_2$, —$C_{1-6}$ cycloalkyl-$COOR_2$, —$C_{1-6}$ alkenyl-$COOR_2$, —$C_{1-6}$ alkynyl-$COOR_2$, —$C_{1-6}$ alkyl-$COOR_2$, —$NHC(O)(CH_2)_n$—$COOR_2$, —$SO_2NR_2C(O)R_2$, -tetrazole, —$CONHOH$, -bicyclic heteroaryl-$COOR_2$, and —$B(OH)_2$, wherein n=1-6; and
Z is selected from the group of —COOH, —$COOR_4$ and —$CH_2OH$, wherein $R_4$ is $C_{1-6}$ alkyl or $C_{1-6}$ alkylphenyl; and pharmaceutically acceptable salts thereof.

2. The compound as claimed in claim 1, wherein said compound is a compound of Formula I.

3. The compound as claimed in claim 1, wherein said compound is a compound of Formula II.

4. The compound as claimed in claim 2, wherein X is a phenyl ring.

5. The compound as claimed in claim 2, wherein X is a 5 or 6-membered heteroaryl ring.

6. The compound as claimed in 4, wherein A is at least one member selected from the group of —H, —OH, -halo, —$C_{1-3}$ alkyl, and —$C_{1-3}$ alkoxy, wherein -halo is selected from the group of —Cl, —F and —Br.

7. The compound as claimed in claim 6, wherein Y is —COOH.

8. The compound as claimed in claim 4, wherein X is a phenyl ring and Y is —COOH in the para position according to Formula Ia:

Formula Ia

9. The compound as claimed in claim 8, wherein A is at least one member selected from the group of —H, -halo, —OH, —$C_{1-3}$alkyl and —$C_{1-3}$ alkoxy.

10. The compound as claim in claim 9, wherein A is at least one member selected from the group of —H, -fluoro, -chloro, —OH, -methyl and -methoxy.

11. A compound which is selected from the group consisting of:

-continued

137
-continued
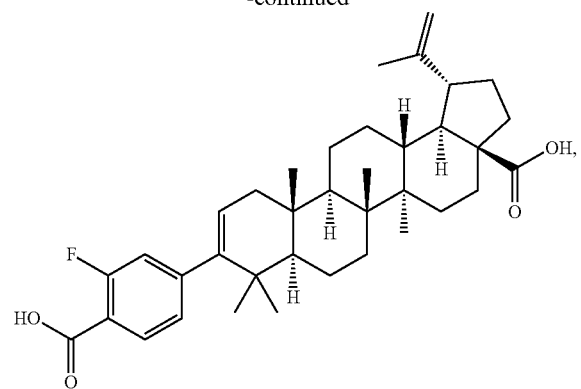
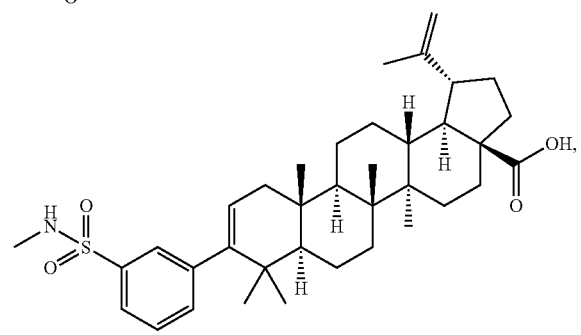
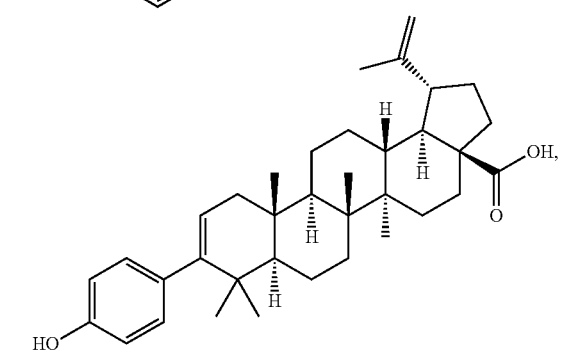
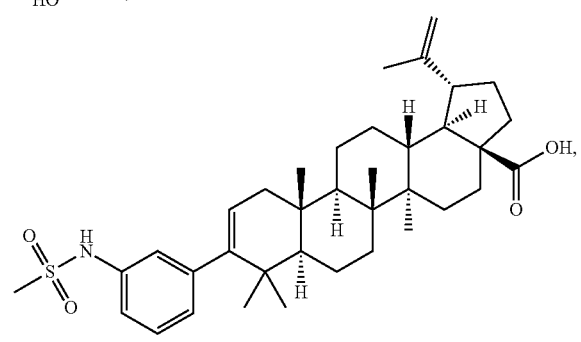
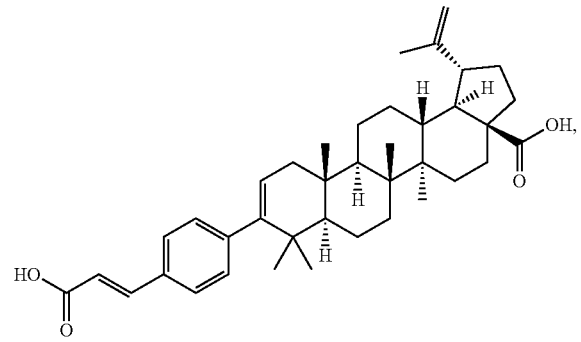
138
-continued
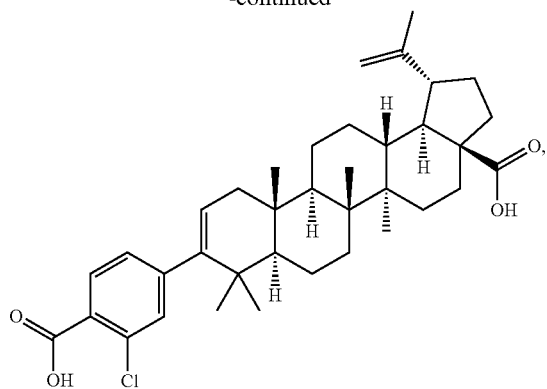
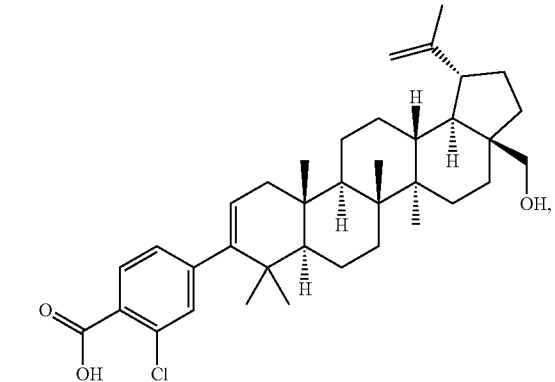
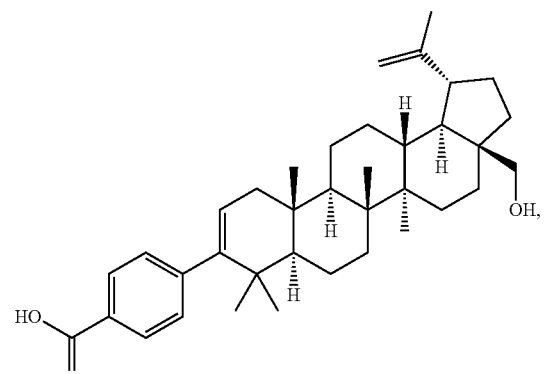
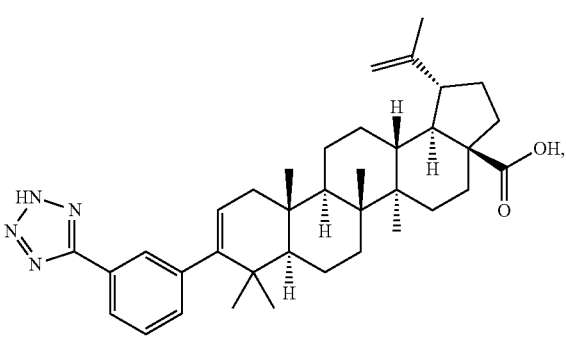

139
-continued
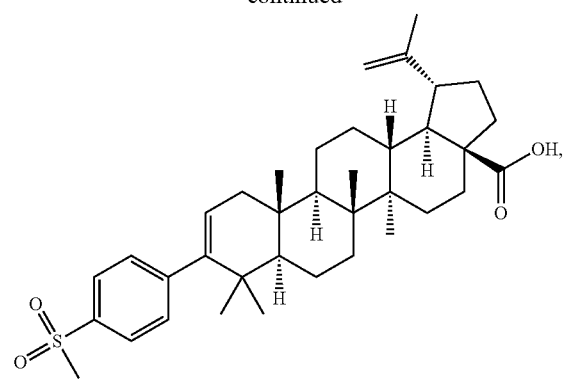
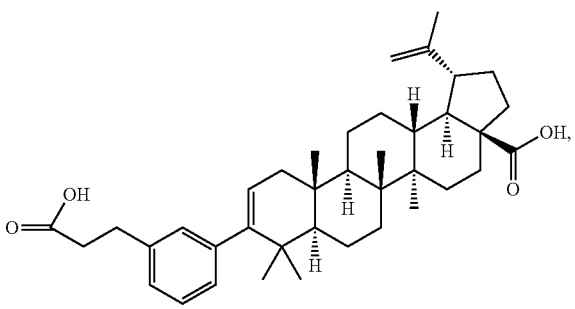
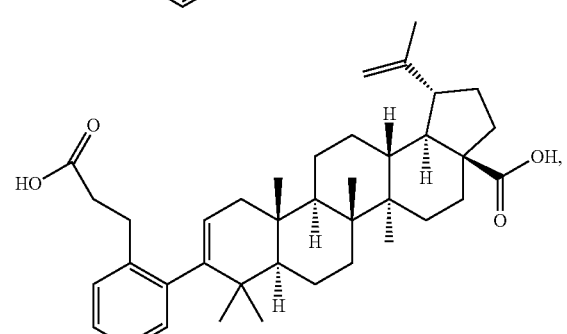
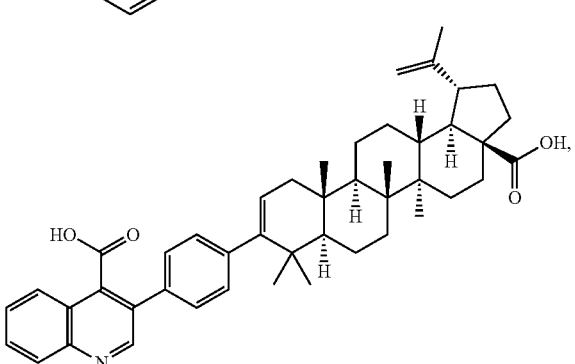
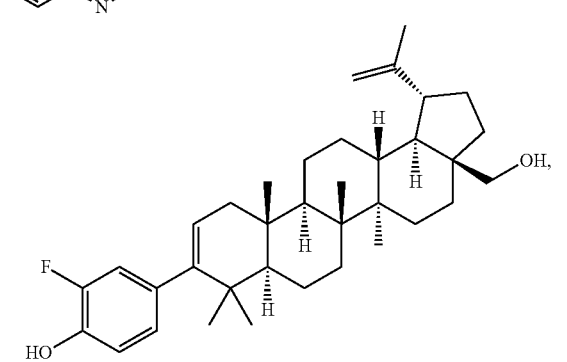
140
-continued
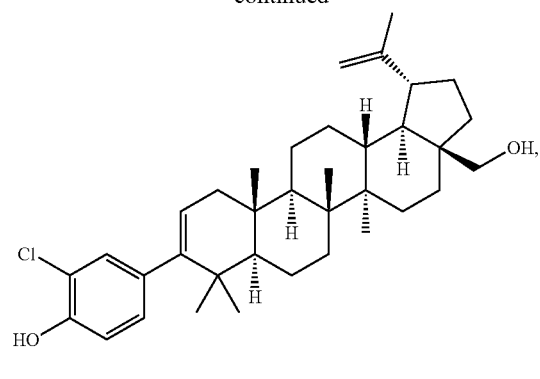
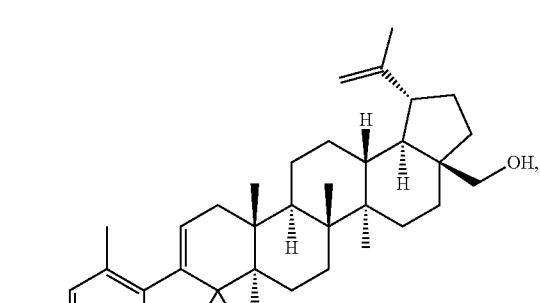
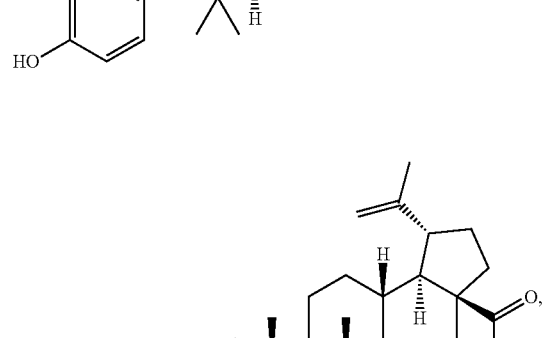
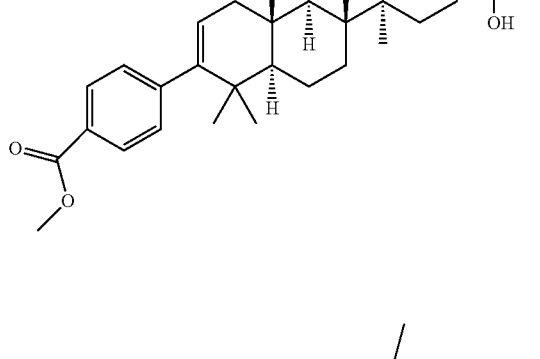
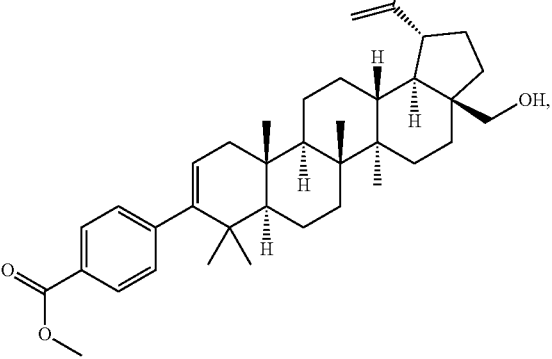

141
-continued
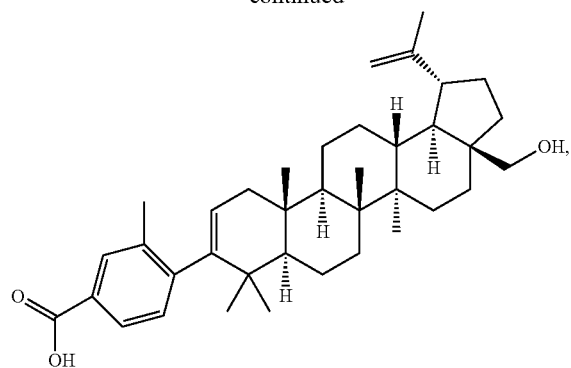
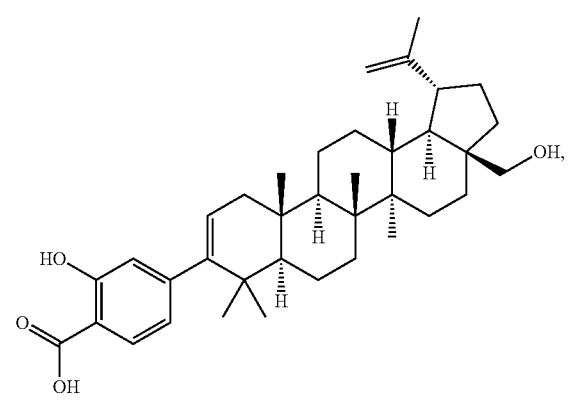
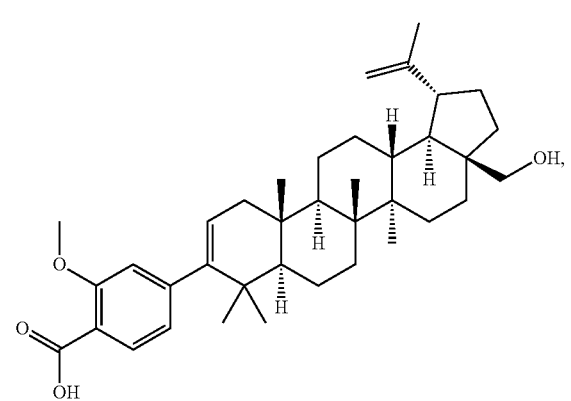
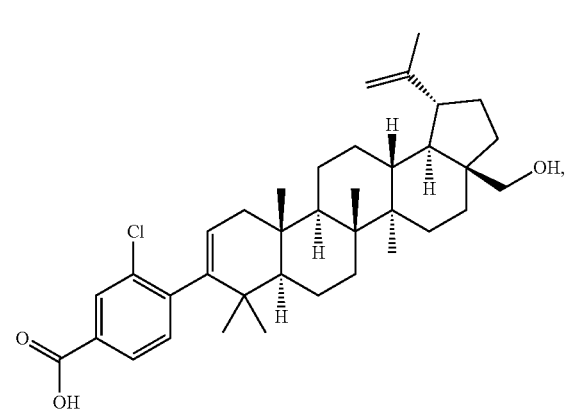
142
-continued
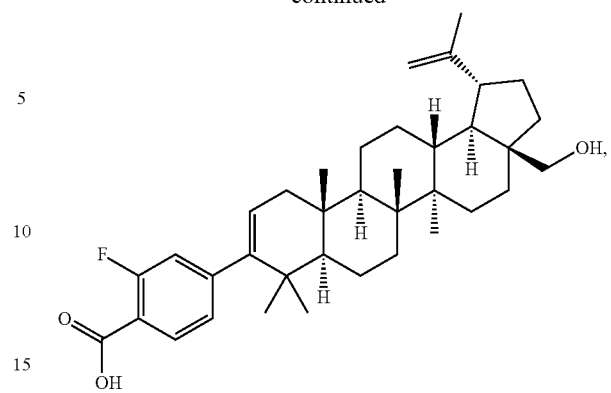
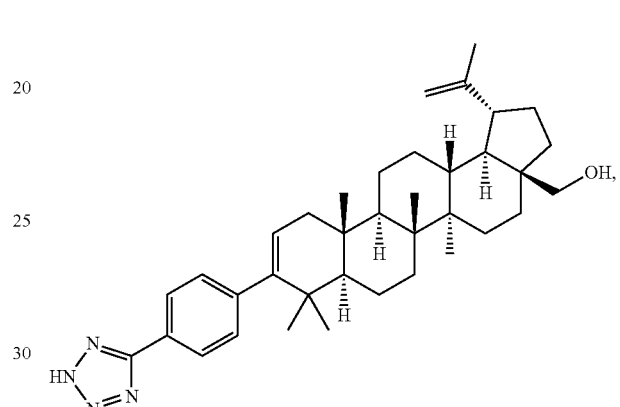
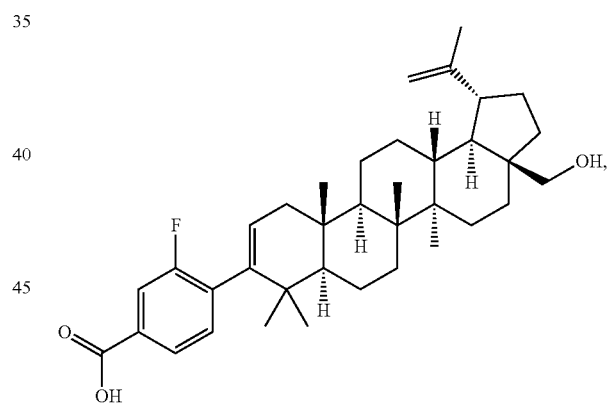
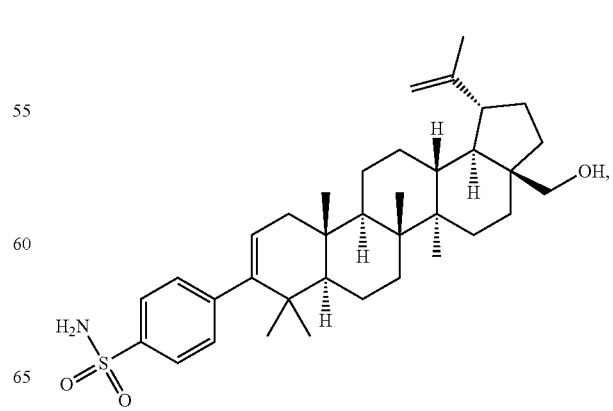

-continued
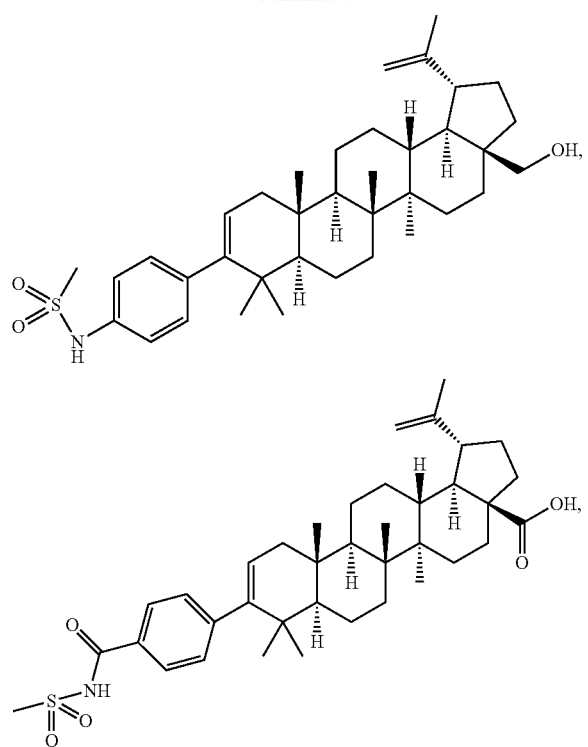
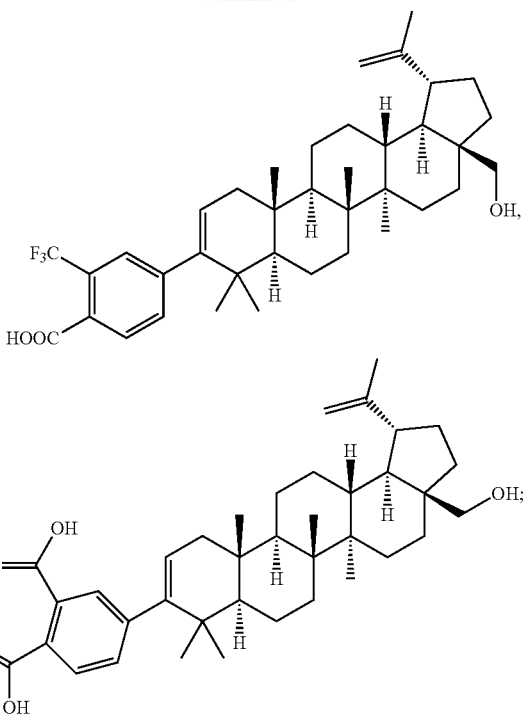
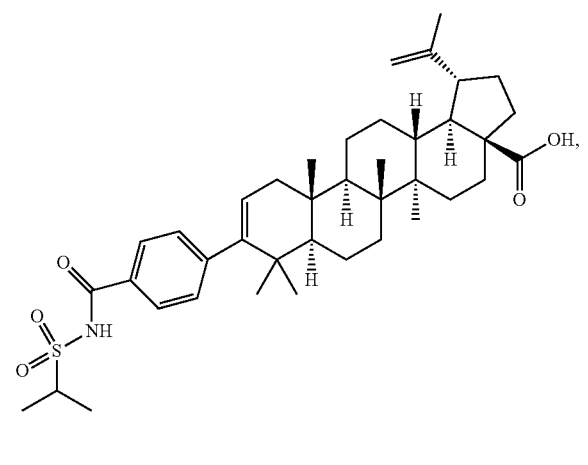
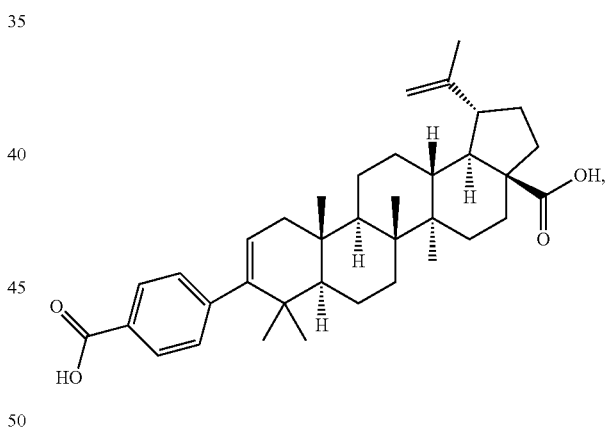
and pharmaceutically acceptable salts thereof.
12. A compound as claimed in claim 11, which is selected from the group consisting of:
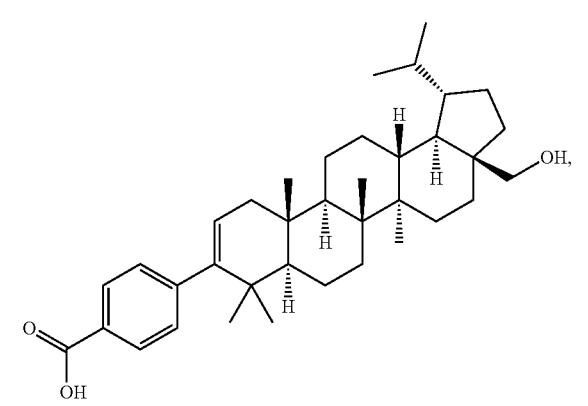
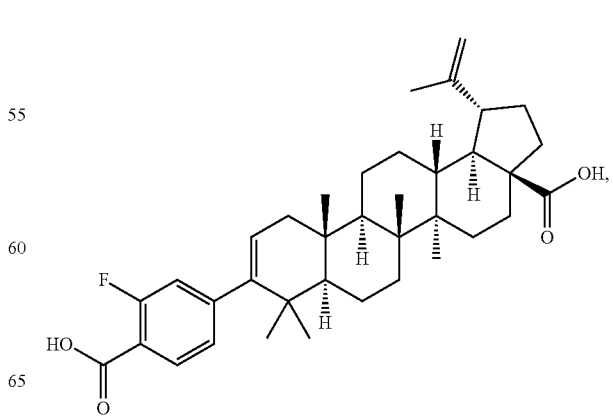

145
-continued
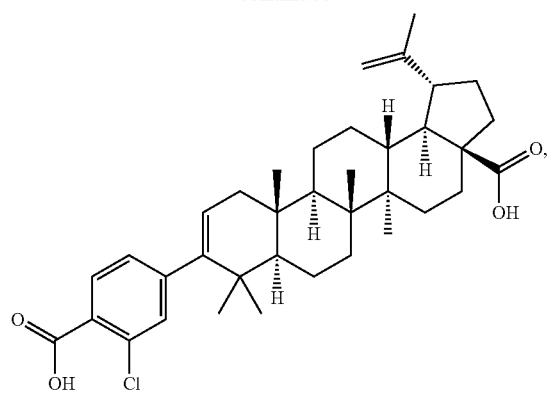
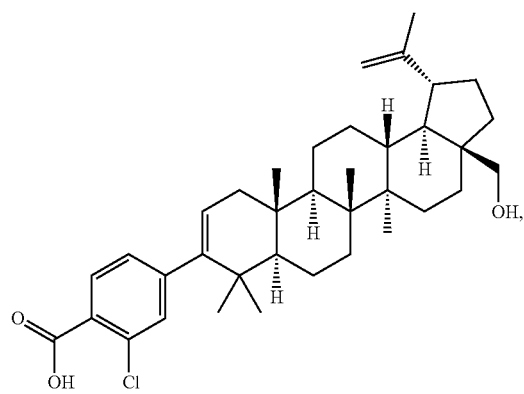
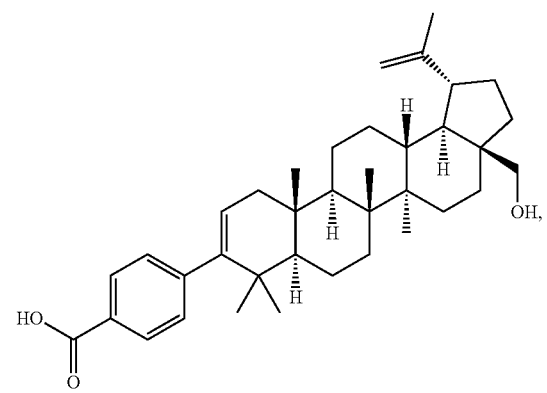
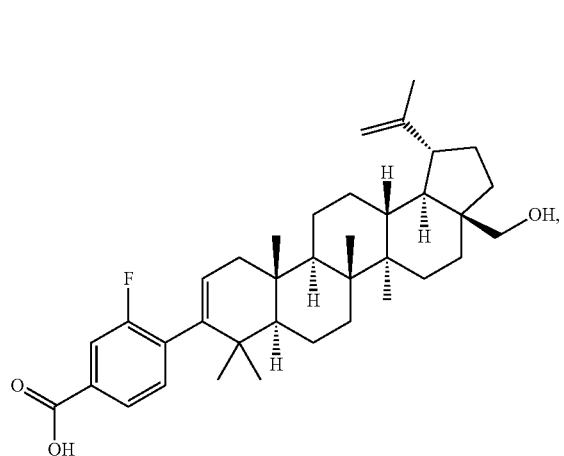
146
-continued
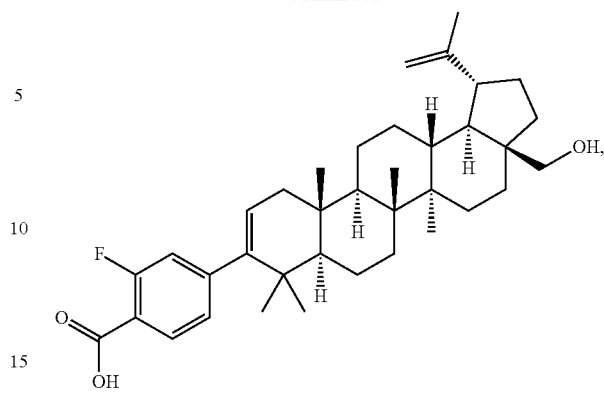
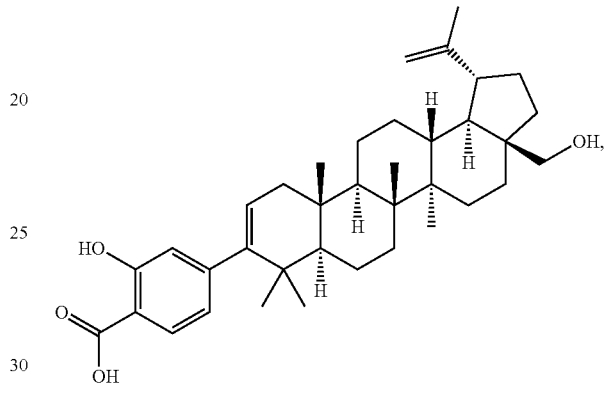
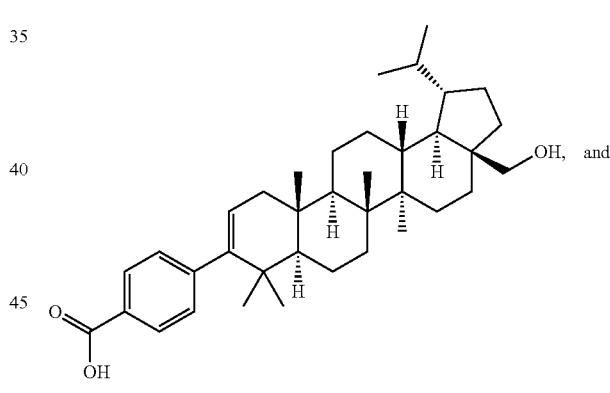
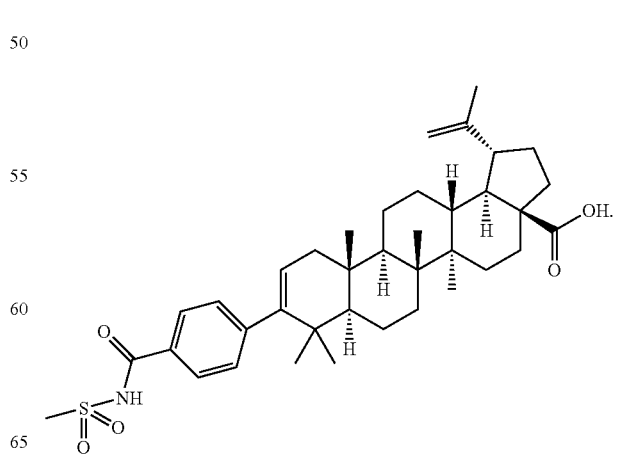

13. A compound which is selected from the group consisting of:

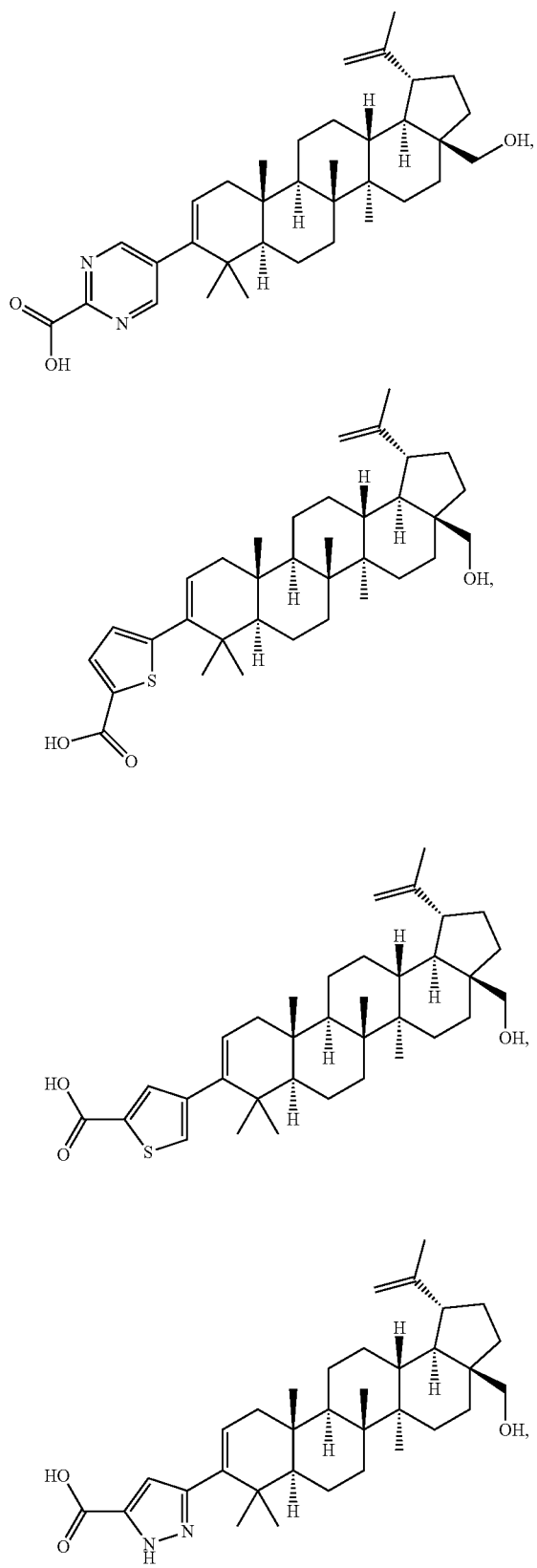

-continued

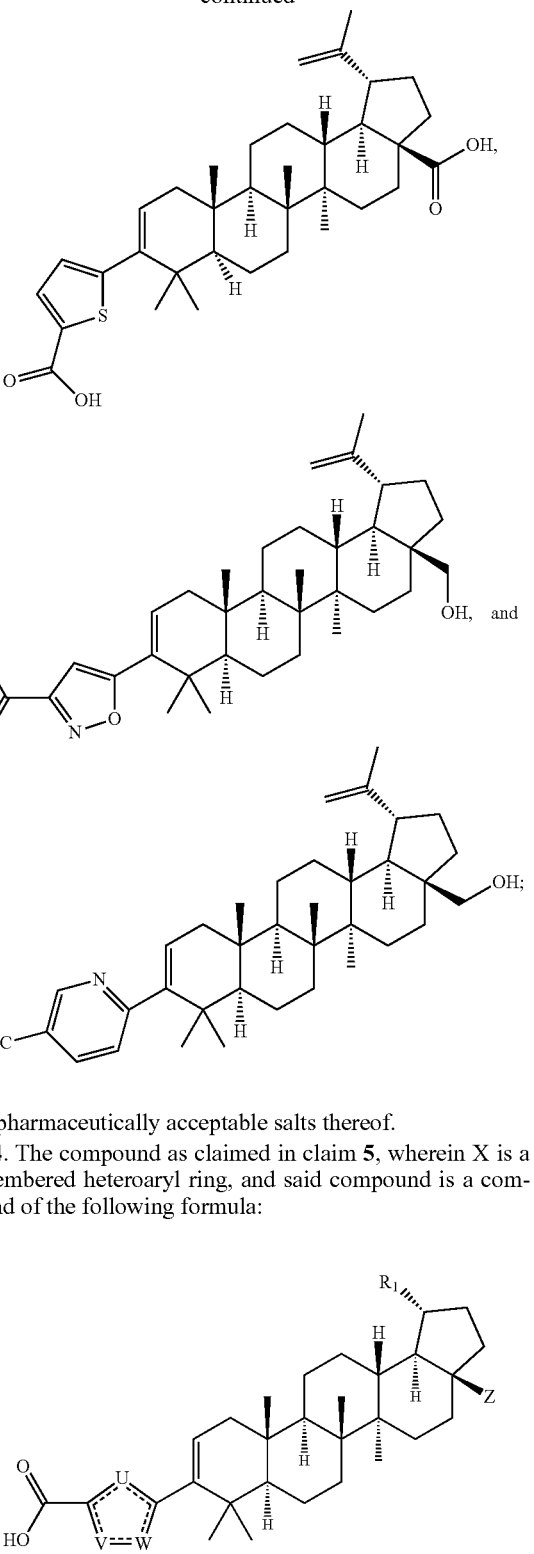

and pharmaceutically acceptable salts thereof.

14. The compound as claimed in claim 5, wherein X is a 5-membered heteroaryl ring, and said compound is a compound of the following formula:

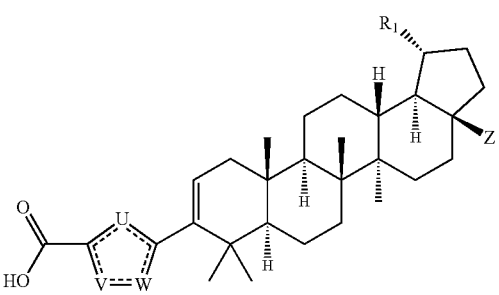

wherein each of U, V and W is selected from the group consisting of C, N, O and S, with the proviso that at least one of U, V and W is other than C.

15. The compound as claimed in claim 14, wherein X is selected from the group of thiophene, pyrazole, isoxazole, and oxadiazole groups.

16. The compound as claimed in claim 15, wherein X is thiophene, pyrazole or isoxazole.

17. The compound as claimed in claim 5, wherein X is a 6-membered heteroaryl ring selected from the group of pyridyl and pyrimidine rings.

18. The compound as claimed in claim 3, wherein X is a phenyl group and Y is —COOH in the para position according to Formula IIa below:

Formula IIa

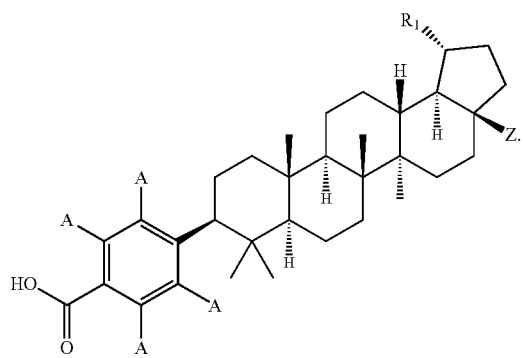

19. A compound which is selected from the group consisting of:

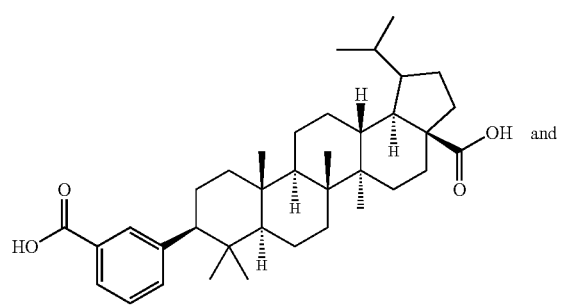

and

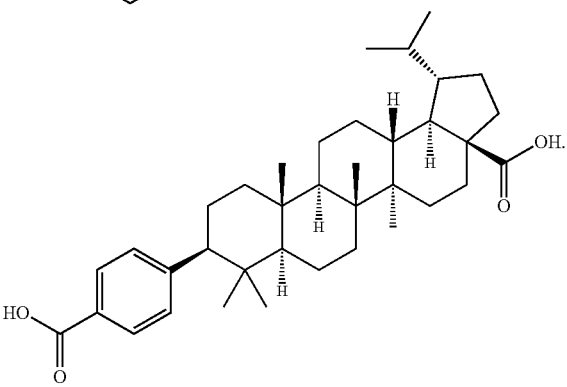

and pharmaceutically acceptable salts thereof.

20. A pharmaceutical composition which comprises an antiviral effective amount of one or more of the compounds as claimed in claim 1, together with one or more pharmaceutically acceptable carriers, excipients or diluents.

21. The pharmaceutical composition of claim 20, useful for ameliorating infection by HIV, which additionally comprises an HIV ameliorating amount of an AIDS treatment agent selected from the group consisting of:
(a) an AIDS antiviral agent;
(b) an anti-infective agent;
(c) an immunomodulator; and
(d) another HIV entry inhibitor.

22. A compound of the following formula:

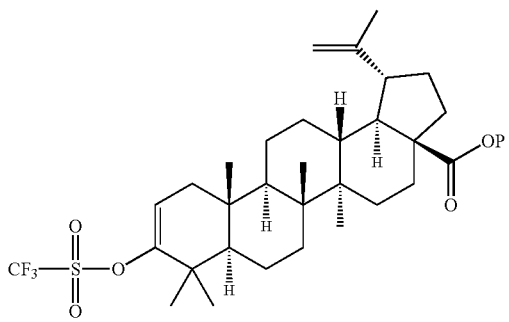

wherein P is a carboxylic acid protective group.

23. A compound of the following formula:

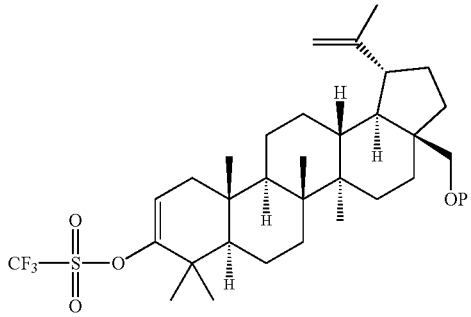

wherein P is a protective group.

24. A compound of the following formula:

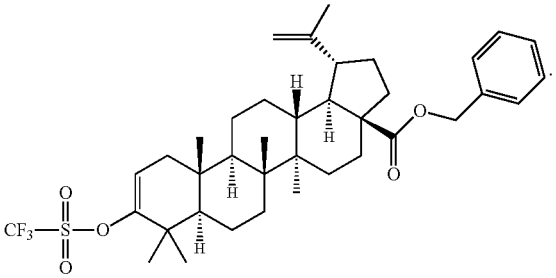

* * * * *